(12) United States Patent
Keefe et al.

(10) Patent No.: US 11,674,135 B2
(45) Date of Patent: Jun. 13, 2023

(54) DNA-ENCODED LIBRARIES HAVING ENCODING OLIGONUCLEOTIDE LINKAGES NOT READABLE BY POLYMERASES

(71) Applicant: X-Chem, Inc., Waltham, MA (US)

(72) Inventors: Anthony D. Keefe, Cambridge, MA (US); Alexander Litovchick, Sudbury, MA (US); Matthew Clark, Lexington, MA (US)

(73) Assignee: X-Chem, Inc., Waltham, MA (US)

( * ) Notice: Subject to any disclaimer, the term of this patent is extended or adjusted under 35 U.S.C. 154(b) by 48 days.

(21) Appl. No.: 14/414,326

(22) PCT Filed: Jul. 12, 2013

(86) PCT No.: PCT/US2013/050303
§ 371 (c)(1),
(2) Date: Jan. 12, 2015

(87) PCT Pub. No.: WO2014/012010
PCT Pub. Date: Jan. 16, 2014

(65) Prior Publication Data
US 2015/0211002 A1    Jul. 30, 2015

Related U.S. Application Data

(60) Provisional application No. 61/671,406, filed on Jul. 13, 2012.

(51) Int. Cl.
*C12N 15/10* (2006.01)
*C12Q 1/68* (2018.01)
*C12Q 1/6869* (2018.01)

(52) U.S. Cl.
CPC ..... *C12N 15/1065* (2013.01); *C12N 15/1044* (2013.01); *C12N 15/1068* (2013.01); *C12Q 1/6869* (2013.01)

(58) Field of Classification Search
CPC ................ C12N 15/1065; C12N 15/1068
See application file for complete search history.

(56) References Cited

U.S. PATENT DOCUMENTS

| | | | |
|---|---|---|---|
| 5,013,830 A | 5/1991 | Ohtsuka et al. | |
| 5,476,930 A | 12/1995 | Letsinger et al. | |
| 5,525,734 A | 6/1996 | Gallop et al. | |
| 5,525,735 A | 6/1996 | Gallop et al. | |
| 5,571,677 A | 11/1996 | Gryaznov | |
| 5,571,903 A | 11/1996 | Gryaznov | |
| 5,573,905 A | 11/1996 | Lerner et al. | |
| 5,585,481 A | 12/1996 | Arnold, Jr. et al. | |
| 5,604,097 A | 2/1997 | Brenner | |
| 5,633,360 A | 5/1997 | Bischofberger et al. | |
| 5,635,400 A | 6/1997 | Brenner | |
| 5,639,603 A | 6/1997 | Dower et al. | |
| 5,654,413 A | 8/1997 | Brenner | |
| 5,656,739 A | 8/1997 | Cubicciotti | |
| 5,670,633 A | 9/1997 | Cook et al. | |
| 5,681,943 A | 10/1997 | Letsinger et al. | |
| 5,695,934 A | 12/1997 | Brenner | |
| 5,696,251 A | 12/1997 | Arnold, Jr. et al. | |
| 5,708,153 A | 1/1998 | Dower et al. | |
| 5,723,289 A | 3/1998 | Eaton et al. | |
| 5,723,598 A | 3/1998 | Lerner et al. | |
| 5,763,175 A | 6/1998 | Brenner | |
| 5,770,358 A | 6/1998 | Dower et al. | |
| 5,770,367 A | 6/1998 | Southern et al. | |
| 5,770,455 A | 6/1998 | Cargill et al. | |
| 5,780,231 A | 7/1998 | Brenner | |
| 5,780,613 A | 7/1998 | Letsinger et al. | |
| 5,789,162 A | 8/1998 | Dower et al. | |
| 5,807,683 A | 9/1998 | Brenner | |
| 5,840,485 A | 11/1998 | Lebl et al. | |
| 5,846,719 A | 12/1998 | Brenner et al. | |
| 5,846,839 A | 12/1998 | Gallop et al. | |
| 5,863,722 A | 1/1999 | Brenner | |
| 5,888,737 A | 3/1999 | DuBridge et al. | |
| 5,942,609 A | 8/1999 | Hunkapiller et al. | |
| 5,962,228 A | 10/1999 | Brenner | |
| 6,013,445 A | 1/2000 | Albrecht et al. | |
| 6,027,890 A | 2/2000 | Ness et al. | |
| 6,060,596 A | 5/2000 | Lerner et al. | |
| 6,087,112 A | 7/2000 | Dale | |
| 6,090,912 A | 7/2000 | Lebl et al. | |
| 6,117,976 A | 9/2000 | Neri et al. | |
| 6,140,489 A | 10/2000 | Brenner | |
| 6,140,493 A | 10/2000 | Dower et al. | |

(Continued)

FOREIGN PATENT DOCUMENTS

| CN | 1898257 A | 1/2007 |
|---|---|---|
| CN | 101321877 A | 12/2008 |

(Continued)

OTHER PUBLICATIONS

Zietlow et al.(Biochemistry 2008, 47, 5460-5464).*
Yoshimura et al.( Organic letters 10.15 (2008): 3227-3230). (Year: 2008).*
Lipinski et al., "Experimental and computational approaches to estimate solubility and permeability in drug discovery and development settings," Adv Drug Deliv Rev. 46(1-3):3-26 (2001).
Extended European Search Report for European Patent Application No. 13816635.0, dated Jan. 5, 2016 (10 pages).

(Continued)

*Primary Examiner* — Sahana S Kaup
(74) *Attorney, Agent, or Firm* — Clark & Elbing LLP

(57) ABSTRACT

The present invention relates to complexes of oligonucleotide-encoded libraries and methods of tagging and using such libraries. In particular, the oligonucleotides and methods can include complexes having at least one linkage for which a polymerase has reduced ability to read or translocate through.

12 Claims, 43 Drawing Sheets

Specification includes a Sequence Listing.

(56) References Cited

U.S. PATENT DOCUMENTS

| | | |
|---|---|---|
| 6,143,497 A | 11/2000 | Dower et al. |
| 6,150,516 A | 11/2000 | Brenner et al. |
| 6,165,717 A | 12/2000 | Dower et al. |
| 6,172,214 B1 | 1/2001 | Brenner |
| 6,172,218 B1 | 1/2001 | Brenner |
| 6,214,553 B1 | 4/2001 | Szostak et al. |
| 6,218,111 B1 | 4/2001 | Southern et al. |
| 6,235,475 B1 | 5/2001 | Brenner et al. |
| 6,281,344 B1 | 8/2001 | Szostak et al. |
| 6,329,177 B1 | 12/2001 | Havlina |
| 6,352,828 B1 | 3/2002 | Brenner |
| 6,368,874 B1 | 4/2002 | Gallop et al. |
| 6,406,848 B1 | 6/2002 | Bridgham et al. |
| 6,416,949 B1 | 7/2002 | Dower et al. |
| 6,479,262 B1 | 11/2002 | Delagrave |
| 6,503,759 B1 | 1/2003 | Still et al. |
| 6,537,776 B1 | 3/2003 | Short |
| 6,537,803 B1 | 3/2003 | Amara et al. |
| 6,576,426 B2 | 6/2003 | Southern et al. |
| 6,607,878 B2 | 8/2003 | Sorge |
| 6,627,748 B1 | 9/2003 | Ju et al. |
| 6,654,505 B2 | 11/2003 | Bridgham et al. |
| 6,706,481 B2 | 3/2004 | Rajendran et al. |
| 6,806,052 B2 | 10/2004 | Bridgham et al. |
| 6,831,994 B2 | 12/2004 | Bridgham et al. |
| 6,844,324 B1 | 1/2005 | Zhang et al. |
| 6,846,655 B1 | 1/2005 | Wagner et al. |
| 6,867,290 B2 | 3/2005 | Goldsborough |
| 6,875,736 B2 | 4/2005 | Rana |
| 6,936,467 B2 | 8/2005 | Kmiec et al. |
| 6,936,477 B2 | 8/2005 | Still et al. |
| 6,994,963 B1 | 2/2006 | Murphy et al. |
| 7,033,753 B1 | 4/2006 | Kool |
| RE39,545 E | 4/2007 | Cargill |
| RE39,571 E | 4/2007 | Cargill |
| RE39,606 E | 5/2007 | Cargill |
| 7,217,522 B2 | 5/2007 | Brenner |
| RE39,793 E | 8/2007 | Brenner |
| 7,282,370 B2 | 10/2007 | Bridgham et al. |
| 7,365,179 B2 | 4/2008 | Brenner |
| 7,393,665 B2 | 7/2008 | Brenner |
| 7,407,757 B2 | 8/2008 | Brenner |
| 7,413,536 B1 | 8/2008 | Dower et al. |
| 7,413,854 B2 | 8/2008 | Pedersen et al. |
| 7,442,160 B2 | 10/2008 | Liu et al. |
| 7,479,472 B1 | 1/2009 | Harbury et al. |
| 7,491,494 B2 | 2/2009 | Liu et al. |
| 7,537,897 B2 | 5/2009 | Brenner et al. |
| 7,557,068 B2 | 7/2009 | Liu et al. |
| 7,704,925 B2 | 4/2010 | Gouliaev et al. |
| 7,727,713 B2 | 6/2010 | Pedersen et al. |
| 7,749,699 B2 | 7/2010 | Kool |
| 7,771,935 B2 | 8/2010 | Liu et al. |
| 7,915,201 B2 | 3/2011 | Franch et al. |
| 7,935,658 B2 | 5/2011 | Morgan et al. |
| 7,972,992 B2 | 7/2011 | Morgan et al. |
| 7,972,994 B2 | 7/2011 | Morgan et al. |
| 7,989,395 B2 | 8/2011 | Morgan et al. |
| 7,998,673 B2 | 8/2011 | French et al. |
| RE43,097 E | 1/2012 | Albrecht et al. |
| 8,148,068 B2 | 4/2012 | Brenner |
| 8,206,901 B2 | 6/2012 | Freskgard et al. |
| 8,361,713 B2 | 1/2013 | Bridgham et al. |
| 8,722,583 B2 | 5/2014 | Gouliaev et al. |
| 2001/0031475 A1 | 10/2001 | Gallop et al. |
| 2002/0034732 A1 | 3/2002 | Capon et al. |
| 2002/0072887 A1 | 6/2002 | Szalma et al. |
| 2003/0049616 A1 | 3/2003 | Brenner et al. |
| 2003/0059826 A1 | 3/2003 | Janda et al. |
| 2003/0119051 A1 | 6/2003 | Wiessler et al. |
| 2003/0143561 A1 | 7/2003 | Pedersen et al. |
| 2003/0187240 A1 | 10/2003 | Cook et al. |
| 2003/0215846 A1 | 11/2003 | Watt et al. |
| 2004/0014090 A1 | 1/2004 | Neri et al. |
| 2004/0049008 A1 | 3/2004 | Pedersen et al. |
| 2004/0083427 A1 | 4/2004 | Wada |
| 2004/0259102 A1 | 12/2004 | Kool |
| 2005/0059049 A1 | 3/2005 | Moen et al. |
| 2005/0100968 A1 | 5/2005 | Gallop et al. |
| 2005/0158765 A1 | 7/2005 | Morgan et al. |
| 2005/0176948 A1 | 8/2005 | Gouliaev et al. |
| 2005/0221316 A1 | 10/2005 | Pedersen et al. |
| 2005/0221318 A1 | 10/2005 | Gouliaev et al. |
| 2005/0227281 A1 | 10/2005 | Liu et al. |
| 2005/0247001 A1 | 11/2005 | Gouliaev et al. |
| 2005/0255491 A1 | 11/2005 | Lee et al. |
| 2006/0099589 A1 | 5/2006 | Pedersen et al. |
| 2006/0099592 A1 | 5/2006 | Freskgard et al. |
| 2006/0099626 A1 | 5/2006 | Harbury et al. |
| 2006/0115829 A1 | 6/2006 | Mao et al. |
| 2006/0121470 A1 | 6/2006 | Pedersen |
| 2006/0154246 A1 | 7/2006 | Neri et al. |
| 2006/0160125 A1 | 7/2006 | Kool |
| 2006/0166197 A1 | 7/2006 | Gouliaev et al. |
| 2006/0177833 A1 | 8/2006 | Brenner |
| 2006/0193869 A1 | 8/2006 | Barrat et al. |
| 2006/0199192 A1 | 9/2006 | Kool et al. |
| 2006/0211030 A1 | 9/2006 | Brenner |
| 2006/0234231 A1 | 10/2006 | Freskgard et al. |
| 2006/0246450 A1 | 11/2006 | Franch et al. |
| 2006/0269920 A1 | 11/2006 | Freskgard et al. |
| 2006/0292603 A1 | 12/2006 | Gouliaev et al. |
| 2007/0026397 A1 | 2/2007 | Freskgard et al. |
| 2007/0042401 A1 | 2/2007 | Morgan et al. |
| 2007/0213519 A1 | 9/2007 | Gouliaev et al. |
| 2007/0224607 A1* | 9/2007 | Morgan ............ C12N 15/1068 435/6.12 |
| 2008/0193983 A1 | 8/2008 | Gouliaev et al. |
| 2008/0220982 A1 | 9/2008 | Vu |
| 2008/0305957 A1 | 12/2008 | Thisted et al. |
| 2008/0318802 A1 | 12/2008 | Brenner |
| 2009/0005256 A1 | 1/2009 | Bittker et al. |
| 2009/0011957 A1 | 1/2009 | Gouliaev et al. |
| 2009/0035824 A1 | 2/2009 | Liu et al. |
| 2009/0062147 A1 | 3/2009 | Morgan et al. |
| 2009/0143232 A1 | 6/2009 | Pedersen et al. |
| 2009/0143244 A1 | 6/2009 | Bridgham et al. |
| 2009/0239211 A1 | 9/2009 | Freskgard et al. |
| 2009/0239768 A1 | 9/2009 | Hansen et al. |
| 2009/0264300 A1 | 10/2009 | Franch et al. |
| 2010/0016177 A1 | 1/2010 | Pedersen et al. |
| 2010/0094036 A1 | 4/2010 | Hirata et al. |
| 2010/0159526 A1 | 6/2010 | Jendrisak et al. |
| 2010/0184611 A1 | 7/2010 | Neri et al. |
| 2010/0184661 A1 | 7/2010 | Luo et al. |
| 2011/0003290 A1 | 1/2011 | Gale et al. |
| 2011/0104785 A1 | 5/2011 | Vaidyanathan et al. |
| 2011/0136697 A1 | 6/2011 | Morgan et al. |
| 2011/0183863 A1 | 7/2011 | Wagner et al. |
| 2011/0251089 A1 | 10/2011 | Morgan et al. |
| 2011/0262898 A1* | 10/2011 | Dong .................. C12P 19/34 435/6.1 |
| 2011/0319278 A1 | 12/2011 | Neri et al. |
| 2012/0004137 A1 | 1/2012 | Wagner et al. |
| 2012/0053091 A1 | 3/2012 | Wagner |
| 2012/0071329 A1 | 3/2012 | Morgan et al. |
| 2012/0107840 A1 | 5/2012 | Wagner et al. |
| 2012/0245040 A1 | 9/2012 | Morgan et al. |
| 2013/0102545 A1 | 4/2013 | Gao et al. |
| 2013/0281324 A1 | 10/2013 | Gouliaev et al. |

FOREIGN PATENT DOCUMENTS

| | | |
|---|---|---|
| CN | 102317513 A | 1/2012 |
| DE | 19646372 C1 | 6/1997 |
| DE | 19642751 A1 | 4/1998 |
| EP | 1533385 A1 | 5/2005 |
| EP | 1423400 B1 | 8/2006 |
| EP | 1905829 A2 | 4/2008 |
| EP | 1828381 B1 | 1/2009 |
| EP | 2175019 A2 | 4/2010 |
| EP | 2186897 A1 | 5/2010 |
| EP | 2236606 A2 | 10/2010 |
| EP | 1957644 B1 | 12/2010 |

(56) References Cited

FOREIGN PATENT DOCUMENTS

| | | |
|---|---|---|
| EP | 2258870 A2 | 12/2010 |
| EP | 2305808 A1 | 4/2011 |
| EP | 2311786 A2 | 4/2011 |
| EP | 1558744 B1 | 6/2011 |
| EP | 2336315 A2 | 6/2011 |
| EP | 2338990 A2 | 6/2011 |
| EP | 2341140 A1 | 7/2011 |
| EP | 2348124 A2 | 7/2011 |
| EP | 2348125 A2 | 7/2011 |
| EP | 2216338 B1 | 3/2013 |
| EP | 2272856 B1 | 11/2015 |
| GB | 9315847.5 | 7/1993 |
| JP | 5292967 A | 11/1993 |
| JP | 8000268 A | 1/1996 |
| JP | 2002315577 A | 10/2002 |
| JP | 2008-543289 A | 12/2008 |
| WO | WO-92/22875 A1 | 12/1992 |
| WO | WO-93/06121 A1 | 4/1993 |
| WO | WO-93/20242 A1 | 10/1993 |
| WO | WO-94/08051 A1 | 4/1994 |
| WO | WO-95/04160 A1 | 2/1995 |
| WO | WO-95/06293 A1 | 3/1995 |
| WO | WO-95/12608 A1 | 5/1995 |
| WO | WO-96/35699 A1 | 11/1996 |
| WO | WO-97/32999 A1 | 9/1997 |
| WO | WO-98/31700 A1 | 7/1998 |
| WO | WO-99/10485 A1 | 3/1999 |
| WO | WO-99/18240 A2 | 4/1999 |
| WO | WO-00/20639 A1 | 4/2000 |
| WO | WO-00/23458 A1 | 4/2000 |
| WO | WO-00/32823 A1 | 6/2000 |
| WO | WO-00/61775 A1 | 10/2000 |
| WO | WO-01/16352 A1 | 3/2001 |
| WO | WO-02/40664 A1 | 5/2002 |
| WO | WO-02/074929 A2 | 9/2002 |
| WO | WO-02/102820 A1 | 12/2002 |
| WO | WO-02/103008 A2 | 12/2002 |
| WO | WO-03/078050 A2 | 9/2003 |
| WO | WO-03/078445 A2 | 9/2003 |
| WO | WO-03/078446 A2 | 9/2003 |
| WO | WO-03/078625 A2 | 9/2003 |
| WO | WO-03/078626 A2 | 9/2003 |
| WO | WO-03/078627 A2 | 9/2003 |
| WO | WO-2004/001042 A2 | 12/2003 |
| WO | WO-2004/009814 A1 | 1/2004 |
| WO | WO-2004/013070 A2 | 2/2004 |
| WO | WO-2004/016767 A2 | 2/2004 |
| WO | WO-2004/024929 A2 | 3/2004 |
| WO | WO-2004/039825 A2 | 5/2004 |
| WO | WO-2004/056994 A2 | 7/2004 |
| WO | WO-2004/074429 A2 | 9/2004 |
| WO | WO-2004/074501 A2 | 9/2004 |
| WO | WO-2004/083427 A2 | 9/2004 |
| WO | WO-2005/008240 A1 | 1/2005 |
| WO | WO-2005/026387 A1 | 3/2005 |
| WO | WO-2005/058479 A2 | 6/2005 |
| WO | WO-2005/078122 A2 | 8/2005 |
| WO | WO-2005/090566 A2 | 9/2005 |
| WO | WO-2006/048025 A1 | 5/2006 |
| WO | WO-2006/053571 A2 | 5/2006 |
| WO | WO-2006/079061 A2 | 7/2006 |
| WO | WO-2006/135786 A2 | 12/2006 |
| WO | WO-2007/041201 A2 | 4/2007 |
| WO | WO-2007/053358 A2 | 5/2007 |
| WO | WO-2007/062664 A2 | 6/2007 |
| WO | WO-2009/066447 A1 | 5/2009 |
| WO | WO-2009/077173 A2 | 6/2009 |
| WO | WO-2009/152824 A1 | 12/2009 |
| WO | WO-2010/086602 A1 | 8/2010 |
| WO | WO-2010/094027 A1 | 8/2010 |
| WO | WO-2010/094036 A1 | 8/2010 |
| WO | WO-2010/094040 A1 | 8/2010 |
| WO | WO2010094036 * | 8/2010 |
| WO | WO2010094036 A1 * | 8/2010 |
| WO | WO-2011/082796 A2 | 7/2011 |
| WO | WO-2011/120042 A1 | 9/2011 |
| WO | WO-2011/127933 A1 | 10/2011 |
| WO | WO-2012/125733 A2 | 9/2012 |
| WO | WO-2013/036810 A1 | 3/2013 |
| WO | WO-2014/012010 A1 | 1/2014 |
| WO | WO-2015/091207 A1 | 6/2015 |

OTHER PUBLICATIONS

Office Action and English translation for Chinese Patent Application No. 201380047931.0, dated Dec. 29, 2015 (13 pages).
Abe et al., "Structure analysis of oligonucleotide in organic solvent," Nucleic Acids Symposium Series. 50:25-6 (2006).
Amato, "Speeding up a chemical game of chance," Science. 257(5068):330-1 (1992).
Anonymous, "Non-enzymatic ligation of single-stranded and duplex DNA," Glen Research Report of Products for RNA and DNA Oligonucleotide Synthesis. 10 (1997). (1 page).
"Substantial Background Reduction in Ligase-based Apoptosis Detection Using Newly Designed Hairpin Oligoprobes," available in PMC Jun. 18, 2007, published in final edited form as: Biotechniques. 27:1130-2 (1999) (5 pages).
Balanov et al., "Development of DNA-encoded library containing $10^9$ backbone cyclic peptides on 7 μM glass beads," Peptides Frontiers of Peptide Science, American Peptide Symposia. 5:49-50 (2002).
Bartel et al., "Isolation of new ribozymes from a large pool of random sequences," Science. 261(5127):1411-8 (1993).
Berezovski et al., "Non-SELEX: selection of aptamers without intermediate amplification of candidate oligonucleotides," Nat Protoc. 1(3):1359-69 (2006).
Brenner et al., "Encoded combinatorial chemistry," Proc Natl Acad Sci U.S.A. 89(12):5381-3 (1992).
Brenner et al., "Gene expression analysis by massively parallel signature sequencing (MPSS) on microbead arrays," Nat Biotechnol. 18(6): 630-4 (2000).
Brenner et al., "In vitro cloning of complex mixtures of DNA on microbeads: physical separation of differentially expressed cDNAs," Proc Natl Acad Sci U.S.A. 97(4): 1665-70 (2000).
Bruick et al., "Template-directed ligation of peptides to oligonucleotides," Chem Biol. 3(1):49-56 (1996).
Cherepanov et al., "Scanning mutagenesis using T4 DNA ligase and short degenerate DNA oligonucleotides containing tri-nucleotide mismatches," J Biochem. 132(1):143-7 (2002).
Chiu et al., "Visualizing a correlation between siRNA localization, cellular uptake, and RNAi in living cells," Chem Biol. 11(8):1165-75 (2004).
Clark et al., "Design, synthesis and selection of DNA-encoded small-molecule libraries," Nat Chem Biol. 5(9):647-54 (2009).
Ekland et al., "Structurally complex and highly active RNA ligases derived from random RNA sequences," Science. 269(5222):364-70 (1995).
File History for European Patent Application No. 03757752.5 (1,559 pages).
File History for U.S. Appl. No. 10/525,817 mailed May 1, 2011 (735 pages).
Gartner et al., "The generality of DNA-templated synthesis as a basis for evolving non-natural small molecules," J Am Chem Soc. 123(28):6961-3 (2001).
Goodwin et al., "Template-directed synthesis: use of a reversible reaction," J Am Chem Soc. 114(23):9197-8 (1992).
Géron-Landre et al., "Sequence-specific fluorescent labeling of double-stranded DNA observed at the single molecule level," Nucleic Acids Res. 31(20):e125 (2003) (8 pages).
Halpin et al., "DNA display I. Sequence-encoded routing of DNA populations," PLoS Biol. 2(7):E173 (2004) (7 pages).
Halpin et al., "DNA display II. Genetic manipulation of combinatorial chemistry libraries for small-molecule evolution," PLoS Biol. 2(7):E174 (2004) (9 pages).
Harada et al., "In vitro selection of optimal DNA substrates for T4 RNA ligase," Proc Natl Acad Sci U.S.A. 90(4):1576-9 (1993).
Herrlein et al., "A covalent lock for self-assembled oligonucleotide conjugates," J Am Chem Soc. 117(40):10151-2 (1995).
International Preliminary Report on Patentability and Written Opin-

(56) References Cited

OTHER PUBLICATIONS ion for International Application No. PCT/US2013/050303, dated Nov. 29, 2013 (9 pages).
International Search Report and Written Opinion for International Application No. PCT/US2013/050303, dated Nov. 29, 2013 (17 pages).
Ito et al., "Modification of lipase with various synthetic polymers and their catalytic activities in organic solvent," Biotechnol Prog. 10(4):398-402 (1994).
Janda, "Tagged versus untagged libraries: methods for the generation and screening of combinatorial chemical libraries," Proc Natl Acad Sci U.S.A. 91(23):10779-85 (1994).
Jarosch et al., "In vitro selection using a dual RNA library that allows primerless selection," Nucleic Acids Res. 34(12):e86 (2006) (9 pages).
Jenne et al., "A novel ribozyme with ester transferase activity," Chem Biol. 5(1):23-34 (1998).
Jäschke et al., "Synthesis and properties of oligodeoxyribonucleotide-polyethylene glycol conjugates," Nucleic Acids Res. 22(22):4810-7 (1994).
Kempe et al., "Chemical and enzymatic biotin-labeling of oligodeoxyribonucleotides," Nucleic Acids Res. 13(1):45-57 (1985).
Kinoshita et al., "Enzymatic synthesis of code regions for encoded combinatorial chemistry (ECC)," Nucleic Acids Symp Ser. 34:201-2 (1995).
Kinoshita et al., "Enzymatic synthesis of sequencing primers based on a library of tetramers," Chem Express. 7:149-52 (1992).
Kinoshita et al., "Strand ligation in a double-stranded DNA by T4 RNA ligase," Chem Lett. 9:797-8 (1996).
Kitamura et al., "Construction of block-shuffled libraries of DNA for evolutionary protein engineering: Y-ligation-based block shuffling," Protein Eng. 15(10):843-53 (2002).
Kitamura et al., "Development of systemic in vitro evolution and its application to generation of peptide-aptamer-based inhibitors of cathepsin E," J Mol Biol. 387(5):1186-98 (2009).
Lebl, "Parallel personal comments on "classical" papers in combinatorial chemistry," J Comb Chem. 1(1):3-24 (1999).
Lee et al., "Ribozyme-catalyzed tRNA aminoacylation," Nat Struct Biol. 7(1):28-33 (2000).
Li et al., "Kinetics of RNA degradation by specific base catalysis of transesterification involving the 2'-hydroxyl group," J Am Chem Soc. 121(23):5364-72 (1999).
Liu, "Development of amplifiable and evolvable unnatural molecules," website of Dr. D. R. Liu, publicly <http://web.archive.ora/web/20000311112631/http://evolve.havard.edu> retreived May 9, 2007 (2 pages).
Liu, "The chemistry and chemical biology of molecular evolution," website of Dr. D.R. Liu, <http://web.archive.org/web/200103011751 07/http://evolve.havard edu>, retrieved Sep. 5, 2007 (2 pages).
Liu, "The Chemistry of Molecular Evolution," website of Dr. D.R. Liu <http://web.archive.ora/web/20001015144553/http://evolve. havard.edu>, retrieved Sep. 5, 2007 (3 pages).
Morpurgo et al., "An approach to increased polyplex gene delivery by peptides selected from a phage display library," J Biochem Biophys Methods. 52(1):31-43 (2002).
Needels et al., "Generation and screening of an oligonucleotide-encoded synthetic peptide library," Proc Natl Acad Sci U.S.A. 90(22):10700-4 (1993).
Nielsen et al., "Toward chemical implementation of encoded combinatorial libraries," Methods. 6(4):361-71 (1994).
Nielsen et al., "Synthetic methods for the implementation of encoded combinatorial chemistry," J Am Chem Soc. 115(12):9812-3 (1993).
Nishigaki et al., "T4 RNA ligase: Its potential and applications to molecular biotechnology," Symp Biofunc Chem. 13:394-6 (1998) (5 pages).
Nishigaki et al., "Y-ligation: An efficient method for ligating single-stranded DNAs and RNAs with T4 RNA ligase," Mol Divers. 4(3):187-90 (1998).

Nishigaki, "RNA Ligases," Encyclopedia of Molecular Biology (2002) (3 pages).
Pochet et al., "Solid-supported ligation primer," Nucleic Acids Res. 16(4):1619 (1988).
Roberts et al., "RNA-peptide fusions for the in vitro selection of peptides and proteins," Proc Natl Acad Sci U.S.A. 94(23):12297-302 (1997).
Rohatgi et al., "Kinetic and mechanistic analysis of nonenzymatic, template-directed oligoribonucleotide ligation," J Am Chem Soc. 118(14):3332-9 (1996).
Rohatgi et al., "Nonenzymatic, template-directed ligation of oligoribonucleotides is highly regioselective for the formation of 3'-5' phosphodiester bonds," J Am Chem Soc. 118(14):3340-4 (1996).
Rozenman et al., "DNA-templated synthesis in organic solvents," Chembiochem. 7(2):253-6 (2006).
Scheuermann et al., "DNA-encoded chemical libraries," J Biotechnol. 126(4):568-81 (2006).
Schmidt et al., "Information transfer from DNA to peptide nucleic acids by template-directed syntheses," Nucleic Acids Res. 25(23):4792-6 (1997).
Schmitz et al., "Solid-phase enzymatic synthesis of oligonucleotides," Org Lett. 1(11):1729-31 (1999).
Stryer, "Eukaryotic Chromosomes and Gene Expression," Biochemistry, W.H. Freeman and Company: New York, 4th ed., 975-88 (1995).
Suga et al., "Structural and kinetic characterization of an acyl transferase ribozyme," J Am Chem Soc. 120(6):1151-6 (1998).
Suga et al., "Unusual metal ion catalysis in an acyl-transferase ribozyme," Biochemistry. 37(28):10118-25 (1998).
Summerer et al., "DNA-templated synthesis: more versatile than expected," Angew Chem Int Ed Engl. 41(1):89-90 (2002).
Supplementary Methods for Clark et al., "Design, Synthesis and selection of DNA-encoded small molecule libraries," Nat Chem Biol. 5(9):1-57 (2009).
Tabuchi et al., "An efficient ligation method in the making of an in vitro Virus for in vitro Protein evolution," Biol Proced Online. 4:49-54 (2002).
Tamura et al., "Oligonucleotide-directed peptide synthesis in a ribosome- and ribozyme-free system," Proc Natl Acad Sci U.S.A. 98(4):1393-7 (2001).
Tessier et al., "Ligation of single-stranded oligodeoxyribonucleotides by T4 RNA ligase," Anal Biochem. 158(1):171-8 (1986).
Visscher et al., "Template-directed synthesis of acyclic oligonucleotide analogues," J Mol Evol. 28(1-2):3-6 (1988).
Walder et al., "Complementary carrier peptide synthesis: general strategy and implications for prebiotic origin of peptide synthesis," Proc Nat Acad Sci U.S.A. 76(1):51-5 (1979).
Xu et al., "Chemical and enzymatic properties of bridging 5'-S-phosphorothioester linkages in DNA," Nucleic Acids Res. 26(13):3159-64 (1998).
Xu et al., "High sequence fidelity in a non-enzymatic DNA autoligation reaction," Nucleic Acids Res. 27(3):875-81 (1999).
Yoshimura et al.,"Ultrafast reversible photo-cross-linking reaction: toward in situ DNA manipulation," Org Lett. 10(15):3227-30 (2008).
Zhang et al., "Single-stranded DNA ligation by T4 RNA ligase for PCR cloning of 5'-noncoding fragments and coding sequence of a specific gene," Nucleic Acids Res. 24(5):990-1 (1996).
Third-Party Observation pursuant to Art. 115 EPC for European Patent Application No. 10741877, filed Mar. 14, 2016 (38 pages).
Mullah et al., "Efficient synthesis of double dye-labeled oligodeoxyribonucleotide probes and their application in a real time PCR assay," Nucleic Acids Res. 26(4):1026-031 (1998).
Thelwell et al., "Mode of action and application of Scorpion primers to mutation detection," Nucleic Acids Res. 28(19):3752-61 (2000).
Wagner, "Gene inhibition using antisense oligodeoxynucleotides," Nature. 372:333-5 (1994).
Wagner et al., "Antisense gene inhibition by oligonucleotides containing C-5 propyne pyrimidines," Science. 260:1510-3(1993).
Yamana et al., "Synthesis and binding properties of oligonucleotides containing an azobenzene linker," Nucleosides and Nucleotides. 17(1-3):233-42 (1998).

(56) References Cited

OTHER PUBLICATIONS

Communication pursuant to Article 94(3) EPC for European Patent Application No. 10741877.4, dated Mar. 24, 2016 (6 pages).
Anonymous, "PDC-CE Phosphoramidite," Glen Research Report of Products for RNA and DNA Oligonucleotide Synthesis. (2004) (3 pages).
Anonymous, "PDU-CE Phosphoramidite," Glen Research Report of Products for RNA and DNA Oligonucleotide Synthesis. (2004) (3 pages).
Anonymous, "5-F-DU-CE Phosphoramidite," Glen Research Report of Products for RNA and DNA Oligonucleotide Synthesis. (2004) (3 pages).
Anonymous, "Versatile New Reagents: Pyrene-dU and Perylene-dU," Glen Research Report of Products for RNA and DNA Oligonucleotide Synthesis. (2008) (2 pages).
Korshun et al., "5-(1-pyrenylethynyl)-2'-deoxyuridine, a novel fluorescent nucleoside analog," Bioorg Khim. 22:923-5 (1996).
Written Opinion for Singapore Patent Application No. 11201500250V, dated Mar. 7, 2016 (7 pages).
Office Action and English translation for Eurasian Patent Application No. 201590195, dated Mar. 3, 2016 (5 pages).
Blondal et al., "Isolation and characterization of a thermostable RNA ligase 1 from a Thermus scotoductus bacteriophage TS2126 with good single-stranded DNA ligation properties," Nucleic Acids Res. 33(1):135-42 (2005).
Cummins et al., "Characterization of fully 2'-modified oligoribonucleotide hetero- and homoduplex hybridization and nuclease sensitivity," Nucleic Acids Res. 23(11):2019-24 (1995).
Third-Party Observation pursuant to Art. 115 EPC for European Patent Application No. 12830083, dated Dec. 8, 2016 (51 pages).
Uhlenbeck et al., "2. T4 RNA Ligase," The Enzymes. 15:31-58 (1982).
Written Opinion for Singaporean Patent Application No. 11201500250V, dated Dec. 15, 2016 (6 pages).
Sastry et al., "Cross-linking of DNA-binding proteins to DNA with psoralen and psoralen furan-side monoadducts. Comparison of action spectra with DNA-DNA cross-linking," J Biol Chem. 272(6):3715-23 (1997).
Dimitri et al., "Transcription elongation past O6-methylguanine by human RNA polymerase II and bacteriophage T7 RNA polymerase," Nucleic Acids Res. 36(20):6459-71 (2008).
Engelhart et al., "Nonenzymatic ligation of DNA with a reversible step and a final linkage that can be used in PCR," Chembiochem. 13(8):1121-4 (2012).
Hoepfner et al., "Amplified primer extension assay for psoralen photoproducts provides a sensitive assay for a (CG)6TA(CG)2(TG)8 Z-DNA torsionally tuned probe: preferential psoralen photobinding to one sliand of a B-Z junction," Biochemistry 32(29):7542-8 (1993).
Tornaletti et al., "Transcription arrest at an abasic site in the transcribed strand of template DNA," Chem Res Toxicol. 19(9):1215-20 (2006).
First Examination Report for New Zealand Patent Application No. 703766, dated Apr. 28, 2017 (3 pages).
Examination Report No. 1 for Australian Patent Application No. 2013289993, dated Apr. 28, 2017 (3 pages).
Third-Party Observation pursuant to Art. 115 EPC for European Patent Application No. 13816635, dated Apr. 28, 2017 (68 pages).
"Pharmacology Frontier—Signal, Protein factor, Gene and Modern Pharmacology", compiled mainly by WEI Erqlng, Science and Technology Press, p. 314-316 (1999) (4 pages).
Jinfeng et al., "Gene Analysis and Biochip Technique," complied mainly by DING, Hubei Science and Technology Press, p. 108-109 (2004) (3 pages).
Liang et al., "A supra-photoswitch involving sandwiched DNA base pairs and azobenzenes for light-driven nanostructures and nanodevices," Small. 5(15):1761-8 (2009).
Notification of Material filed by a Third Party for Australian Patent Application No. 2012304387, dated Feb. 16, 2017 (44 pages).

Notification of Third-Party Submission of Information and English Translation for Japanese Patent Application No. 2014-529907, dated Jan. 16, 2017 (2 pages).
Pre-Issuance Submission by Third-Party for U.S. Appl. No. 14/343,306, dated May 25, 2016 (22 pages).
Third-Party Observation pursuant to Art. 115 EPC for European Patent Application No. 10741877 dated Feb. 16, 2017 (28 pages).
Third-Party Observation pursuant to Art. 115 EPC for European Patent Application No. 12830083, filed May 3, 2017 (9 pages).
Communication pursuant to Article 94(3) EPC for European Patent Application No. 13816635.0, dated May 23, 2017 (5 pages).
El-Sagheer et al., "Click nucleic acid ligation: applications In biology and nanotechnology," Acc Chem Res. 45(8):1258-67 (2012).
Paredes et al., "Click chemistry for rapid labeling and ligation of RNA," Chembiochem. 12(1):125-31 (2011).
Office Action for Eurasian Patent Application No. 201490534, dated Jun. 21, 2017 (4 pages).
Office Action for Japanese Patent Application No. 2015-521850, dated Jun. 28, 2017 (8 pages).
Berger et al., "Chemistry on nucleic acid templates," Chem Biodivers. 7(10):2581-615 (2010).
El-Sagheer et al., "Efficient RNA synthesis by in vitro transcription of a triazole-modified DNA template," Chem Commun (Camb). 47(44):12057-8 (2011).
Examination Report for African Patent Application No. AP/P/2014/007483, dated Oct. 27, 2016 (4 pages).
Examination Report for Indian Patent Application No. 6461/CHENP/2011, dated Oct. 13, 2017 (6 pages).
Extended European Search Report for European Patent Application No. 17163865.3, dated May 17, 2017 (9 pages).
First Examination Report for New Zealand Patent Application No. 736922, dated Nov. 27, 2017 (4 pages).
Fujimoto et al., "A light-controlled reversible DNA photoligation via carbazole-tethered 5-carboxyvinyluracil," Org Lett. 10(3):397-400 (2008).
Further Examination Report for New Zealand Patent Application No. 722289, dated Nov. 27, 2017 (2 pages).
Li et al., "DNA-templated organic synthesis: nature's strategy for controlling chemical reactivity applied to synthetic molecules," Angew Chem Int Ed Engl. 43(37):4848-70 (2004).
Nakamura et al., "Template directed reversible photochemical ligation of oligodeoxynucleotides," Molecules 17(1):163-78 (2012).
Notification of Material filed by a Third Party for Australian Patent Application No. 2013289993, dated Oct. 27, 2017 (25 pages).
Ogino et al., "Template-directed DNA photoligation via alpha-5-cyanovinyldeoxyuridine," Org Lett. 7(14):2853-6 (2005).
Qiu et al., "A diazirine-based nucleoside analogue for efficient DNA interstrand photocross-linking," J Am Chem Soc. 130(44):14398-9 (2008).
Second Written Opinion for Singaporean Patent Application No. 2014011381, dated Oct. 19, 2017 (8 pages).
Third Party Submission for Canadian Patent Application No. 2752543 dated May 11, 2017 (29 pages).
Wang et al., "Relative stabilities of triple helices composed of combinations of DNA, RNA and 2'-O-methyl-RNA backbones: chimeric circular oligonucleotides as probes," Nucleic Acids Res. 23(7):1157-64 (1995).
Yoshimura et al., "Highly selective and sensitive template-directed photoligation of DNA via 5-carbamoylvinyl-2'-deoxycytidine," Org Lett. 8(22):5049-51 (2006).
Decision of Rejection for Japanese Application No. 2014-529907, dated Jan. 9, 2018 (10 pages).
Integrated DNA Technologies, Inc. for "Int Spacer 9" (iSp9—Product No. 1391 from Oct. 16, 2006 and Nov. 9, 2006) available at <https://web.archive.org/web/20071109184957/http://www.idtdna.com:80/Catalog/Modifications/RNAModifications.aspxhttps://web.archive.org/web/20061016193020/https://www.idtdna.com/catalog/Modifications/Modifications.aspx?ProductID=1391> (2 pages).
Integrated DNA Technologies, Inc. for "Int Uni-Link™ Amino Modifier" (iUniAmM—Product No. 1440 from Oct. 16, 2006 and Nov. 15, 2006) available at <https://web.archive.org/web/20061115041630/http://www.idtdna.com:80/Catalog/Modifications/

(56) References Cited

OTHER PUBLICATIONS

RNAModifications.aspxhttps://web.archive.org/web/20061016184659/https://www.idtdna.com/Catalog/Modifications/Modifications.aspx?ProductID=1440> (2 pages).
Supporting information for Rozenman and Liu, ChemBioChem, pp. S1-S18 (2006).
Ren et al., "Formation of Stable DNA Loops by Incorporation of Nonpolar, Non-Hydrogen-Bonding Nucleoside Isosteres," Available in PMC Sep. 27, 2010, published in final edited form as: Angew Chem Int Ed Engl. 35(7):743-6 (1996) (8 pages).
Efimov et al., "Cross-linked nucleic acids: formation, structure, and biological function," Russ J Bioorg Chem. 36(1):49-72 (2010).
Beaucage et al., "The functionalization of oligonucleotides via phosphoramidite derivatives," Tetrahedron 49(10):1925-63 (1993).
Yamana et al., "Synthesis of oligonucleotides containing a new azobenzene fragment with efficient photoisomerizability," Bioorg Med Chem. 7(12):2977-83 (1999).
Asanuma et al., "Photocontrol of DNA duplex formation by using azobenzene-bearing oligonucleotides," Chembiochem. 2(1):39-44 (2001).
Wang et al., "A thermostable azo-linker for reversible photoregulation of DNA replication," Tetrahedron Letters 49(34):5087-9 (2008).
Wu et al., "Reversible stability switching of a hairpin DNA via a photo-responsive linker unit," Chem Commun (Camb). 14(14):1915-7 (2009).
Lewis et al., "Synthesis, structure, and photochemistry of exceptionally stable synthetic DNA hairpins with stilbene diether linkers," J Am Chem Soc. 124(41):12165-73 (2002).
Jäschke, Chapter 18: Oligonucleotide-Poly(ethylene glycol) Conjugates: Synthesis, Properties, and Applications. *ACS Symposium Series*, p. 265-83 (1997).
Bonora et al., "Synthesis and characterization of high-molecular mass polyethylene glycol-conjugated oligonucleotides," Bioconjug Chem. 8(6):793-7 (1997).
Polyethylene Glycols. Prepared at the 31st JECFA (1987), published in 1988 in FAO Food and Nutrition Paper 38 (FNP 38), and in 1992 in vol. 3 of "Compendium of Food Additive Specifications" (FNP 52) (11 pages).
Malakhov et al., "Synthesis and fluorescent properties of 5-(1-pyrenylethynyl)-2'-deoxyuridine-containing oligodeoxynucleotides," Russ J Bioorg Chem. 26(1):34-44 (2000).
Cui, "Have the primary structures of biomacromolecules been selected in a Darwinian fashion to adapt to the surrounding environments of our planet?," IUBMB Life 61(8):860-3 (2009).
Glen Research Information and MSDS for 5'-Dimethoxytrityl-5-[N-(trifluoroacetylaminohexyl)-3-acrylimido]-2'-deoxyUridine,3'-[(2-cyanoethyl)-(N,N-diisopropyl)]-phosphoramidite (Catalogue No. 10-1039-xx from Apr. 14, 2005 and Aug. 19, 2004), available at: https://web.archive.org/web/20050414005644/http://www.glenresearch.com/ProductFiles/10-1039.html; https://web.archive.org/web/20040819072021/http://www.glenresearch.com/ProductFiles/MSDS/m10-1039.html (4 pages.).
Salunkhe et al., "Control of folding and binding of oligonucleotides by use of a nonnucleotide linker," J Am Chem Soc. 114(23):8768-72 (1992).
Notice of Preliminary Rejection for Korean Patent Application No. 10-2017-7029869, dated Feb. 15, 2018 (10 pages).
Glen Research Information and MSDS for pdC-CE Phosphoramidite (Catalogue No. 10-1014-xx from Sep. 1, 2004 and Mar. 8, 2005), available at: https://web.archive.org/web/20050308232245/http://www.glenresearch.com/ProductFiles/10-1014.html; https://web.archive.org/web/20040901150244/http://www.glenresearch.com/ProductFiles/m10-1014.html (4 pages).
Glen Research Information and MSDS for pdU-CE Phosphoramidite (Catalogue No. 10-1054-xx from Oct. 28, 2004 and Mar. 8, 2005), available at: https://web.archive.org/web/20050308232237/http://www.glenresearch.com/ProductFiles/10-1054.html; https://web.archive.org/web/20041028103548/http://www.glenresearch.com/ProductFiles/MSDS/m10-1054.html (3 pages).
Glen Research Information for Pyrene-dU-CE Phosphoramidite (Catalogue No. 10-1590-xx from Aug. 21, 2008 and Dec. 2, 2008), available at: https://web.archive.org/web/20081202060550/http://www.glenresearch.com/Catalog/structural.html#a101590; https://web.archive.org/web/20080821194747/http://www.glenresearch.com/GlenReports/GR19-28.html (9 pages).
Glen Research Information and MSDS for 5-F-dU-CE Phosphoramidite (Catalogue No. 10-1092-xx from Oct. 28, 2004 and Apr. 28, 2005), available at: https://web.archive.org/web/20050428232151/http://www.glenresearch.com/ProductFiles/10-1092.html; https://web.archive.org/web/20041028091346/http://www.glenresearch.com/ProductFiles/MSDS/m10-1092.html (4 pages).
Third-Party Observation concerning IL 236633 (X-Chem, Inc.) filed Mar. 4, 2018 (82 pages).
Extended European Search Report for European Application No. 18158509.2, dated Jun. 29, 2018 (11 pages).
Notification of Reexamination for Chinese Application No. 2013800479310, dated Jul. 4, 2018 (15 pages).
Asanuma et al. "Synthesis of azobenzene-teathered DNA for Reversible photo-regulation of DNA functions: hybridization and transcription," Protocol. 2(1):203-212 (11 pages).
Jinfeng Ding et al., "Gene analysis and Bio-chip technology," Wuhan: Hubei Science and Technology Press. (2004) (5 pages).
*Pharmacological frontier—signal, protein factor, gene and modern pharmacology* . . . Edited by Wei, Erqing. Beijing: Science Publishing House. 314-316 (1999) (8 pages).
Luebke et al., "Nonenymatic ligation of double-helical DNA by alternate-strand triple helix formation," Nucleic Acids Res. 20(12):3005-9 (1992).
Asanuma et al., "Synthesis of azobenzene-tethered DNA for reversible photo-regulation of DNA functions: hybridization and transcription," Protocol. 2(1):203-212 (2007) (11 pages).
Chapter 5: Crosslinking and Photoactivatable Reagents. *Molecular Probes Handbook: A Guide to Fluorescent Probes and Labeling Technologies, 11th Edition*. ThermoFischer Scientific. (2010) (18 pages).
Clark et al., Supplementary Methods for "Design, synthesis and selection of DNA-encoded smallmolecule libraries," Nat Chem Biol. 5(9):647-54 (2009) (57 pages).
Communication of a Notice of Opposition for European Patent Application No. 13816635.0, dated Jan. 10, 2019 (37 Pages).
First Examination Report for New Zealand Patent Application No. 739931, dated Feb. 15, 2019 (3 pages).
First Examination Report for New Zealand Patent Application No. 744078, dated Feb. 18, 2019 (3 pages).
Kanaya et al., "Template-Directed Polymerization of Oligoadenylates Using Cyanogen Bromide," Biochemistry. 25(23):7423-30 (1986).
Kleiner et al., "In Vitro Selection of a DNA-Templated Small-Molecule Library Reveals a Class of Macrocyclic Kinase Inhibitors," J Am Chem Soc. 132(33):11779-11791 (2010).
Kocalka et al., "Rapid and Efficient DNA Strand Cross-Linking by Click Chemistry," Chembiochem. 9(8):1280-5 (2008).
Kore et al., "Efficient synthesis of 3-cyanovinylcarbazole-1'-beta-deoxyriboside-5'-triphosphate: a reversible photo-cross-linking probe," Tetrahedron Lett. 53(31):4012-14 (2012).
Luebke et al., "Nonenzymatic ligation of double-helical DNA by alternate-strand triple helix formation," Nucleic Acids Res. 20(12):3005-9 (1992).
Pujari et al., "Cross-Linked DNA Generated by 'Bis-click' Reactions with Bis-functional Azides: Site Independent Ligation of Oligonucleotides via Nucleobase Alkynyl Chains," J Org Chem. 75(24):8693-6 (2010).
Xiong et al., "Cross-Linked DNA: Site-Selective 'Click' Ligation in Duplexes with Bis-Azides and Stability Changes Caused by Internal Cross-Links," Bioconjug Chem. 23(6):1230-43 (2012).
Xiong et al., "Stepwise 'Click' Chemistry for the Template Independent Construction of a Broad Variety of Cross-Linked Oligonucleotides: Influence of Linker Length, Position, and Linking Number on DNA Duplex Stability," J Org Chem. 76:5584-5597 (2011).
Yoshimura et al., Supporting Information for "Ultrafast Reversible Photocrosslinking Reaction: Toward in Situ DNA Manipulation," Org Lett. (2008) (20 pages).

(56) References Cited

OTHER PUBLICATIONS

U.S. Appl. No. 61/531,820 filed , Keefe et al..
U.S. Appl. No. 61/536,929 filed , Keefe et al..
Communication pursuant to Article 94(3) EPC for European Patent Application No. 18158509.2, dated Jul. 22, 2019 (9 pages).
Examination Report No. 1 for Australian Patent Application No. 2018202665, dated Sep. 11, 2019 (3 pages).
First Examination Report for Canadian Patent Application No. 2,879,019, dated Sep. 25, 2019 (4 pages).
Further Examination Report for New Zealand Patent Application No. 744078, dated Jun. 7, 2019 (2 pages).
Khakshoor et al., "Chemistry of nucleic acids: impacts in multiple fields," Chem Commun. 47(25):7018-24 (2011).
Lallana et al., "Reliable and efficient procedures for the conjugation of biomolecules through Huisgen azide-alkyne cycloadditions," Angew Chem Int Ed Engl. 50(38):8794-804 (2011).
Notice of Preliminary Rejection for Korean Patent Application No. 10-2015-7002779, dated Jul. 25, 2019 (13 pages).
Examination Report for Indian Application No. 425/CHENP/2015, dated Dec. 13, 2019 (7 pages).
Fujimoto et al., "Template directed photochemical synthesis of branched oligodeoxynucleotides via 5-carboxyvinyldeoxyuridine," Tetrahedron Lett. 41(49):9437-9440 (2000).
Notification of Reasons for Rejection for Japanese Application No. 2018-201106, dated Dec. 19, 2019 (7 pages).
Interlocutory Decision in Opposition Proceedings (Art. 101(3)(a) and 106(2) EPC) for European Application No. 13816635.0, dated Apr. 7, 2020 (144 pages).

\* cited by examiner

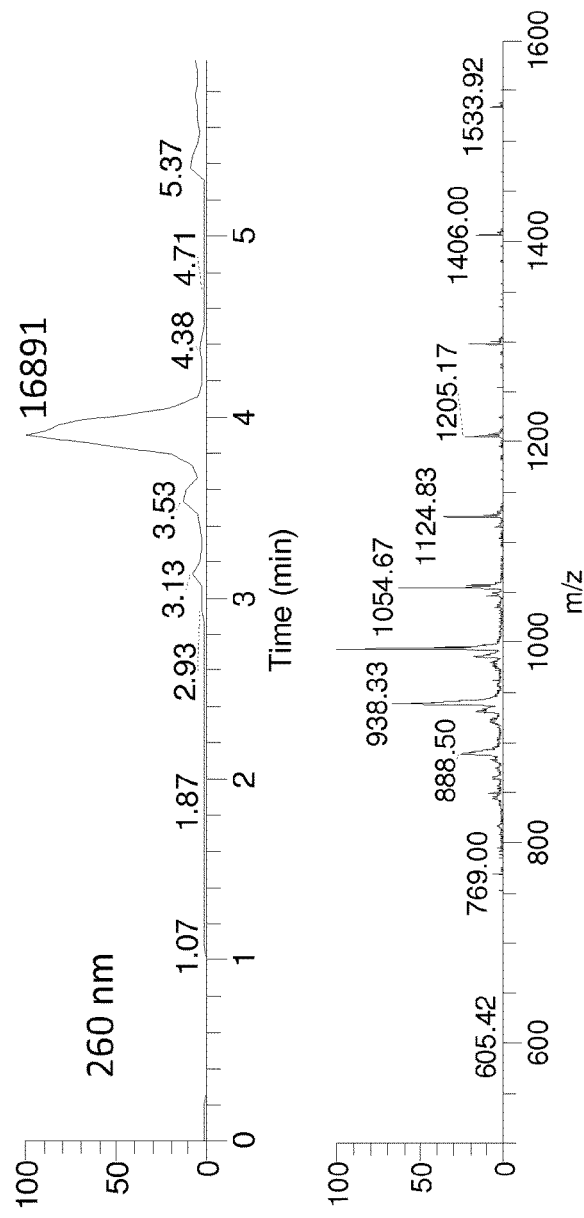
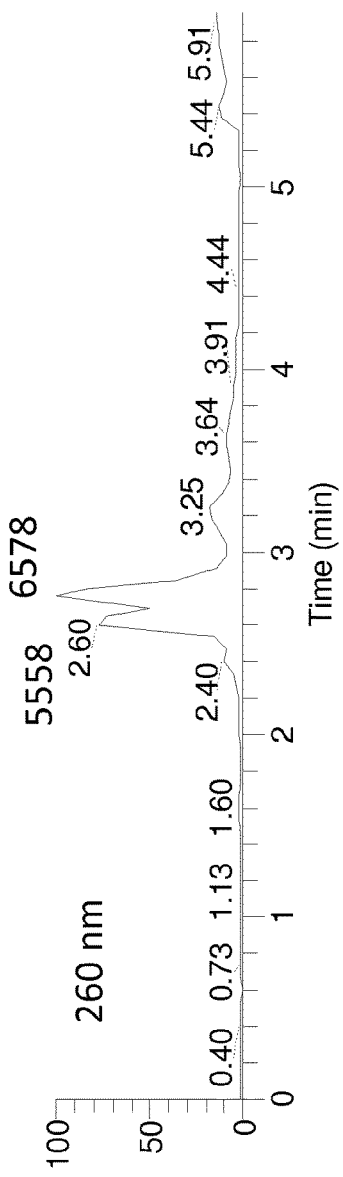
Figure 7

5PSO2_A9_TA (MW 11,556.3 Da)
5'-Psoralen (C2-linked)-TAGCGGATGCAAAAAAAAGGCGAGCT TGCGTACTG-3'

PSO_HP_A9_TCT (MW 6,087.1 Da)
5'-AAAAAA AAAGCATCCGCTCT -3'

Figure 11

Psoralen (C2) Phosphoramidite

Tag1_PsoCVU (MW 3,662.5 Da)
5'-AAAAACTCAGGT-3'

SplintC_PsoC2 (MW 4,529.0 Da)
5'-TCCGCTCGACCTGAG-3'

5PsoC2_A9_GA (MW 11,580.6 Da)
5'-Psoralen (C2)-GAGCGGATGCAAAAAAAAAGGGCGAGCTTGCGTACTG-3'

5'-NNNNNNNNNNT PNNNNNNNNNNNNNNNNNN-3'
3'-NNNAGNNNNNNN-5'

P = 5'-Psoralen

5Bio_Tag_PsoCVU (MW 4,232.1 Da)
5'-/5BioTEG/AAAAACTCAGGT-3'

/5BioTEG/ is a proprietary biotin modification

5PsoC2_A9_GA (MW 11,580.6 Da)
5'-Psoralen (C2)-GAGCGGATGCAAAAAAAAAGGCGAGCTTGCGTACTG-3'

SplintC_PsoC2 (MW 4,529.0 Da)
5'-TCCGCTCGACCTGAG-3'

FAMprimer (MW 5,099.5 Da)
5'-/56-FAM/AGTACGCAAGCTCGC-3'

Phos-SplintC_PsoC2
5'-Monophosphate-TCCGCTCGACCTGAG-3'

/56-FAM/ Phosphoramidite

Psoralen (C2) Phosphoramidite 5-(Carboxy)vinyl-2'-deoxyuridine

SplintC_CVU
5'-TCCGCTCAACCTGAG-3'

SplintA_CVU
5'-TCCGCTTAACCTGAG-3'

Tag1_PsoCVU (MW 3,662.5 Da)
5'-AAAAACTCAGGT-3'

CVU_G (MW 11,576.2 Da)
5'- (5-(Carboxy)vinyl-2'-deoxyuridine)GAGCGGATGCAAAAAAAGGGCGAGCTTGCGTACTG -3'

CVU_A (MW 11560.2 Da)
5'- (5-(Carboxy)vinyl-2'-deoxyuridine)AAGCGGATGCAAAAAAAGGGCGAGCTTGCGTACTG -3'

S_IDTN₃
TGCGGTCTAACTGTCTAG TTCACCTTCTCCGGAATGAACAGG/3AzideN/

S_IDTalkyne
/5Hexynyl/TACCGAATTGCCGCCTGATTGAAGCAATCGGGTGCTATGCTT

5Hexynyl Modification

TKR_Central: /5Hexynyl/GGAATGAACAGG GTAAGCTGGAGTGAAGGCGTTATG/3AzideN/

S_IDTN₃: TGCGGTCTAACTGTCTAGTTCACCTTCTCCGGAATGAACAGG /3AzideN/

TKR_DBCO_S: /DBCO/GAAGGGCGTTATGTCCGTACTCTTGCAATCGGGTGCTATGCTT

DBCO Phosphoramidite

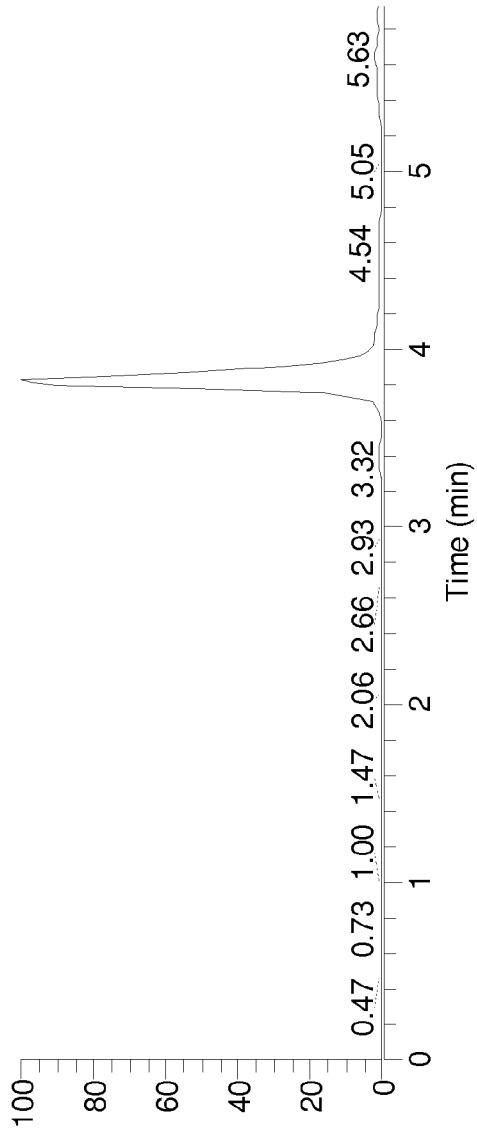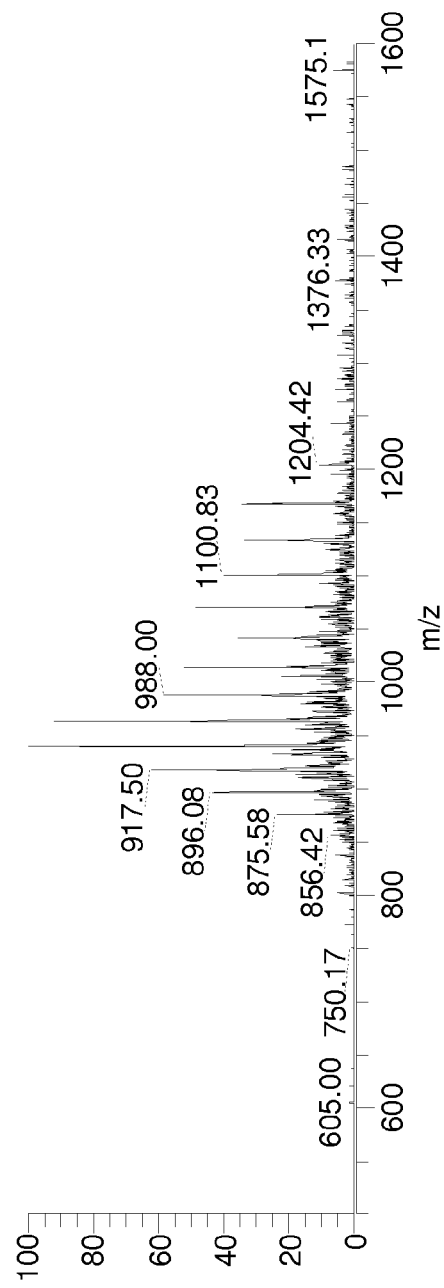
Figure 31

Conjugate_Click_S
TGCGGTCTAACTGTCTAGTTCACCTTCTCCGGAATGAACAGG(click)TACCGAATTGCCGCCTGATTGAAG-CAATCGGGTGCTATGCTT Conjugate_Click_L
TGCGGTCTAACTGTCTAGGCACTTGTTCGTTTGCCAGTGTGAGGAATGAACAGG(click)TACCGAATTGCCTTCCTCG-TACAGTTCTAAGGCGCTTGGACACCACTTCAATCGGGTGCTATGCTT

Figure 32

32 cycles, starting conc 5 pM
1-Marker
2- Solution PCR
3- Emulsion PCR

TKR_2_click_S
TGCGGTCTAACTGTCTAGTTCACCTTCTCCGGAATGAACAGG(CLICK)GGAATGAACAGGGTAAGCTGGAGTGAAGGCGTTATG(DBCO)
GAAGGCGTTATGTCCGTACTCTTGCAATCGGGTGCTATGCTT TKR_2_click_L
TGCGGTCTAACTGTCTAGGCACTTGTCGTTTGCCAGTGTGATGGACACCACTTGGAATGAACAGG(CLICK)GGAATGAACAGGGTAAGC
TGGAGTGAAGGCGTTATG(DBCO)GAAGGCGTTATGTGATATCCGTGGTGTCGTGAGTTCCAATCGGGTGCTATGCTT

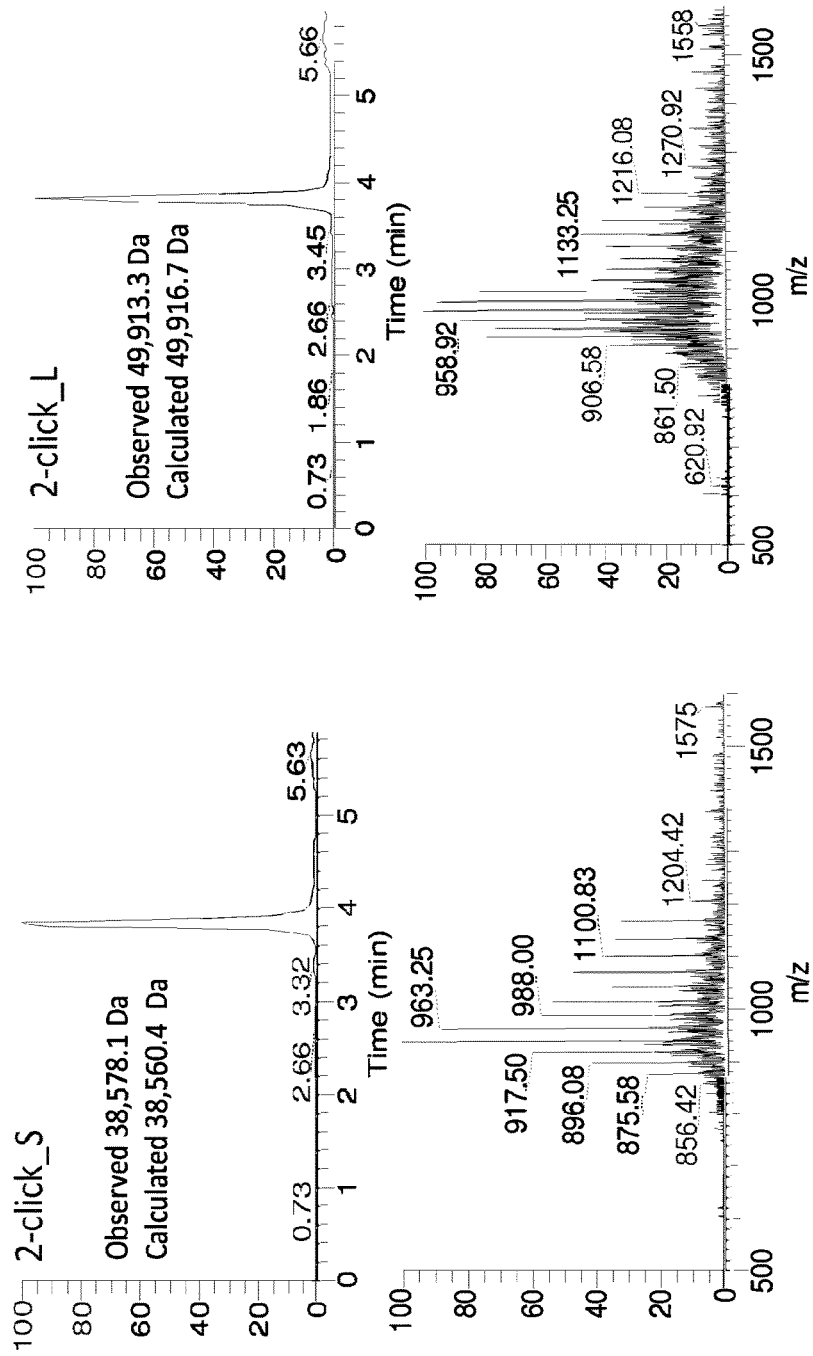

Figure 41

SEQUENCE LISTING

```
<160> NUMBER OF SEQ ID NOS: 70

<210> SEQ ID NO 1
<211> LENGTH: 7
<212> TYPE: DNA
<213> ORGANISM: Artificial Sequence
<220> FEATURE:
<223> OTHER INFORMATION: Synthetic Construct

<400> SEQUENCE: 1 gtgctgc                                                               7

<210> SEQ ID NO 2
<211> LENGTH: 9
<212> TYPE: DNA
<213> ORGANISM: Artificial Sequence
<220> FEATURE:
<223> OTHER INFORMATION: Synthetic Construct

<400> SEQUENCE: 2 gcagcaccc                                                             9

<210> SEQ ID NO 3
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Gly is N-alpha-benzyloxycarbonyl modified
<220> FEATURE:
<221> NAME/KEY: MOD_RES
<222> LOCATION: (6)..(6)
<223> OTHER INFORMATION: Gly is OSU (N-succinimidyl ester) modified

<400> SEQUENCE: 3

Gly Gly Gly Gly Gly Gly
1               5

<210> SEQ ID NO 4
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is azidohomoalanine
<220> FEATURE:
```

```
<221> NAME/KEY: MOD_RES
<222> LOCATION: (4)..(4)
<223> OTHER INFORMATION: Gly is OSu (N-succinimidyl ester) modified

<400> SEQUENCE: 4

Xaa Gly Gly Gly
1

<210> SEQ ID NO 5
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is propargylglycine
<220> FEATURE:
<221> NAME/KEY: MOD_RES
<222> LOCATION: (4)..(4)
<223> OTHER INFORMATION: Gly is Osu (N-succinimidyl ester) modified

<400> SEQUENCE: 5

Xaa Gly Gly Gly
1

<210> SEQ ID NO 6
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Gly is N-alpha-benzyloxycarbonyl modified
<220> FEATURE:
<221> NAME/KEY: MOD_RES
<222> LOCATION: (3)..(3)
<223> OTHER INFORMATION: Gly is OSu  (N-succinimidyl ester) modified

<400> SEQUENCE: 6

Gly Gly Gly
1

<210> SEQ ID NO 7
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: n is Cyanovinylcarbozole (CNVK)
<220> FEATURE:
<221> NAME/KEY: misc_feature
<222> LOCATION: (12)..(12)
<223> OTHER INFORMATION: n is Cyanovinylcarbozole (CNVK)

<400> SEQUENCE: 7
cgancgtgtc ancg                                                        14

<210> SEQ ID NO 8
<211> LENGTH: 53
<212> TYPE: DNA
<213> ORGANISM: Artificial Sequence
<220> FEATURE:
<223> OTHER INFORMATION: Synthetic Construct
```

<400> SEQUENCE: 8
aaaaaagtcg tgacacgtcg gaaaaaaaaa aaacggtgac acggtcgaaa aaa    53

<210> SEQ ID NO 9
<211> LENGTH: 54
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (54)..(54)
<223> OTHER INFORMATION: g is 3'-azide (WHS esther) modified

<400> SEQUENCE: 9
tgcggtctaa ctgtctaggc acttgttcgt ttgccagtgt gaggaatgaa cagg    54

<210> SEQ ID NO 10
<211> LENGTH: 66
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: t is 5'-hexynyl modified

<400> SEQUENCE: 10
taccgaattg ccttcctcgt acagttctaa ggcgcttgga caccacttca atcgggtgct    60
atgctt    66

<210> SEQ ID NO 11
<211> LENGTH: 17
<212> TYPE: DNA
<213> ORGANISM: Artificial Sequence
<220> FEATURE:
<223> OTHER INFORMATION: Synthetic Construct

<400> SEQUENCE: 11
tgcggtctaa ctgtcta    17

<210> SEQ ID NO 12
<211> LENGTH: 17
<212> TYPE: DNA
<213> ORGANISM: Artificial Sequence
<220> FEATURE:
<223> OTHER INFORMATION: Synthetic Construct

<400> SEQUENCE: 12
aagcatagca cccgatt    17

<210> SEQ ID NO 13
<211> LENGTH: 24
<212> TYPE: DNA
<213> ORGANISM: Artificial Sequence
<220> FEATURE:
<223> OTHER INFORMATION: Synthetic Construct

<400> SEQUENCE: 13
ggcaattcgg tacctgttca ttcc    24

<210> SEQ ID NO 14
<211> LENGTH: 12
<212> TYPE: DNA
<213> ORGANISM: Artificial Sequence

```
<220> FEATURE:
<223> OTHER INFORMATION: Synthetic Construct

<400> SEQUENCE: 14
ggaatgaaca gg                                                              12

<210> SEQ ID NO 15
<211> LENGTH: 42
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (42)..(42)
<223> OTHER INFORMATION: g is 3'-azide (WHS Esther) modified

<400> SEQUENCE: 15
tgcggtctaa ctgtctagtt caccttctcc ggaatgaaca gg                              42

<210> SEQ ID NO 16
<211> LENGTH: 42
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: g is 5'-Hexynyl modified

<400> SEQUENCE: 16
ggaatgaaca gggcctgatt gaagcaatcg ggtgctatgc tt                              42

<210> SEQ ID NO 17
<211> LENGTH: 66
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (66)..(66)
<223> OTHER INFORMATION: g is 3'-azide (WHS Ester) modified

<400> SEQUENCE: 17
tgcggtctaa ctgtctaggc acttgttcgt ttgccagtgt gatggacacc acttggaatg          60
aacagg                                                                     66

<210> SEQ ID NO 18
<211> LENGTH: 66
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: g is 5'-Hexynyl modified

<400> SEQUENCE: 18
ggaatgaaca ggggaatgaa caggttcctc gtacagttct aaggcgctca atcgggtgct          60
atgctt                                                                     66

<210> SEQ ID NO 19
<211> LENGTH: 17
<212> TYPE: DNA
```

```
<213> ORGANISM: Artificial Sequence
<220> FEATURE:
<223> OTHER INFORMATION: Synthetic Construct

<400> SEQUENCE: 19
tgcggtctaa ctgtcta                                                  17

<210> SEQ ID NO 20
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: g is 5'-Hexynyl modified
<220> FEATURE:
<221> NAME/KEY: modified_base
<222> LOCATION: (36)..(36)
<223> OTHER INFORMATION: g is 3'-azide (WHS Ester) modified

<400> SEQUENCE: 20
ggaatgaaca gggtaagctg gagtgaaggc gttatg                             36

<210> SEQ ID NO 21
<211> LENGTH: 42
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: g is 5'-dibenzo-cyclooctyne modified

<400> SEQUENCE: 21
gaaggcgtta tgtccgtact cttgcaatcg ggtgctatgc tt                      42

<210> SEQ ID NO 22
<211> LENGTH: 54
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: g is 5'-dibenzo-cyclooctyne modified

<400> SEQUENCE: 22
gaaggcgtta tgtgatatcc gtggtgtcgt gagttccaat cgggtgctat gctt         54

<210> SEQ ID NO 23
<211> LENGTH: 18
<212> TYPE: DNA
<213> ORGANISM: Artificial Sequence
<220> FEATURE:
<223> OTHER INFORMATION: Synthetic Construct

<400> SEQUENCE: 23
aaaaaaaaaa gtcgtgac                                                 18

<210> SEQ ID NO 24
<211> LENGTH: 19
<212> TYPE: DNA
<213> ORGANISM: Artificial Sequence
<220> FEATURE:
<223> OTHER INFORMATION: Synthetic Construct
```

<400> SEQUENCE: 24
acgtcggtaa aaaaaaaa                                                          19

<210> SEQ ID NO 25
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: Cyanovinylcarbozole (CNVK)
<220> FEATURE:
<221> NAME/KEY: misc_feature
<222> LOCATION: (1)..(1)
<223> OTHER INFORMATION: n is Cyanovinylcarbozole (CNVK)
<220> FEATURE:
<221> NAME/KEY: misc_feature
<222> LOCATION: (15)..(15)
<223> OTHER INFORMATION: Cyanovinylcarbozole (CNVK)

<400> SEQUENCE: 25
ncgacgtgtc acgan                                                             15

<210> SEQ ID NO 26
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: t is 5' Psoralen (C2-linked) modified

<400> SEQUENCE: 26
tagcggatgc aaaaaaaaag gcgagcttgc gtactg                                      36

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27
aaaaaaaaag catccgctct                                                        20

<210> SEQ ID NO 28
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: g is 5' Psoralen (C2-linked) modified

<400> SEQUENCE: 28
gagcggatgc aaaaaaaaag gcgagcttgc gtactg                                      36

<210> SEQ ID NO 29
<211> LENGTH: 15
<212> TYPE: DNA
<213> ORGANISM: Artificial Sequence
<220> FEATURE:

-continued

<223> OTHER INFORMATION: Synthetic Construct

<400> SEQUENCE: 29
tccgctcgac ctgag                                                    15

<210> SEQ ID NO 30
<211> LENGTH: 12
<212> TYPE: DNA
<213> ORGANISM: Artificial Sequence
<220> FEATURE:
<223> OTHER INFORMATION: Synthetic Construct

<400> SEQUENCE: 30
aaaaactcag gt                                                       12

<210> SEQ ID NO 31
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: a is 5' biotin modified

<400> SEQUENCE: 31
aaaaactcag gt                                                       12

<210> SEQ ID NO 32
<211> LENGTH: 13
<212> TYPE: DNA
<213> ORGANISM: Artificial Sequence
<220> FEATURE:
<223> OTHER INFORMATION: Synthetic Construct

<400> SEQUENCE: 32
gaaggcgtta tag                                                      13

<210> SEQ ID NO 33
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: a is 56-FAM-Phosphoramidite modified

<400> SEQUENCE: 33
agtacgcaag ctcgc                                                    15

<210> SEQ ID NO 34
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: t is monophosphate modified

<400> SEQUENCE: 34
tccgctcgac ctgag                                                    15

-continued

```
<210> SEQ ID NO 35
<211> LENGTH: 15
<212> TYPE: DNA
<213> ORGANISM: Artificial Sequence
<220> FEATURE:
<223> OTHER INFORMATION: Synthetic Construct

<400> SEQUENCE: 35
tccgctcaac ctgag                                                          15

<210> SEQ ID NO 36
<211> LENGTH: 15
<212> TYPE: DNA
<213> ORGANISM: Artificial Sequence
<220> FEATURE:
<223> OTHER INFORMATION: Synthetic Construct

<400> SEQUENCE: 36
tccgcttaac ctgag                                                          15

<210> SEQ ID NO 37
<211> LENGTH: 37
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is a 5-(Carboxy)vinyl-2'-deoxyuridine

<400> SEQUENCE: 37
ngagcggatg caaaaaaaaa ggcgagcttg cgtactg                                  37

<210> SEQ ID NO 38
<211> LENGTH: 37
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is a 5-(Carboxy)vinyl-2'-deoxyuridine

<400> SEQUENCE: 38
naagcggatg caaaaaaaaa ggcgagcttg cgtactg                                  37

<210> SEQ ID NO 39
<211> LENGTH: 34
<212> TYPE: DNA
<213> ORGANISM: Artificial Sequence
<220> FEATURE:
<223> OTHER INFORMATION: Synthetic Construct

<400> SEQUENCE: 39
aaaaaaaagt cgtgacacgt cggtaaaaaa aaaa                                     34

<210> SEQ ID NO 40
<211> LENGTH: 42
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: t is 5'-Hexyynyl modified
```

```
<400> SEQUENCE: 40
taccgaattg ccgcctgatt gaagcaatcg ggtgctatgc tt                              42

<210> SEQ ID NO 41
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (1)..(1)
<223> OTHER INFORMATION: a is monophospo modified

<400> SEQUENCE: 41
acgtcggtaa aaaaaaaaaa                                                       20

<210> SEQ ID NO 42
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is a, c, g, or t

<400> SEQUENCE: 42
nacgtcggta aaaaaaaaaa a                                                     21

<210> SEQ ID NO 43
<211> LENGTH: 84
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (42)..(42)
<223> OTHER INFORMATION: g is click modified

<400> SEQUENCE: 43
tgcggtctaa ctgtctagtt caccttctcc ggaatgaaca ggtaccgaat tgccgcctga           60
ttgaagcaat cgggtgctat gctt                                                  84

<210> SEQ ID NO 44
<211> LENGTH: 120
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (54)..(54)
<223> OTHER INFORMATION: g is click modified

<400> SEQUENCE: 44
tgcggtctaa ctgtctaggc acttgttcgt ttgccagtgt gaggaatgaa caggtaccga           60
attgccttcc tcgtacagtt ctaaggcgct tggacaccac ttcaatcggg tgctatgctt          120

<210> SEQ ID NO 45
<211> LENGTH: 84
<212> TYPE: DNA
<213> ORGANISM: Artificial Sequence
<220> FEATURE:
<223> OTHER INFORMATION: Synthetic Construct
```

```
<220> FEATURE:
<221> NAME/KEY: modified_base
<222> LOCATION: (42)..(42)
<223> OTHER INFORMATION: g is click modified

<400> SEQUENCE: 45
tgcggtctaa ctgtctagtt caccttctcc ggaatgaaca ggggaatgaa cagggcctga      60
ttgaagcaat cgggtgctat gctt                                            84

<210> SEQ ID NO 46
<211> LENGTH: 132
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (66)..(66)
<223> OTHER INFORMATION: g is click modified

<400> SEQUENCE: 46
tgcggtctaa ctgtctaggc acttgttcgt ttgccagtgt gatggacacc acttggaatg      60
aacaggggaa tgaacagggg aatgaacagg ttcctcgtac agttctaagg cgctcaatcg     120
ggtgctatgc tt                                                         132

<210> SEQ ID NO 47
<211> LENGTH: 120
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (42)..(42)
<223> OTHER INFORMATION: g is click modified
<220> FEATURE:
<221> NAME/KEY: modified_base
<222> LOCATION: (78)..(78)
<223> OTHER INFORMATION: g is dibenzocyclooctyne (DBCO) modified

<400> SEQUENCE: 47
tgcggtctaa ctgtctagtt caccttctcc ggaatgaaca ggggaatgaa cagggtaagc      60
tggagtgaag gcgttatgga aggcgttatg tccgtactct tgcaatcggg tgctatgctt    120

<210> SEQ ID NO 48
<211> LENGTH: 156
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (66)..(66)
<223> OTHER INFORMATION: g is click modified
<220> FEATURE:
<221> NAME/KEY: modified_base
<222> LOCATION: (102)..(102)
<223> OTHER INFORMATION: g is dibenzocyclooctyne (DBCO) modified

<400> SEQUENCE: 48
tgcggtctaa ctgtctaggc acttgttcgt ttgccagtgt gatggacacc acttggaatg      60
aacaggggaa tgaacagggt aagctggagt gaaggcgtta tggaaggcgt tatgtgatat    120
ccgtggtgtc gtgagttcca atcgggtgct atgctt                              156

<210> SEQ ID NO 49
```

<211> LENGTH: 72
<212> TYPE: DNA
<213> ORGANISM: Artificial Sequence
<220> FEATURE:
<223> OTHER INFORMATION: Synthetic Construct

<400> SEQUENCE: 49
aagcatagca cccgattgct tctatcaggc cctgttcatt ccggagaagg tgaactagac    60
agttagaccg ca    72

<210> SEQ ID NO 50
<211> LENGTH: 72
<212> TYPE: DNA
<213> ORGANISM: Artificial Sequence
<220> FEATURE:
<223> OTHER INFORMATION: Synthetic Construct

<400> SEQUENCE: 50
aagcatagca cccgattgct tcaatcaggc cctgttcatt ccggagaagg tgaactagac    60
agttagaccg ca    72

<210> SEQ ID NO 51
<211> LENGTH: 108
<212> TYPE: DNA
<213> ORGANISM: Artificial Sequence
<220> FEATURE:
<223> OTHER INFORMATION: Synthetic Construct

<400> SEQUENCE: 51
aagcatagca cccgattgag cgccttagaa ctgtacgagg aacctgttca ttccaagtgg    60
tgtccatcac actggcaaac gaacaagtgc ctagacagtt agaccgca    108

<210> SEQ ID NO 52
<211> LENGTH: 108
<212> TYPE: DNA
<213> ORGANISM: Artificial Sequence
<220> FEATURE:
<223> OTHER INFORMATION: Synthetic Construct

<400> SEQUENCE: 52
aagcatagca cccgattgag cgccttagaa ctgtacgagg aacctgttca ttccaagtgg    60
tgtccatcac actggcaaac gatcaagtgc ctagacagtt agaccgca    108

<210> SEQ ID NO 53
<211> LENGTH: 108
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (102)..(102)
<223> OTHER INFORMATION: n is a, c, g, or t

<400> SEQUENCE: 53
aagcatagca cccgattgag cgccttagaa ctgtacgagg aacctgttca ttccaagtgg    60
tgtccatcac actggcaaac gaacaagtgc ctagacagtt anaccgca    108

<210> SEQ ID NO 54
<211> LENGTH: 108
<212> TYPE: DNA
<213> ORGANISM: Artificial Sequence
<220> FEATURE:
<223> OTHER INFORMATION: Synthetic Construct

```
<220> FEATURE:
<221> NAME/KEY: misc_feature
<222> LOCATION: (28)..(28)
<223> OTHER INFORMATION: n is a, c, g, or t

<400> SEQUENCE: 54
aagcatagca cccgattgag cgccttanaa ctggaccagg aaccagttcg ttccaagtgg    60
tgtccatcac actggcaaac gaacaagtgc ctagacagtt agaccgca               108

<210> SEQ ID NO 55
<211> LENGTH: 130
<212> TYPE: DNA
<213> ORGANISM: Artificial Sequence
<220> FEATURE:
<223> OTHER INFORMATION: Synthetic Construct

<400> SEQUENCE: 55
aagcatagca cccgattgga actcacgaca ccacggaatc acataacgcc ctcactcccg    60
cttaccctgg tcattccaag tggtggccat acactgtgaa acaaacaagt gcctatacag   120
ttataccgcg                                                          130

<210> SEQ ID NO 56
<211> LENGTH: 134
<212> TYPE: DNA
<213> ORGANISM: Artificial Sequence
<220> FEATURE:
<223> OTHER INFORMATION: Synthetic Construct

<400> SEQUENCE: 56
aagcatagca cccgattgga actcacgaca caccacggat atcacataac gccttcaatc    60
cagcttaccc tgttcattcc aagtggtgtc catcacactg gcaaacgaac aagtgcctag   120
acagttagac cgca                                                     134

<210> SEQ ID NO 57
<211> LENGTH: 131
<212> TYPE: DNA
<213> ORGANISM: Artificial Sequence
<220> FEATURE:
<223> OTHER INFORMATION: Synthetic Construct

<400> SEQUENCE: 57
aagcatagca cccgattgga actcacgaca ccacggatat cacataacgc cttcactcca    60
gcttaccctg ttcttccaag tggtgtccat cacactggca acgaacaag tgcctagaca   120 gttagaccgc a                                                        131

<210> SEQ ID NO 58
<211> LENGTH: 132
<212> TYPE: DNA
<213> ORGANISM: Artificial Sequence
<220> FEATURE:
<223> OTHER INFORMATION: Synthetic Construct

<400> SEQUENCE: 58
aagcatagca cccgattgga actcacgaca ccacggatat cacataacgc cttcactcca    60
gcttaccctg atcattccaa gtggtgtcca tcacactggc aaacgaacaa gtgcctagac   120
agttagaccg ca                                                       132

<210> SEQ ID NO 59
<211> LENGTH: 131
<212> TYPE: DNA
```

```
<213> ORGANISM: Artificial Sequence
<220> FEATURE:
<223> OTHER INFORMATION: Synthetic Construct

<400> SEQUENCE: 59
agcatagcac cgattggaa ctcacgacac cacggatatc acataacgcc ttcactccag      60
cttaccctgt tcattccaag tggtgtccat cacactggca aacgaacaag tgcctagaca    120
gttagaccgc a                                                         131

<210> SEQ ID NO 60
<211> LENGTH: 132
<212> TYPE: DNA
<213> ORGANISM: Artificial Sequence
<220> FEATURE:
<223> OTHER INFORMATION: Synthetic Construct

<400> SEQUENCE: 60
aagcatagca cccgattgga actcacgaaa ccacggatat cacataacgc cttcactcca     60
gcttaccctg ttcattccaa gtggtgtcca tcacactggc aaacgaacaa gtgcctagac    120
agttagaccg ca                                                        132

<210> SEQ ID NO 61
<211> LENGTH: 132
<212> TYPE: DNA
<213> ORGANISM: Artificial Sequence
<220> FEATURE:
<223> OTHER INFORMATION: Synthetic Construct

<400> SEQUENCE: 61
aagcatagca cccgattgga actcacgaca ccacggatat cacataacgc cttcactcca     60
gcttaccctg ttcattccaa gtggtgtcca tcaaactggc aaacgaacaa gtgcctagac    120
agttagaccg ca                                                        132

<210> SEQ ID NO 62
<211> LENGTH: 132
<212> TYPE: DNA
<213> ORGANISM: Artificial Sequence
<220> FEATURE:
<223> OTHER INFORMATION: Synthetic Construct

<400> SEQUENCE: 62
aagcatagca cccgattgga actcacgaca ccacggatat cacataacgc cttcactcca     60
gcttaccctg ttcattccta gtggtgtcca tcacactggc aaacgaacaa gtgcatagac    120
agttagaccg ca                                                        132

<210> SEQ ID NO 63
<211> LENGTH: 131
<212> TYPE: DNA
<213> ORGANISM: Artificial Sequence
<220> FEATURE:
<223> OTHER INFORMATION: Synthetic Construct

<400> SEQUENCE: 63
aagcatagca cccgattgga actcacgaca ccacggatat cacataacgc cttcactcca     60
gcttaccctg ttcattccaa gggtgtccat cacactggca aacgaacaag tgcctagaca    120
gttagaccgc a                                                         131

<210> SEQ ID NO 64
<211> LENGTH: 131
```

```
<212> TYPE: DNA
<213> ORGANISM: Artificial Sequence
<220> FEATURE:
<223> OTHER INFORMATION: Synthetic Construct

<400> SEQUENCE: 64
aagcatagca cccgattgga actcacgaca ccacggatat cacataacgc cttcactcca      60
gcttacctgt tcattccaag tggtgtccat aacactggca aacgaacaag tgcctagaca     120
gttagaccgc a                                                          131

<210> SEQ ID NO 65
<211> LENGTH: 133
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (60)..(60)
<223> OTHER INFORMATION: n is a, c, g, or t

<400> SEQUENCE: 65
aagcatagca cccgattgga actcacgaca ccacggatat cacataacgc cttcactccn      60
ccttaccctg ttcgttccaa gtggtgtcca tcacactggc aaacgatcaa gtgcctacac     120
tgttacagcg cac                                                        133

<210> SEQ ID NO 66
<211> LENGTH: 132
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t

<400> SEQUENCE: 66
tgccatagca cccgattgga actcacgaca ccacggatat cacataacgc cttcactcca      60
gcttacgctg ttcagtcctg gtggtgtccn tcacactggc tgatgaacaa gtgcctaaac     120
ngttgcaccg ca                                                         132

<210> SEQ ID NO 67
<211> LENGTH: 132
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t

<400> SEQUENCE: 67
aagcctagcc accggatgga aatccaggcc cccaggtttt cacctaaagc cttccatccc      60
ggtttccctg ttccttncca aggggttcc tccccatggc caaagaacca ntgcctagac     120
```

```
agttagaccg ca                                                           132

<210> SEQ ID NO 68
<211> LENGTH: 96
<212> TYPE: DNA
<213> ORGANISM: Artificial Sequence
<220> FEATURE:
<223> OTHER INFORMATION: Synthetic Construct

<400> SEQUENCE: 68
aagcatagca cccgattgca agagtacgga cataacgcct tcactccagc ttaccctgtt        60
cattccggag aaggtgaact agacagttag accgca                                 96

<210> SEQ ID NO 69
<211> LENGTH: 95
<212> TYPE: DNA
<213> ORGANISM: Artificial Sequence
<220> FEATURE:
<223> OTHER INFORMATION: Synthetic Construct

<400> SEQUENCE: 69
aagcatagcg cccgattgca agagtacgga cataacgcct tcactccagc ttaccctgtt        60
attccggaga aggtgaacta gacagttaga ccgca                                  95

<210> SEQ ID NO 70
<211> LENGTH: 95
<212> TYPE: DNA
<213> ORGANISM: Artificial Sequence
<220> FEATURE:
<223> OTHER INFORMATION: Synthetic Construct

<400> SEQUENCE: 70
aagcatagca cccgattgca agagtacgga cataacgcct tcactccagc ttaccctgtt        60
cattccgaga aggtgaatta gacagttaga ccgca                                  95
```

DNA-ENCODED LIBRARIES HAVING ENCODING OLIGONUCLEOTIDE LINKAGES NOT READABLE BY POLYMERASES

CROSS-REFERENCE TO RELATED APPLICATIONS

This application claims benefit of U.S. Provisional Application No. 61/671,406, filed Jul. 13, 2012, which is hereby incorporated by reference in its entirety.

REFERENCE TO A SEQUENCE LISTING

This application contains a Sequence Listing in computer readable form. The computer readable form is incorporated herein by reference.

BACKGROUND OF THE INVENTION

In general, this invention relates to DNA-encoded libraries of compounds and methods of using and creating such libraries. The invention also relates to compositions for use in such libraries.

DNA-encoded combinatorial libraries afford many benefits for drug discovery. These libraries can provide a large number of diverse compounds that can be rapidly screened and interrogated. To further increase complexity, various steps of the discovery process can be programmed and automated. These steps include the use of multi-step, split-and-pool synthesis to add building blocks to atomic or polyatomic scaffolds and the use of enzymatic and/or chemical ligation to add oligonucleotide tags that encode both the synthetic steps and the building blocks.

Despite these benefits, numerous issues can arise when very large or complex libraries must be synthesized and deconvoluted. As the size of the library increases, improved methods may be needed to provide high yields of encoding oligonucleotide tag ligation using robust and rapid methodologies. To create libraries under diverse reaction conditions, stable oligonucleotide constructs would be beneficial, such as constructs that are stable under conditions of high pH and elevated temperature. To simplify deconvolution of tags, the sequence of the tags could be recognized by DNA- or RNA-dependent polymerases, such that tag population demographics can be determined by template-dependent polymerization and sequence determination. Difficulties may arise when creating a library having all of these beneficial attributes. Accordingly, there exists a need for improved, more robust methods of screening and identifying small compounds in oligonucleotide-encoded libraries.

SUMMARY OF THE INVENTION

The present invention features complexes for use in DNA-encoded libraries, where these complexes have one or more linkages for which a polymerase has reduced ability to read or translocate through. In order to discover the identity of encoded regions (e.g., headpiece, one or more tags, and/or tailpiece), the linkage is either reversed before it is exposed to the polymerase or alternatively bypassed by the polymerase. This linkage can be bypassed in any useful manner that may not capture all of the sequence information of the tags (e.g., such as in the 5'- or 3'-connectors, as described herein) but captures the encoding sequence information of the tags. Such linkages could result in lower incidences of mis-tagging, expand the number and kind of linkages to be used in making complexes and libraries, and provide non-enzymatic methods for creating and screening DNA-encoded complexes. Additional advantages of these complexes and methods are described herein.

Accordingly, in one aspect, the invention features a complex including: a chemical entity including one or more scaffolds or one or more building blocks; a first oligonucleotide tag encoding the identity of at least one of the one or more scaffolds or building blocks; and a headpiece having a first functional group and a second functional group, where the first functional group operatively associates with the chemical entity and the second functional group operatively associates with the first tag via a first linkage for which a polymerase has reduced ability to read or translocate through.

In another aspect, the invention features a complex including: a chemical entity including one or more scaffolds or one or more building blocks; n number of oligonucleotide tags having n−1 linkages, where n is an integer between 1 and about 10, and where each of the linkages is between two adjacent tags and each tag encodes the identity of at least one of the one or more scaffolds or building blocks; and a headpiece having a first functional group operatively associated with the chemical entity and a second functional group operatively associated with at least one of the n number of tags via a first linkage, where a polymerase has reduced ability to read or translocate through at least one of the first linkage and n−1 linkages.

In some embodiments, n is between 1 and 2, 1 and 3, 1 and 4, 1 and 5, 1 and 6, 1 and 7, 1 and 8, 1 and 9, 1 and 10, 1 and 12, 1 and 15, 1 and 18, 1 and 20, 2 and 3, 2 and 4, 2 and 5, 2 and 6, 2 and 7, 2 and 8, 2 and 9, 2 and 10, 2 and 12, 2 and 15, 2 and 18, 2 and 20, 3 and 4, 3 and 5, 3 and 6, 3 and 7, 3 and 8, 3 and 9, 3 and 10, 3 and 12, 3 and 15, 3 and 18, 3 and 20, 4 and 5, 4 and 6, 4 and 7, 4 and 8, 4 and 9, 4 and 10, 4 and 12, 4 and 15, 4 and 18, or 4 and 20.

In some embodiments, the polymerase has reduced ability to read or translocate through at least about 10% (e.g., about 20%, 25%, 30%, 35%, 40%, 45%, 50%, 55%, 60%, 65%, 70%, 75%, 80%, 85%, 90%, 95%, 96%, 97%, 98%, 99%, or even 100%, as compared to control) of the first linkage and n−1 linkages. In particular embodiments, the polymerase has reduced ability to read or translocate through about 10% to about 100% of the first linkage and n−1 linkages (e.g., 20% to 100%, 25% to 100%, 50% to 100%, 75% to 100%, 90% to 100%, 95% to 100%, 10% to 95%, 20% to 95%, 25% to 95%, 50% to 95%, 75% to 95%, 90% to 95%, 10% to 90%, 20% to 90%, 25% to 90%, 50% to 90%, or 75% to 90%, as compared to control (e.g., as compared to a control oligonucleotide lacking the linkage)).

In some embodiments, one or more tags include a 5'-connector at the 5'-terminus of the one or more tags and a 3'-connector at the 3'-terminus of the one or more tags. In particular embodiments, each 5'-connector and/or each 3'-connector includes the same sequence. In other embodiments, each 5'-connector and/or each 3'-connector include a different sequence.

In some embodiments, the first linkage and/or n−1 linkages are at least about 3 angstroms in length (e.g., at least about 5, 8, 10, 15, 20, 30, 35, 40, 50, 60, 65 or 70 angstroms). In some embodiments, the first linkage and/or n−1 linkages are less than about 30 angstroms in length (e.g., less than about 25, 20, 15, or 10 angstroms). In some embodiments, a DNA polymerase and/or an RNA polymerase (e.g., as described herein) has reduced ability to read or translocate through the first linkage and/or n−1 linkages.

In some embodiments, less than about 10% (e.g., about 10%, 15%, 20%, 25%, 30%, 35%, 40%, 45%, 50%, 55%, 60%, 65%, 70%, 75%, 80%, 85%, 90%, or 95%) of the first linkage and n−1 linkages include an enzymatic linkage. In some embodiments, the first linkage and n−1 linkages include between 0% to 90% enzymatic linkages (e.g., about 0% to 40%, 0% to 45%, 0% to 50%, 0% to 55%, 0% to 60%, 0% to 65%, 0% to 70%, 0% to 75%, 0% to 80%, 0% to 85%, 0% to 90%, 0% to 95%, 0% to 96%, 0% to 97%, 0% to 98%, 0% to 99%, 5% to 40%, 5% to 45%, 5% to 50%, 5% to 55%, 5% to 60%, 5% to 65%, 5% to 70%, 5% to 75%, 5% to 80%, 5% to 85%, 5% to 90%, 5% to 95%, 5% to 96%, 5% to 97%, 5% to 98%, 5% to 99%, 10% to 40%, 10% to 45%, 10% to 50%, 10% to 55%, 10% to 60%, 10% to 65%, 10% to 70%, 10% to 75%, 10% to 80%, 10% to 85%, 10% to 90%, 10% to 95%, 10% to 96%, 10% to 97%, 10% to 98%, 10% to 99%, 15% to 40%, 15% to 45%, 15% to 50%, 15% to 55%, 15% to 60%, 15% to 65%, 15% to 70%, 15% to 75%, 15% to 80%, 15% to 85%, 15% to 90%, 15% to 95%, 15% to 96%, 15% to 97%, 15% to 98%, 15% to 99%, 20% to 40%, 20% to 45%, 20% to 50%, 20% to 55%, 20% to 60%, 20% to 65%, 20% to 70%, 20% to 75%, 20% to 80%, 20% to 85%, 20% to 90%, 20% to 95%, 20% to 96%, 20% to 97%, 20% to 98%, or 20% to 99%).

In some embodiments, the first linkage and/or n−1 linkages include a chemical linkage (e.g., a chemical-reactive group, a photo-reactive group, an intercalating moiety, or a cross-linking oligonucleotide). In particular embodiments, at least one (e.g., two, three, four, five, or more) chemical-reactive group, photo-reactive group, or intercalating moiety is present in a 5'-connector at or in proximity to the 5'-terminus of the tag and/or in a 3'-connector at or in proximity to the 3'-terminus of the tag. In other embodiments, the sequence of at least one of the 5'-connector is complementary to the sequence of the adjacent 3'-connector or identical or sufficiently similar to allow for hybridization to a complementary oligonucleotide. In some embodiments, at least 10% (e.g., about 20%, 25%, 30%, 35%, 40%, 45%, 50%, 55%, 60%, 65%, 70%, 75%, 80%, 85%, 90%, 95%, 96%, 97%, 98%, 99%, or even 100%) of the first linkage and/or n−1 linkages are chemical linkages. In other embodiments, about 10% to about 100% of the first linkage and n−1 linkages (e.g., 20% to 100%, 25% to 100%, 50% to 100%, 75% to 100%, 90% to 100%, 95% to 100%, 10% to 95%, 20% to 95%, 25% to 95%, 50% to 95%, 75% to 95%, 90% to 95%, 10% to 90%, 20% to 90%, 25% to 90%, 50% to 90%, or 75% to 90%) are chemical linkages.

In some embodiments, the chemical-reactive group is selected from a pair of an optionally substituted alkynyl group and an optionally substituted azido group; a pair of an optionally substituted diene having a 4 π-electron system and an optionally substituted dienophile or an optionally substituted heterodienophile having a 2 π-electron system; a pair of a nucleophile and a strained heterocyclyl electrophile; a pair of an optionally substituted amino group and an aldehyde or a ketone group; a pair of an optionally substituted amino group and a carboxylic acid group; a pair of an optionally substituted hydrazine and an aldehyde or a ketone group; a pair of an optionally substituted hydroxylamine and an aldehyde or a ketone group; a pair of a nucleophile and an optionally substituted alkyl halide; a platinum complex; an alkylating agent; or a furan-modified nucleotide (e.g, any described herein).

In some embodiments, the photo-reactive group includes an intercalating moiety, a psoralen derivative, an optionally substituted cyanovinylcarbazole group (e.g., a 3-cyanovinylcarbazole group, such as 3-cyanovinylcarbazole-1'-β-deoxyriboside-5'-triphosphate), an optionally substituted vinylcarbazole group (e.g., a amidovinylcarbazole group, a carboxyvinylcarbazole group, or a $C_{2-7}$ alkoxycarbonylvinylcarbazole group, as described herein), an optionally substituted cyanovinyl group, an optionally substituted acrylamide group, an optionally substituted diazirine group, an optionally substituted benzophenone, or an optionally substituted azide group (e.g., any described herein).

In some embodiments, the intercalating moiety is a psoralen derivative (e.g., psoralen, 8-methoxypsoralen, or 4-hydroxymethyl-4,5,8-trimethyl-psoralen (HMT-psoralen)), an alkaloid derivative (e.g., berberine, palmatine, coralyne, sanguinarine (e.g., iminium or alkanolamine forms thereof, or aristololactam-β-D-glucoside), an ethidium cation (e.g., ethidium bromide), an acridine derivative (e.g., proflavine, acriflavine, or amsacrine), an anthracycline derivative (e.g., doxorubicin, epirubicin, daunorubicin (daunomycin), idarubicin, and aclarubicin), or thalidomide.

In some embodiments, the chemical linkage includes the cross-linking oligonucleotide, where the sequence of at least five nucleotides at the 5'-terminus of the cross-linking oligonucleotide is complementary to the sequence of at least five nucleotides at the 3'-terminus of one or more tags or identical or sufficiently similar to allow for hybridization to a complementary oligonucleotide, and where the sequence of at least five nucleotides at the 3'-terminus of the cross-linking oligonucleotide is complementary to the sequence of at least five nucleotides at the 5'-terminus of one or more tags or identical or sufficiently similar to allow for hybridization to a complementary oligonucleotide. In particular embodiments, the 3'-terminus of one or more tags includes a 3'-connector. In particular embodiments, the 5'-terminus of one or more tags includes a 5'-connector.

In some embodiments, the 5'-terminus and/or 3'-terminus of the cross-linking oligonucleotide include a reversible co-reactive group (e.g., a cyanovinylcarbazole group, a cyanovinyl group, an acrylamide group, a thiol group, or a vinyl sulfone group, as described herein).

In some embodiments, the 3'-connector and/or 5'-connector include a reversible co-reactive group (e.g., a cyanovinylcarbazole group, a cyanovinyl group, an acrylamide group, a thiol group, or a vinyl sulfone group, as described herein).

In some embodiments, the chemical entity is operatively associated to the headpiece via a bifunctional spacer (e.g., any described herein). In other embodiments, the chemical entity is covalently attached to the headpiece. In particular embodiments, the headpiece includes an oligonucleotide selected from the group consisting of a double-stranded oligonucleotide, a single-stranded oligonucleotide, or a hairpin oligonucleotide. In some embodiments, the headpiece includes a primer-binding region.

In any of the embodiments described herein, the complex or method further includes one or more first library-identifying tag(s), use tag(s), and/or origin tag(s). In some embodiments, the complex or method includes between 2 to 20 tags (e.g., between 2 to 10 building block or scaffold tags, one first library-identifying tag, one optional use tag, and one origin tag). In some embodiments, the complex or method includes from 5 to 75 nucleotides (e.g., as described herein, such as about 40 or 50 nucleotides).

In any of the embodiments described herein, each of the tags within an individual tag set includes about the same mass.

In any of the embodiments described herein, the complex includes RNA, DNA, modified DNA, and/or modified RNA (e.g., PNA, LNA, GNA, TNA, or a mixture thereof within the same oligonucleotide, as described herein).

In any of the embodiments described herein, the complex or method further includes a tailpiece.

In another aspect, the invention features a library including one or more complexes described herein. In some embodiments, the library includes a plurality of headpieces. In other embodiments, each headpiece of the plurality of headpieces includes an identical sequence region (e.g., a primer-binding region) and a different encoding region (e.g., a first tag that encodes for use of the library, origin of the library, identity of the library, history of the library, a linkage, a spacer, or addition of a first component or an oligonucleotide sequence that facilitates hybridization, amplification, or sequencing technologies). In particular embodiments, the library includes between about $10^2$ to $10^{20}$ complexes (e.g., about $10^2$ to $10^3$, $10^2$ to $10^4$, $10^2$ to $10^5$, $10^2$ to $10^6$, $10^2$ to $10^7$, $10^2$ to $10^8$, $10^2$ to $10^9$, $10^2$ to $10^{10}$, $10^2$ to $10^{11}$, $10^2$ to $10^{12}$, $10^2$ to $10^{13}$, $10^2$ to $10^{14}$, $10^2$ to $10^{15}$, $10^2$ to $10^{16}$, $10^2$ to $10^{17}$, $10^2$ to $10^{18}$, $10^2$ to $10^{19}$, $10^4$ to $10^5$, $10^4$ to $10^6$, $10^4$ to $10^7$, $10^4$ to $10^8$, $10^4$ to $10^9$, $10^4$ to $10^{10}$, $10^4$ to $10^{11}$, $10^4$ to $10^{12}$, $10^4$ to $10^{13}$, $10^4$ to $10^{14}$, $10^4$ to $10^{15}$, $10^4$ to $10^{16}$, $10^4$ to $10^{17}$, $10^4$ to $10^{18}$, $10^4$ to $10^{19}$, $10^4$ to $10^{20}$, $10^5$ to $10^6$, $10^5$ to $10^7$, $10^5$ to $10^8$, $10^5$ to $10^9$, $10^5$ to $10^{10}$, $10^5$ to $10^{11}$, $10^5$ to $10^{12}$, $10^5$ to $10^{13}$, $10^5$ to $10^{14}$, $10^5$ to $10^{15}$, $10^5$ to $10^{16}$, $10^5$ to $10^{17}$, $10^5$ to $10^{18}$, $10^5$ to $10^{19}$, or $10^5$ to $10^{20}$ complexes). In some embodiments, each complex is different.

In another aspect, the invention features a method of tagging a first library including an encoded chemical entity, the method including: (a) providing a headpiece having a first functional group and a second functional group (e.g., where the headpiece optionally encodes information); (b) binding the first functional group of the headpiece to a first component of the chemical entity, where the headpiece is directly connected to the first component or the headpiece is indirectly connected to the first component by a bifunctional spacer; and (c) binding the second functional group of the headpiece to a first oligonucleotide tag via a first linkage to form a complex, where a polymerase has reduced ability to read or translocate through the first linkage; where the steps (b) and (c) can be performed in any order and where the first tag encodes for the binding reaction of the step (b), thereby providing a tagged library.

In yet another aspect, the invention features a method of tagging a first library including an encoded chemical entity, the method including: (a) providing a headpiece having a first functional group and a second functional group (e.g., where the headpiece optionally encodes information); (b) binding the first functional group of the headpiece to a first component of the chemical entity, where the headpiece is directly connected to the first component or the headpiece is indirectly connected to the first component by a bifunctional spacer; (c) binding the second functional group of the headpiece to a first oligonucleotide tag via a first linkage; (d) binding $n_c$ number of additional components of the chemical entity, where $n_c$ is an integer between 1 and 10; and (e) binding $n_t$ number of additional oligonucleotide tags having $n_t$ linkages to form a complex, where $n_t$ is an integer between 1 and 10, where each of the linkages is between two adjacent tags and where each tag encodes the identity of at least one of the components; where a polymerase has reduced ability to read or translocate through at least one of the first linkage and $n_t$ linkages; and where the steps (b) and (c) can be performed in any order and where the first tag encodes for the binding reaction of the step (b); where the steps (d) and (e) can be performed in any order and where each additional tag encodes for the binding reaction of each additional component of the step (d), thereby providing a tagged library.

In some embodiments, $n_c$ and $n_t$ are each independently an integer between 1 and 2, 1 and 3, 1 and 4, 1 and 5, 1 and 6, 1 and 7, 1 and 8, 1 and 9, 1 and 10, 1 and 12, 1 and 15, 1 and 18, 1 and 20, 2 and 3, 2 and 4, 2 and 5, 2 and 6, 2 and 7, 2 and 8, 2 and 9, 2 and 10, 2 and 12, 2 and 15, 2 and 18, 2 and 20, 3 and 4, 3 and 5, 3 and 6, 3 and 7, 3 and 8, 3 and 9, 3 and 10, 3 and 12, 3 and 15, 3 and 18, 3 and 20, 4 and 5, 4 and 6, 4 and 7, 4 and 8, 4 and 9, 4 and 10, 4 and 12, 4 and 15, 4 and 18, or 4 and 20.

In some embodiments, the polymerase has reduced ability to read or translocate through at least about 10% of the first linkage and $n_t$ linkages (e.g., about 20%, 25%, 30%, 35%, 40%, 45%, 50%, 55%, 60%, 65%, 70%, 75%, 80%, 85%, 90%, 95%, 96%, 97%, 98%, 99%, or even 100%, as compared to control, of the first linkage and $n_t$ linkages). In particular embodiments, the reduced ability to read or translocate through the first linkage and $n_t$ linkages is between about 10 to about 100% (e.g., 20% to 100%, 25% to 100%, 50% to 100%, 75% to 100%, 90% to 100%, 95% to 100%, 10% to 95%, 20% to 95%, 25% to 95%, 50% to 95%, 75% to 95%, 90% to 95%, 10% to 90%, 20% to 90%, 25% to 90%, 50% to 90%, or 75% to 90%, as compared to control (e.g., as compared to a control oligonucleotide lacking the linkage)).

In some embodiments, the first component and/or additional components include a scaffold or a building block.

In some embodiments, step (b) includes binding the headpiece indirectly to the first component via a bifunctional spacer.

In some embodiments, the methods further include binding a use tag, an origin tag, and/or a first library-identifying tag to the complex. In particular embodiments, the method further includes providing a second library and combining the first library with the second library. In some embodiments, the method further includes binding a tailpiece to the complex.

In some embodiments, the binding step includes a chemical-reactive group, a photo-reactive group, an intercalating moiety, or a cross-linking oligonucleotide (e.g., as described herein for any of the complexes herein). In particular embodiments, the method further includes performing split-and-pool synthesis in one or more steps, separating one or more complexes, and/or purifying one or more complexes.

In any of the methods described herein, the method results in any of the complexes described herein or any of the libraries described herein.

In yet another aspect, the invention features a method of screening a plurality of chemical entities, the method including: (a) contacting a target with any complex described herein and/or a library described herein; and (b) selecting one or more complexes having a predetermined characteristic for the target, as compared to a control, thereby screening the chemical entity.

In some embodiments, the predetermined characteristic includes increased binding for the target (e.g., a biological target, as described herein), as compared to a control.

In some embodiments, prior to step (a) one or more operations are performed selected from the list consisting of: annealing one or more relay primers with said complex, wherein said one or more relay primers span said first linkage and/or n−1 linkages; extending said relay primers using a polymerase to produce oligonucleotide fragments; and ligating said oligonucleotide fragments to produce a template.

In another aspect, the invention features a method of determining the nucleotide sequence of any complex described herein, the method including: (a) annealing one or more relay primers with the complex, where the one or more relay primers span the first linkage and/or n−1 linkages; (b) extending the relay primers using a polymerase to produce oligonucleotide fragments; (c) ligating the oligonucleotide fragments to produce a template; (d) optionally amplifying the template by polymerase chain reaction to produce an amplified mix; and (e) sequencing the optionally amplified mix to determine the sequence of the complex.

In some embodiments, the complex includes a 5'-connector at the 5'-terminus of one or more tags and a 3'-connector at the 3'-terminus of one or more tags, and where each of the one or more relay primers hybridizes to adjacent 5'- and 3'-connectors. In particular embodiments, each 5'-connector includes the same sequence, and/or each 3'-connector includes the same sequence. In some embodiments, the sequence of at least one of the 5'-connector is complementary to the sequence of the adjacent 3'-connector (e.g., to form a duplex between the 5'- and 3'-connectors under hybridization conditions) or identical or sufficiently similar to allow for hybridization to a complementary oligonucleotide. In further embodiments, the method includes hybridizing the 5'-connector to the adjacent 3'-connector. In some embodiments, each relay primer for a specific junction (e.g., thereby forming a three-helix junction) between the 5'- and 3'-connectors includes the same sequence.

In another aspect, the invention features a method of determining the nucleotide sequence of any complex described herein, the method including: (a) providing the complex including the chemical linkage, where the chemical linkage is a cross-linking oligonucleotide that spans the junction between two adjacent tags and that operatively associates with the two adjacent tags via one or more reversible co-reactive groups; (b) releasing the cross-linking oligonucleotide (e.g., any described herein) to produce a template; (c) optionally amplifying the template by polymerase chain reaction to produce an amplified mix; and (d) sequencing the optionally amplified mix to determine the sequence of the complex. In some embodiments, a portion of the cross-linking oligonucleotide hybridizes to the termini of two adjacent tags, thereby producing a nick or a gap between the two adjacent tags.

In further embodiments, the method includes ligating the tags using a chemical process or an enzymatic process (e.g., 5'-phosphorylation) prior to step (b).

In some embodiments, the method further includes repairing the template prior to the optional amplifying step or the sequencing step. In particular embodiments, the repairing step includes modifying at least one of the first linkage and/or n−1 linkages to be a repaired linkage capable of being read or translocated through by a polymerase. In some embodiments, the polymerase can read or translocate through at least 50% (e.g., at least 60%, 65%, 70%, 75%, 80%, 85%, 90%, 95%, 96%, 97%, 98%, 99%, or even 100%) of the repaired linkages (e.g., as compared to a control, such as a control oligonucleotide having the first linkage and n−1 linkages that have not been repaired). In particular embodiments, the polymerase can read or translocate through about 10% to about 100% of the repaired linkages (e.g., 20% to 100%, 25% to 100%, 50% to 100%, 75% to 100%, 90% to 100%, 95% to 100%, 10% to 95%, 20% to 95%, 25% to 95%, 50% to 95%, 75% to 95%, 10% to 90%, 20% to 90%, 25% to 90%, 50% to 90%, and 75% to 90%, as compared to control (e.g., as compared to a control oligonucleotide having the first linkage and n−1 linkages that have not been repaired)). In particular embodiments, the repairing step includes providing the template with a repair enzyme (e.g., a photolyase, a glycosylase, an endonuclease, a Flap endonuclease, an apurinic/apyrimidinic (AP) endonuclease, a poly ADP ribose polymerase, or a methyltransferase, as described herein).

In any of the above embodiments, the methods or complexes may include only single-stranded molecules, where the headpiece, the first tag, and/or the one or more additional tags are single-stranded.

In any of the above embodiments, the method further comprises one or more optional steps to diversify the library or to interrogate the members of the library, as described herein. In some embodiments, the method further comprises identifying a small drug-like library member that binds or inactivates a protein of therapeutic interest. In other embodiments, the method further comprises contacting a member of the library with a biological target under conditions suitable for at least one member of the library to bind to the target, removing one or more library members that do not bind to the target, and analyzing the one or more oligonucleotide tags associated with the target.

As described herein, the use of single-stranded molecules could have numerous benefits. Accordingly, in any of the embodiments described herein, the methods and complexes include a headpiece, one or more tags, a complex, a chemical entity, a molecule, or any member of a tagged library having decreased mass, increased solubility (e.g., in an organic solvent), decreased cost, increased reactivity, increased target accessibility, decreased hydrodynamic radius, and/or increased accuracy of analytical assessments, as compared to a method including one or more double-stranded molecules (e.g., a double-stranded headpiece or a double-stranded tag). In some embodiments, each of the tags within a set of tags (e.g., the first tag or a subsequent tag, if present) has about the same mass (e.g., each tag has a mass that is about +/−10% from the average mass between two or more tags). In particular embodiments, the tag has a decreased mass (e.g., less than about 15,000 Daltons, about 14,000 Daltons, about 13,000 Daltons, about 12,000 Daltons, about 11,000 Daltons, about 10,000 Daltons, about 9,000 Daltons, about 8,000 Daltons, about 7,500 Daltons, about 7,000 Daltons, about 6,000 Daltons, about 6,500 Daltons, about 5,000 Daltons, about 5,500 Daltons, about 4,000 Daltons, about 4,500 Daltons, or about 3,000 Daltons) compared to a double-stranded tag (e.g., a double-stranded tag having a mass of about 15,000 Daltons, about 14,000 Daltons, about 13,000 Daltons, or about 12,000 Daltons). In other embodiments, the tag has a reduced length compared to a double-stranded tag (e.g., a double-stranded tag having a length of less than about 20 nucleotides, less than about 19 nucleotides, less than about 18 nucleotides, less than about 17 nucleotides, less than about 16 nucleotides, less than about 15 nucleotides, less than about 14 nucleotides, less than about 13 nucleotides, less than about 12 nucleotides, less than about 11 nucleotides, less than about 10 nucleotides, less than about 9 nucleotides, less than about 8 nucleotides, or less than about 7 nucleotides). In some embodiments, one or more tags or members of the library lack a primer-binding region and/or a constant region (e.g., during a selection step, such as selection using size exclusion chromatography). In some embodiments, one or more tags or members of the library have a reduced constant region (e.g., a length less than about 30 nucleotides, less than about 25 nucleotides, less than about 20 nucleotides, less than about 19 nucleotides, less than about 18 nucleotides, less than about 17 nucleotides, less than about 16 nucleotides, less than about 15 nucleotides, less than about 14 nucleotides, less than about 13 nucleotides, less than about 12 nucleotides, less than about 11 nucleotides, less than about 10 nucleotides, less than about 9 nucleotides, less than about 8 nucleotides, or less than about 7 nucleotides). In other embodiments, the methods include a headpiece that encodes for a molecule, a portion of a chemical entity, a binding reaction (e.g., chemical or enzymatic ligation) of a step, or the identity of a library, where the encoding headpiece eliminates the need of an additional tag to encode such information.

In any of the above embodiments, an oligonucleotide (e.g., the headpiece, the first tag, and/or one or more additional tags, if present) encodes for the identity of the library. In some embodiments, the oligonucleotide (e.g., the headpiece, the first tag, and/or one or more additional tags, if present) includes a first library-identifying sequence, where the sequence encodes for the identity of the first library. In particular embodiments, the oligonucleotide is a first library-identifying tag. In some embodiments, the method includes providing a first library-identifying tag, where the tag includes a sequence that encodes for a first library, and/or binding the first library-identifying tag to the complex. In some embodiments, the method includes providing a second library and combining the first library with a second library. In further embodiments, the method includes providing a second library-identifying tag, where the tag includes a sequence that encodes for a second library. In some embodiments, more than two libraries are combined (e.g., three, four, five, six, seven, eight, nine, ten, or more libraries).

In any of the above embodiments, the encoded information is provided in one or more tags or in a combination of more than one tag. In some embodiments, the encoded information is represented by more than one tag (e.g., two, three, four, five, six, seven, eight, nine, ten, or more tags). In some embodiments, the encoded information is represented by more than one tag, where all encoding tags are contained within the encoding sequence (e.g., by using of a specific tag combination to encode information). In some embodiments, the encoded information is represented by more than one tag, where less than all encoding tags are contained within the encoding sequence (e.g., by using one tag from a set of more than one individual tag to encode within an individual encoding sequence). In some embodiments, the encoded information is represented orthogonally, where encoded information is represented by a combination of more than one tag with less than all of the encoding information being contained within an individual library member, such that more than one corresponding library member needs to be sequenced in order to deconvolute the encoded information. In some embodiments, more than one chemical building block is represented by a single tag (e.g., for a racemic building block, such as two, three, four, five, six, seven, eight, nine, ten, or more building blocks represented by a single tag).

In any of the above embodiments, an oligonucleotide (e.g., a headpiece and/or one or more building blocks) encodes for the use of the member of the library (e.g., use in a selection step or a binding step, as described herein). In some embodiments, the oligonucleotide (e.g., the headpiece, the first tag, and/or one or more additional tags, if present) include a use sequence, where the sequence encodes for use of a subset of members in the library in one or more steps (e.g., a selection step and/or a binding step). In particular embodiments, the oligonucleotide is a use tag including a use sequence. In some embodiments, an oligonucleotide (e.g., a headpiece and/or one or more oligonucleotide tags) encodes for the origin of the member of the library (e.g., in a particular part of the library). In some embodiments, the oligonucleotide (e.g., the headpiece, the first tag, and/or one or more additional tags, if present) includes an origin sequence (e.g., a random or degenerate sequence having a length of about 10, 9, 8, 7, or 6 nucleotides), where the sequence encodes for the origin of the member in the library, as compared to other members of the library. In particular embodiments, the oligonucleotide is an origin tag including an origin sequence. In some embodiments, the method further includes joining, binding, or operatively associating a use tag and/or an origin tag to the complex.

In any of the embodiments herein, the methods, compositions, and complexes optionally include a tailpiece, where the tailpiece includes one or more of a library-identifying sequence, a use sequence, or an origin sequence, as described herein. In particular embodiments, the methods further include joining, binding, or operatively associating the tailpiece (e.g., including one or more of a library-identifying sequence, a use sequence, or an origin sequence) to the complex.

In any of the above embodiments, the methods, compositions, and complexes, or portions thereof (e.g., the headpiece, the first tag, and/or the one or more additional tags, if present), includes a modification that support solubility in semi-, reduced-, or non-aqueous (e.g., organic) conditions. In some embodiments, the bifunctional spacer, headpiece, or one or more tags is modified to increase solubility of a member of said DNA-encoded chemical library in organic conditions In some embodiments, the modification is one or more of an alkyl chain, a polyethylene glycol unit, a branched species with positive charges, or a hydrophobic ring structure. In some embodiments, the modification includes one or more modified nucleotides having a hydrophobic moiety (e.g., modified at the C5 positions of T or C bases with aliphatic chains, such as in 5'-dimethoxytrityl-N4-diisobutylaminomethylidene-5-(1-propynyl)-2'-deoxycytidine, 3'-[(2-cyanoethyl)-(N,N-diisopropyl)]-phosphoramidite; 5'-dimethoxytrityl-5-(1-propynyl)-2'-deoxyuridine, 3'-[(2-cyanoethyl)-(N,N-diisopropyl)]-phosphoramidite; 5'-dimethoxytrityl-5-fluoro-2'-deoxyuridine, 3'-[(2-cyanoethyl)-(N,N-diisopropyl)]-phosphoramidite; and 5'-dimethoxytrityl-5-(pyren-1-yl-ethynyl)-2'-deoxyuridine, or 3'-[(2-cyanoethyl)-(N,N-diisopropyl)]-phosphoramidite) or an insertion having a hydrophobic moiety (e.g., an azobenzene). In some embodiments, the member of the library has an octanol:water coefficient from about 1.0 to about 2.5 (e.g., about 1.0 to about 1.5, about 1.0 to about 2.0, about 1.3 to about 1.5, about 1.3 to about 2.0, about 1.3 to about 2.5, about 1.5 to about 2.0, about 1.5 to about 2.5, or about 2.0 to about 2.5).

In any of the above embodiments, the headpiece, the tailpiece, the first tag, the one or more additional tags, the library-identifying tag, the use tag, and/or the origin tag, if present, may include from about 5 to about 75 nucleotides (e.g., from 5 to 7 nucleotides, from 5 to 8 nucleotides, from 5 to 9 nucleotides, from 5 to 10 nucleotides, from 5 to 11 nucleotides, from 5 to 12 nucleotides, from 5 to 13 nucleotides, from 5 to 14 nucleotides, from 5 to 15 nucleotides, from 5 to 16 nucleotides, from 5 to 17 nucleotides, from 5 to 18 nucleotides, from 5 to 19 nucleotides, from 5 to 20 nucleotides, from 5 to 30 nucleotides, from 5 to 40 nucleotides, from 5 to 50 nucleotides, from 5 to 60 nucleotides, from 5 to 70 nucleotides, from 6 to 7 nucleotides, from 6 to 8 nucleotides, from 6 to 9 nucleotides, from 6 to 10 nucleotides, from 6 to 11 nucleotides, from 6 to 12 nucleotides, from 6 to 13 nucleotides, from 6 to 14 nucleotides, from 6 to 15 nucleotides, from 6 to 16 nucleotides, from 6 to 17 nucleotides, from 6 to 18 nucleotides, from 6 to 19 nucleotides, from 6 to 20 nucleotides, from 7 to 8 nucleotides, from 7 to 9 nucleotides, from 7 to 10 nucleotides, from 7 to 11 nucleotides, from 7 to 12 nucleotides, from 7 to 13 nucleotides, from 7 to 14 nucleotides, from 7 to 15 nucleotides, from 7 to 16 nucleotides, from 7 to 17 nucleotides, from 7 to 18 nucleotides, from 7 to 19 nucleotides, from 7 to 20 nucleotides, from 8 to 9 nucleotides, from 8 to 10 nucleotides, from 8 to 11 nucleotides, from 8 to 12 nucleotides, from 8 to 13 nucleotides, from 8 to 14 nucleotides, from 8 to 15 nucleotides, from 8 to 16 nucleotides, from 8 to 17 nucleotides, from 8 to 18 nucleotides, from 8 to 19 nucleotides, from 8 to 20 nucleotides, from 9 to 10 nucleotides, from 9 to 11 nucleotides, from 9 to 12 nucleotides, from 9 to 13 nucleotides, from 9 to 14 nucleotides, from 9 to 15 nucleotides, from 9 to 16 nucleotides, from 9 to 17 nucleotides, from 9 to 18 nucleotides, from 9 to 19 nucleotides, from 9 to 20 nucleotides, from 10 to 11 nucleotides, from 10 to 12 nucleotides, from 10 to 13 nucleotides, from 10 to 14 nucleotides, from 10 to 15 nucleotides, from 10 to 16 nucleotides, from 10 to 17 nucleotides, from 10 to 18 nucleotides, from 10 to 19 nucleotides, from 10 to 20 nucleotides, from 10 to 30 nucleotides, from 10 to 40 nucleotides, from 10 to 50 nucleotides, from 10 to 60 nucleotides, from 10 to 70 nucleotides, from 10 to 75 nucleotides, from 11 to 12 nucleotides, from 11 to 13 nucleotides, from 11 to 14 nucleotides, from 11 to 15 nucleotides, from 11 to 16 nucleotides, from 11 to 17 nucleotides, from 11 to 18 nucleotides, from 11 to 19 nucleotides, from 11 to 20 nucleotides, from 12 to 13 nucleotides, from 12 to 14 nucleotides, from 12 to 15 nucleotides, from 12 to 16 nucleotides, from 12 to 17 nucleotides, from 12 to 18 nucleotides, from 12 to 19 nucleotides, from 12 to 20 nucleotides, from 13 to 14 nucleotides, from 13 to 15 nucleotides, from 13 to 16 nucleotides, from 13 to 17 nucleotides, from 13 to 18 nucleotides, from 13 to 19 nucleotides, from 13 to 20 nucleotides, from 14 to 15 nucleotides, from 14 to 16 nucleotides, from 14 to 17 nucleotides, from 14 to 18 nucleotides, from 14 to 19 nucleotides, from 14 to 20 nucleotides, from 15 to 16 nucleotides, from 15 to 17 nucleotides, from 15 to 18 nucleotides, from 15 to 19 nucleotides, from 15 to 20 nucleotides, from 16 to 17 nucleotides, from 16 to 18 nucleotides, from 16 to 19 nucleotides, from 16 to 20 nucleotides, from 17 to 18 nucleotides, from 17 to 19 nucleotides, from 17 to 20 nucleotides, from 18 to 19 nucleotides, from 18 to 20 nucleotides, from 19 to 20 nucleotides, from 20 to 30 nucleotides, from 20 to 40 nucleotides, from 20 to 50 nucleotides, from 20 to 60 nucleotides, from 20 to 70 nucleotides, from 20 to 75 nucleotides, from 30 to 40 nucleotides, from 30 to 50 nucleotides, from 30 to 60 nucleotides, from 30 to 70 nucleotides, from 30 to 75 nucleotides, from 40 to 50 nucleotides, from 40 to 60 nucleotides, from 40 to 70 nucleotides, from 40 to 75 nucleotides, from 50 to 60 nucleotides, from 50 to 70 nucleotides, from 50 to 75 nucleotides, from 60 to 70 nucleotides, from 60 to 75 nucleotides, and from 70 to 75 nucleotides). In particular embodiments, the headpiece, the first tag, the second tag, the one or more additional tags, the library-identifying tag, the use tag, and/or the origin tag, if present, have a length of less than 20 nucleotides (e.g., less than 19 nucleotides, less than 18 nucleotides, less than 17 nucleotides, less than 16 nucleotides, less than 15 nucleotides, less than 14 nucleotides, less than 13 nucleotides, less than 12 nucleotides, less than 11 nucleotides, less than 10 nucleotides, less than 9 nucleotides, less than 8 nucleotides, or less than 7 nucleotides).

In any of the above embodiments, the encoding sequence (e.g., the headpiece, the tailpiece, the first tag, the one or more additional tags, the library-identifying tag, the use tag, and/or the origin tag, if present) may include more than 20 nucleotides (e.g., more than 25, 30 35, 40, 45, 50, 55, 60, 65, 70, or 75 nucleotides).

Definitions

By "2'-substituted nucleotide" is meant a nucleotide base having a substitution at the 2'-position of ribose.

By "about" is meant +/−10% of the recited value.

By "bifunctional" is meant having two reactive groups that allow for binding of two chemical moieties.

By "bifunctional spacer" is meant a spacing moiety having two reactive groups that allow for binding of a chemical entity and the encoding information of the complex. In one non-limiting example, the bifunctional spacer is provided between the chemical entity and a tag. In another non-limiting example, the bifunctional spacer is provided between the chemical entity and a headpiece. Exemplary bifunctional spacers are provided herein.

By "binding" is meant attaching by a covalent bond or a non-covalent bond. Non-covalent bonds include those formed by van der Waals forces, hydrogen bonds, ionic bonds, entrapment or physical encapsulation, absorption, adsorption, and/or other intermolecular forces. Binding can be effectuated by any useful means, such as by enzymatic binding (e.g., enzymatic ligation to provide an enzymatic linkage) or by chemical binding (e.g., chemical ligation to provide a chemical linkage).

By "building block" is meant a structural unit of a chemical entity, where the unit is directly linked to other chemical structural units or indirectly linked through the scaffold. When the chemical entity is polymeric or oligomeric, the building blocks are the monomeric units of the polymer or oligomer. Building blocks can have one or more diversity nodes that allow for the addition of one or more other building blocks or scaffolds. In most cases, each diversity node is a functional group capable of reacting with one or more building blocks or scaffolds to form a chemical entity. Generally, the building blocks have at least two diversity nodes (or reactive functional groups), but some building blocks may have one diversity node (or reactive functional group). Alternatively, the encoded chemical or binding steps may include several chemical components (e.g., multi-component condensation reactions or multi-step processes). Reactive groups on two different building blocks should be complementary, i.e., capable of reacting together to form a covalent or a non-covalent bond.

By "chemical entity" is meant a compound comprising one or more building blocks and optionally one or more scaffolds. The chemical entity can be any small molecule or peptide drug or drug candidate designed or built to have one or more desired characteristics, e.g., capacity to bind a biological target, solubility, availability of hydrogen bond donors and acceptors, rotational degrees of freedom of the bonds, positive charge, negative charge, and the like. In certain embodiments, the chemical entity can be reacted further as a bifunctional or trifunctional (or greater) entity.

By "chemical-reactive group" is meant a reactive group that participates in a modular reaction, thus producing a linkage. Exemplary reactions and reactive groups include those selected from a Huisgen 1,3-dipolar cycloaddition reaction with a pair of an optionally substituted alkynyl group and an optionally substituted azido group; a Diels-Alder reaction with a pair of an optionally substituted diene having a 4 π-electron system and an optionally substituted dienophile or an optionally substituted heterodienophile having a 2 π-electron system; a ring opening reaction with a nucleophile and a strained heterocyclyl electrophile; a splint ligation reaction with a phosphorothioate group and an iodo group; and a reductive amination reaction with an aldehyde group and an amino group, as described herein.

By "complementary" is meant a sequence capable of hybridizing, as defined herein, to form secondary structure (a duplex or a double-stranded portion of a nucleic acid molecule). The complementarity need not be perfect but may include one or more mismatches at one, two, three, or more nucleotides. For example, complementary sequence may contain nucleobases that can form hydrogen bonds according to Watson-Crick base-pairing rules (e.g., G with C, A with T or A with U) or other hydrogen bonding motifs (e.g., diaminopurine with T, 5-methyl C with G, 2-thiothymidine with A, inosine with C, pseudoisocytosine with G). The sequence and its complementary sequence can be present in the same oligonucleotide or in different oligonucleotides.

By "complex" or "ligated complex" is meant a headpiece that is operatively associated with a chemical entity and/or one or more oligonucleotide tags by a covalent bond or a non-covalent bond. The complex can optionally include a bifunctional spacer between the chemical entity and the headpiece.

By "component" of a chemical entity is meant either a scaffold or a building block.

By "connector" of an oligonucleotide tag is meant a portion of the tag at or in proximity to the 5'- or 3'-terminus having a fixed sequence. A 5'-connector is located at or in proximity to the 5'-terminus of an oligonucleotide, and a 3'-connector is located at or in proximity to the 3'-terminus of an oligonucleotide. When present in a complex, each 5'-connector may be the same or different, and each 3'-connector may be the same or different. In an exemplary, non-limiting complex having more than one tags, each tag can include a 5'-connector and a 3'-connector, where each 5'-connector has the same sequence and each 3'-connector has the same sequence (e.g., where the sequence of the 5'-connector can be the same or different from the sequence of the 3'-connector). In another exemplary, non-limiting complex, the sequence of the 5'-connector is designed to be complementary, as defined herein, to the sequence of the 3'-connector (e.g., to allow for hybridization between 5'- and 3'-connectors). The connector can optionally include one or more groups allowing for a linkage (e.g., a linkage for which a polymerase has reduced ability to read or translocate through, such as a chemical linkage).

By "constant" or "fixed constant" sequence is meant a sequence of an oligonucleotide that does not encode information. Non-limiting, exemplary portions of a complex having a constant sequence include a primer-binding region, a 5'-connector, or a 3'-connector. The headpiece of the invention can encode information (thus, a tag) or alternatively not encode information (thus, a constant sequence). Similarly, the tailpiece of the invention can encode or not encode information.

By "cross-linking oligonucleotide" is meant an oligonucleotide that operatively associates, as defined herein, at a particular junction between two adjacent tags in a complex. In a non-limiting example, one terminus of the cross-linking oligonucleotide hybridizes to the 3'-connector of a first tag, and the other terminus of the cross-linking oligonucleotide hybridizes to the 5'-connector of a second tag that is adjacent to the first tag. Exemplary, non-limiting embodiments of cross-linking oligonucleotides include those having one or more reactive groups (e.g., a chemical-reactive group, a photo-reactive group, an intercalating moiety, or a reversible co-reactive group, or any described herein) that operatively associates with adjacent tags or connectors of adjacent tags.

By "diversity node" is meant a functional group at a position in the scaffold or the building block that allows for adding another building block.

By "headpiece" is meant a chemical structure for library synthesis that is operatively linked to a component of a chemical entity and to a tag, e.g., a starting oligonucleotide. Optionally a headpiece may contain few or no nucleotides, but may provide a point at which they may be operatively associated. Optionally, a bifunctional spacer connects the headpiece to the component.

By "hybridize" is meant to pair to form a double-stranded molecule between complementary oligonucleotides, or portions thereof, under various conditions of stringency. (See, e.g., Wahl, G. M. and S. L. Berger (1987) Methods Enzymol. 152:399; Kimmel, A. R. (1987) Methods Enzymol. 152: 507.) For example, high stringency hybridization can be obtained with a salt concentration ordinarily less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide or at least about 50% formamide High stringency hybridization temperature conditions will ordinarily include temperatures of at least about 30° C., 37° C., or 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In an alternative embodiment, hybridization will occur at 37° C. in 500 mM NaCl, 50 mM trisodium citrate, 1% SDS, 35% formamide, and 100 µg/ml denatured salmon sperm DNA (ssDNA). In a further alternative embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, high stringency salt concentrations for the wash steps may be, e.g., less than about 30 mM NaCl and 3 mM trisodium citrate, or less than about 15 mM NaCl and 1.5 mM trisodium citrate. High stringency temperature conditions for the wash steps will ordinarily include a temperature of, e.g., at least about 25° C., 42° C., or 68° C. In one embodiment, wash steps will occur at 25° C. in 30 mM NaCl, 3 mM trisodium citrate, and 0.1% SDS. In an alternative embodiment, wash steps will occur at 42° C. in 15 mM NaCl, 1.5 mM trisodium citrate, and 0.1% SDS. In a further alternative embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "intercalating moiety" is meant a reactive group that results in inclusion of a moiety between two or more nucleotides. In a non-limiting example, the intercalating moiety reacts with one or more nucleotides to form inter- or intra-strand cross-links between duplex or triplex oligonucleotides. Exemplary, non-limiting intercalating moieties are described herein.

By "junction" is meant a nick (lack of an internucleotide bond) or a gap (lack of one or more nucleotides) between two adjacent tags in a complex. The junction can also be between two adjacent connectors present in two adjacent tags (e.g., between the 3'-connector of a first tag and the 5'-connector of a second tag that is adjacent to the first tag).

By "library" is meant a collection of molecules or chemical entities. Optionally, the molecules or chemical entities are bound to one or more oligonucleotides that encodes for the molecules or portions of the chemical entity.

By "linkage" is meant a chemical connecting entity that allows for operatively associating two or more chemical structures, where the linkage is present between the headpiece and one or more tags, between two tags, or between a tag and a tailpiece. The chemical connecting entity can be a non-covalent bond (e.g., as described herein), a covalent bond, or a reaction product between two functional groups. By "chemical linkage" is meant a linkage formed by a non-enzymatic, chemical reaction between two functional groups. Exemplary, non-limiting functional groups include a chemical-reactive group, a photo-reactive group, an intercalating moiety, or a cross-linking oligonucleotide (e.g., as described herein). By "enzymatic linkage" is meant an internucleotide or internucleoside linkage formed by an enzyme. Exemplary, non-limiting enzymes include a kinase, a polymerase, a ligase, or combinations thereof. By a linkage "for which a polymerase has reduced ability to read or translocate through" is meant a linkage, when present in an oligonucleotide template, that provides a reduced amount of elongated and/or amplified products by a polymerase, as compared to a control oligonucleotide lacking the linkage. Exemplary, non-limiting methods for determining such a linkage include primer extension as assessed by PCR analysis (e.g., quantitative PCR), RT-PCR analysis, liquid chromatography-mass spectrometry, sequence demographics, or other methods. Exemplary, non-limiting polymerases include DNA polymerases and RNA polymerases, such as DNA polymerase I, DNA polymerase II, DNA polymerase III, DNA polymerase VI, Taq DNA polymerase, Deep VentR™ DNA Polymerase (high-fidelity thermophilic DNA polymerase, available from New England Biolabs), T7 DNA polymerase, T4 DNA polymerase, RNA polymerase I, RNA polymerase II, RNA polymerase III, or T7 RNA polymerase.

By "multivalent cation" is meant a cation capable of forming more than one bond with more than one ligand or anion. The multivalent cation can form either an ionic complex or a coordination complex. Exemplary multivalent cations include those from the alkali earth metals (e.g., magnesium) and transition metals (e.g., manganese (II) or cobalt (III)), and those that are optionally bound to one or more anions and/or one or more univalent or polydentate ligands, such as chloride, amine, and/or ethylenediamine.

By "oligonucleotide" is meant a polymer of nucleotides having a 5'-terminus, a 3'-terminus, and one or more nucleotides at the internal position between the 5'- and 3'-termini. The oligonucleotide may include DNA, RNA, or any derivative thereof known in the art that can be synthesized and used for base-pair recognition. The oligonucleotide does not have to have contiguous bases but can be interspersed with linker moieties. The oligonucleotide polymer and nucleotide (e.g., modified DNA or RNA) may include natural bases (e.g., adenosine, thymidine, guanosine, cytidine, uridine, deoxyadenosine, deoxythymidine, deoxyguanosine, deoxycytidine, inosine, or diamino purine), base analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), modified bases (e.g., 2'-substituted nucleotides, such as 2'-O-methylated bases and 2'-fluoro bases), intercalated bases, modified sugars (e.g., 2'-fluororibose; ribose; 2'-deoxyribose; arabinose; hexose; anhydrohexitol; altritol; mannitol; cyclohexanyl; cyclohexenyl; morpholino that also has a phosphoramidate backbone; locked nucleic acids (LNA, e.g., where the 2'-hydroxyl of the ribose is connected by a $C_{1-6}$ alkylene or $C_{1-6}$ heteroalkylene bridge to the 4'-carbon of the same ribose sugar, where exemplary bridges included methylene, propylene, ether, or amino bridges); glycol nucleic acid (GNA, e.g., R-GNA or S-GNA, where ribose is replaced by glycol units attached to phosphodiester bonds); threose nucleic acid (TNA, where ribose is replace with α-L-threofuranosyl-(3'→2')); and/or replacement of the oxygen in ribose (e.g., with S, Se, or alkylene, such as methylene or ethylene)), modified backbones (e.g., peptide nucleic acid (PNA), where 2-amino-ethyl-glycine linkages replace the ribose and phosphodiester backbone), and/or modified phosphate groups (e.g., phosphorothioates, 5'-N-phosphoramidites, phosphoroselenates, boranophosphates, boranophosphate esters, hydrogen phosphonates, phosphoramidates, phosphorodiamidates, alkyl or aryl phosphonates, phosphotriesters, bridged phosphoramidates, bridged phosphorothioates, and bridged methylene-phosphonates). The oligonucleotide can be single-stranded (e.g., hairpin), double-stranded, or possess other secondary or tertiary structures (e.g., stem-loop structures, double helixes, triplexes, quadruplexes, etc.).

By "operatively linked" or "operatively associated" is meant that two or more chemical structures are directly or indirectly linked together in such a way as to remain linked through the various manipulations they are expected to undergo. Typically, the chemical entity and the headpiece are operatively associated in an indirect manner (e.g., covalently via an appropriate spacer). For example, the spacer may be a bifunctional moiety with a site of attachment for chemical entity and a site of attachment for the headpiece.

By "photo-reactive group" is meant a reactive group that participates in a reaction caused by absorption of ultraviolet, visible, or infrared radiation, thus producing a linkage Exemplary, non-limiting photo-reactive groups are described herein.

By "protecting group" is a meant a group intended to protect the 3'-terminus or 5'-terminus of an oligonucleotide or to protect one or more functional groups of the chemical entity, scaffold, or building block against undesirable reactions during one or more binding steps of making, tagging, or using an oligonucleotide-encoded library. Commonly used protecting groups are disclosed in Greene, "Protective Groups in Organic Synthesis," 4$^{th}$ Edition (John Wiley & Sons, New York, 2007), which is incorporated herein by reference. Exemplary protecting groups for oligonucleotides include irreversible protecting groups, such as dideoxynucleotides and dideoxynucleosides (ddNTP or ddN), and, more preferably, reversible protecting groups for hydroxyl groups, such as ester groups (e.g., O-(α-methoxyethyl)ester, O-isovaleryl ester, and O-levulinyl ester), trityl groups (e.g., dimethoxytrityl and monomethoxytrityl), xanthenyl groups (e.g., 9-phenylxanthen-9-yl and 9-(p-methoxyphenyl)xanthen-9-yl), acyl groups (e.g., phenoxyacetyl and acetyl), and silyl groups (e.g., t-butyldimethylsilyl). Exemplary, non-limiting protecting groups for chemical entities, scaffolds, and building blocks include N-protecting groups to protect an amino group against undesirable reactions during synthetic procedure (e.g., acyl; aryloyl; carbamyl groups, such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries, such as protected or unprotected D, L or D, L-amino acids, such as alanine, leucine, phenylalanine, and the like; sulfonyl-containing groups, such as benzenesulfonyl, p-toluenesulfonyl, and the like; carbamate forming groups, such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5 dimethoxybenzyl oxycarbonyl, 2,4-dimethoxybenzyloxycarbonyl, 4 methoxybenzyloxycarbonyl, 2-nitro-4,5-dimethoxybenzyloxycarbonyl, 3,4,5 trimethoxybenzyloxycarbonyl, 1-(p-biphenylyl)-1-methylethoxycarbonyl, α,α-dimethyl-3,5 dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like; alkaryl groups, such as benzyl, triphenylmethyl, benzyloxymethyl, and the like; and silyl groups such as trimethylsilyl, and the like; where preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz)); O-protecting groups to protect a hydroxyl group against undesirable reactions during synthetic procedure (e.g., alkylcarbonyl groups, such as acyl, acetyl, pivaloyl, and the like; optionally substituted arylcarbonyl groups, such as benzoyl; silyl groups, such as trimethylsilyl (TMS), tert-butyldimethylsilyl (TBDMS), tri-isopropylsilyloxymethyl (TOM), triisopropylsilyl (TIPS), and the like; ether-forming groups with the hydroxyl, such methyl, methoxymethyl, tetrahydropyranyl, benzyl, p-methoxybenzyl, trityl, and the like; alkoxycarbonyls, such as methoxycarbonyl, ethoxycarbonyl, isopropoxycarbonyl, n-isopropoxycarbonyl, n-butyloxycarbonyl, isobutyloxycarbonyl, sec-butyloxycarbonyl, t-butyloxycarbonyl, 2-ethylhexyloxycarbonyl, cyclohexyloxycarbonyl, methyloxycarbonyl, and the like; alkoxyalkoxycarbonyl groups, such as methoxymethoxycarbonyl, ethoxymethoxycarbonyl, 2-methoxyethoxycarbonyl, 2-ethoxyethoxycarbonyl, 2-butoxyethoxycarbonyl, 2-methoxyethoxymethoxycarbonyl, allyloxycarbonyl, propargyloxycarbonyl, 2-butenoxycarbonyl, 3-methyl-2-butenoxycarbonyl, and the like; haloalkoxycarbonyls, such as 2-chloroethoxycarbonyl, 2-chloroethoxycarbonyl, 2,2,2-trichloroethoxycarbonyl, and the like; optionally substituted arylalkoxycarbonyl groups, such as benzyloxycarbonyl, p-methylbenzyloxycarbonyl, p-methoxybenzyloxycarbonyl, p-nitrobenzyloxycarbonyl, 2,4-dinitrobenzyloxycarbonyl, 3,5-dimethylbenzyloxycarbonyl, p-chlorobenzyloxycarbonyl, p-bromobenzyloxycarbonyl, and the like; and optionally substituted aryloxycarbonyl groups, such as phenoxycarbonyl, p-nitrophenoxycarbonyl, o-nitrophenoxycarbonyl, 2,4-dinitrophenoxycarbonyl, p-methyl-phenoxycarbonyl, m-methylphenoxycarbonyl, o-bromophenoxycarbonyl, 3,5-dimethylphenoxycarbonyl, p-chlorophenoxycarbonyl, 2-chloro-4-nitrophenoxy-carbonyl, and the like); carbonyl-protecting groups (e.g., acetal and ketal groups, such as dimethyl acetal, 1,3-dioxolane, and the like; acylal groups; and dithiane groups, such as 1,3-dithianes, 1,3-dithiolane, and the like); carboxylic acid-protecting groups (e.g., ester groups, such as methyl ester, benzyl ester, t-butyl ester, orthoesters, and the like; silyl groups, such as trimethylsilyl, as well as any described herein; and oxazoline groups); and phosphate-protecting groups (e.g., optionally substituted ester groups, such as methyl ester, isopropyl ester, 2-cyanoethyl ester, allyl ester, t-butyl ester, benzyl ester, fluorenylmethyl ester, 2-(trimethylsilyl)ethyl ester, 2-(methylsulfonyl)ethyl ester, 2,2,2-trichloroethyl ester, 3',5'-dimethoxybenzoin ester, p-hydroxyphenacyl ester, and the like).

By "proximity" or "in proximity" to a terminus of an oligonucleotide is meant near or closer to the stated terminus than the other remaining terminus. For example, a moiety or group in proximity to the 3'-terminus of an oligonucleotide is near or closer to the 3'-terminus than the 5'-terminus. In particular embodiments, a moiety or group in proximity to the 3'-terminus of an oligonucleotide is one, two, three, four, five, six, seven, eight, nine, ten, fifteen, or more nucleotides from the 3'-terminus. In other embodiments, a moiety or group in proximity to the 5'-terminus of an oligonucleotide is one, two, three, four, five, six, seven, eight, nine, ten, fifteen, or more nucleotides from the 5'-terminus.

By "purifying" is meant removing any unreacted product or any agent present in a reaction mixture that may reduce the activity of a chemical or biological agent to be used in a successive step. Purifying can include one or more of chromatographic separation, electrophoretic separation, and precipitation of the unreacted product or reagent to be removed.

By "reversible co-reactive group" is meant a reactive group that participates in a reversible reaction. Exemplary, non-limiting reactive groups include photo-reactive groups, where exposure to a particular absorption radiation results in a linkage between the photo-reactive groups and exposure to a different, particular absorption radiation results in cleavage of the formed linkage (e.g., a cyanovinylcarbazole group, a cyanovinyl group, and an acrylamide group). Another exemplary, non-limiting reactive group includes redox-reactive groups, where such groups can be reversibly reduced or oxidized (e.g., a thiol group).

By "scaffold" is meant a chemical moiety that displays one or more diversity nodes in a particular special geometry. Diversity nodes are typically attached to the scaffold during library synthesis, but in some cases one diversity node can be attached to the scaffold prior to library synthesis (e.g., addition of one or more building blocks and/or one or more tags). In some embodiments, the scaffold is derivatized such that it can be orthogonally deprotected during library synthesis and subsequently reacted with different diversity nodes.

By "small molecule" drug or "small molecule" drug candidate is meant a molecule that has a molecular weight below about 1,000 Daltons. Small molecules may be organic or inorganic, isolated (e.g., from compound libraries or natural sources), or obtained by derivatization of known compounds.

By "substantial identity" or "substantially identical" is meant a polypeptide or polynucleotide sequence that has the same polypeptide or polynucleotide sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least 50%, 60%, 70%, 75%, 80%, 85%, 90%, 95%, 96%, 97%, 98%, 99%, or 100% identity to the reference amino acid sequence. For polypeptides, the length of comparison sequences will generally be at least 5, 6, 7, 8, 9, 10, 11, 12, 13, 14, 15, 16, 17, 18, 19, or 20 contiguous amino acids, more preferably at least 25, 50, 75, 90, 100, 150, 200, 250, 300, or 350 contiguous amino acids, and most preferably the full-length amino acid sequence. For nucleic acids, the length of comparison sequences will generally be at least 5 contiguous nucleotides, preferably at least 10, 11, 12, 13, 14, 15, 16, 17, 18, 19, 20, 21, 22, 23, 24, or 25 contiguous nucleotides, and most preferably the full length nucleotide sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

By "tag" or "oligonucleotide tag" is meant an oligonucleotide portion of the library at least part of which encodes information. Non-limiting examples of such information include the addition (e.g., by a binding reaction) of a component (i.e., a scaffold or a building block, as in a scaffold tag or a building block tag, respectively), the headpiece in the library, the identity of the library (i.e., as in an identity tag), the use of the library (i.e., as in a use tag), and/or the origin of a library member (i.e., as in an origin tag).

By "tailpiece" is meant an oligonucleotide portion of the library that is attached to the complex after the addition of all of the preceding tags and encodes for the identity of the library, the use of the library, and/or the origin of a library member.

By "primer" is meant an oligonucleotide that is capable of annealing to an oligonucleotide template and then being extended by a polymerase in a template-dependent manner.

By "relay primer" is meant an oligonucleotide that is capable of annealing to an oligonucleotide template that contains, in the region of the template to which the primer is hybridized, at least one internucleotide linkage that reduces the ability of a polymerase to read or translocate through. Upon hybridization, one or more relay primers allow for extension by a polymerase in a template dependent manner.

By "recombination," as used herein, is meant the generation of a polymerase product as a result of at least two distinct hybridization events.

Other features and advantages of the invention will be apparent from the following Detailed Description and the claims.

BRIEF DESCRIPTION OF THE DRAWINGS

FIG. 1A shows a complex (from the 5' to 3' direction) having a chemical entity (star), a fixed constant sequence (e.g., a headpiece), followed by three variable encoding sequences (e.g., three tags), and another fixed constant sequence (e.g., a tailpiece), where the linkage between the fixed constant sequences and variable encoding sequences are readable. The complex can be further extended using a polymerase with a primer (hybridized to the 3'-terminus of the complex), optionally amplified with PCR, and sequenced. FIG. 1B shows a complex having unreadable linkages. The complex (from the 5' to 3' direction) has a chemical entity (star), a fixed constant sequence (e.g., a headpiece), followed by three variable encoding sequences (e.g., three tags), and another fixed constant sequence (e.g., a tailpiece), where the linkage between the fixed constant sequences and variable encoding sequences are unreadable Each of the variable encoding sequences includes a 5'-connector and a 3'-connector that are fixed constant sequences. Because the linkages are unreadable, relay primers are used to span the linkages and to allow for extension with a polymerase, thus forming oligonucleotide fragments. The fragments are then ligated using ligase, optionally amplified with PCR, and sequenced. The reading process (e.g., optional extension, ligation, optional amplification, and sequencing) may optionally be entirely performed after selection. Alternatively, the optional extension and ligation part of the reading process may be performed prior to selection.

FIG. 7 shows the LCMS of purified CNVK2_P_TagB and CNVK2_TagA.

FIG. 11 shows Oligonucleotide 5PSO2_A9_TA, modified with C2-Psoralen at the 5'-terminus and Oligonucleotide PSO_HP_A9_TCT.

FIG. 31 shows the LCMS of the 2cl_s conjugate.

FIG. 32 shows Conjugate_Click_S and Conjugate_Click_L.

Polymerase and water to 50 uL. The reaction was cycled 21 times as follows: 30 seconds at 94° C., 30 seconds at 52° C. and 60 seconds at 72° C.

Figure 40:
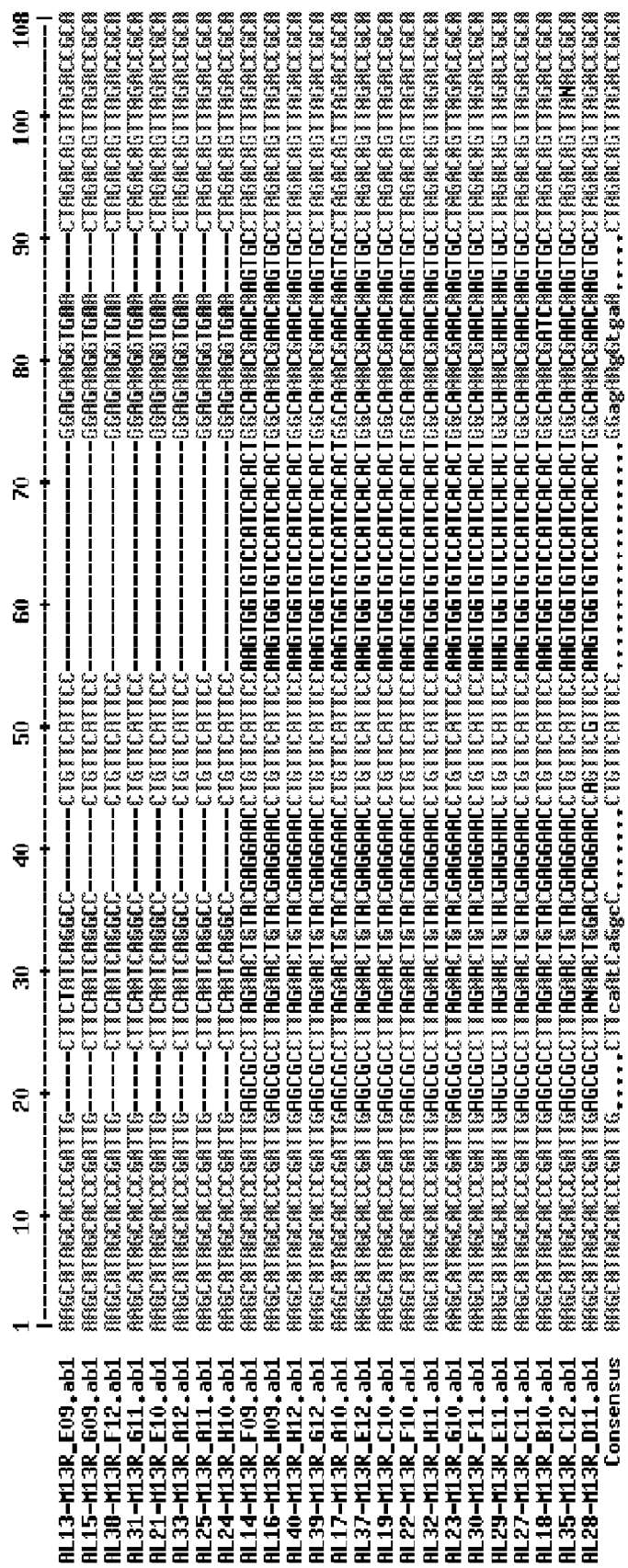

FIG. 40 shows sequence data derived from the cloned amplification product of the repeat-dependent-recombination-mediated cDNA generation/PCR amplification of mixed TKR_S and TKR_L in free solution.

FIG. 41 shows TKR_2_click_S and TKR_2_click_L conjugates and their LCMS traces.

Figure 42:
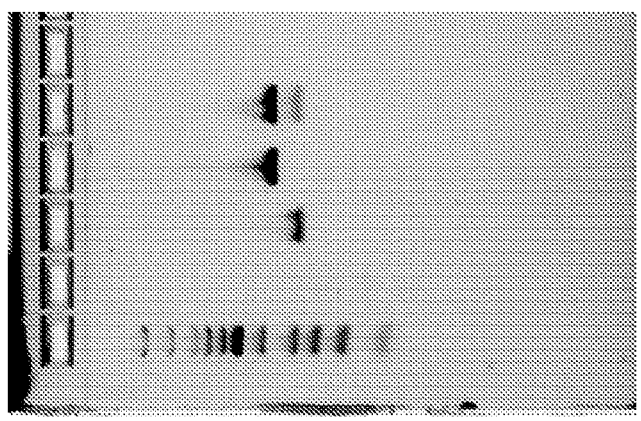

FIG. 42 shows Deep Vent (exo-) Polymerase repeat-dependent-recombination-mediated cDNA generation/PCR amplification of 2_click_S and 2_click_L in free solution. 1—Marker; 2—No template control; 3—2_click_S; 4—2_click_L; 5—:1 mixture of 2_click_S and 2_click_L. Conditions: 5 uL of 10× Thermopol buffer; 2.5 uL of a 10 uM solution of each forward and reverse primer; 2.5 uL 10 mM dNTP mix (NEB); 40 pM final concentration of either conjugate or their 1:1 mixture, 2.5 uL Deep Vent (exo-) Polymerase and water to 50 uL. The reaction was cycled 22 times as follows: 30 seconds at 94° C., 30 seconds at 52° C. and 60 seconds at 72° C.

Figure 43:
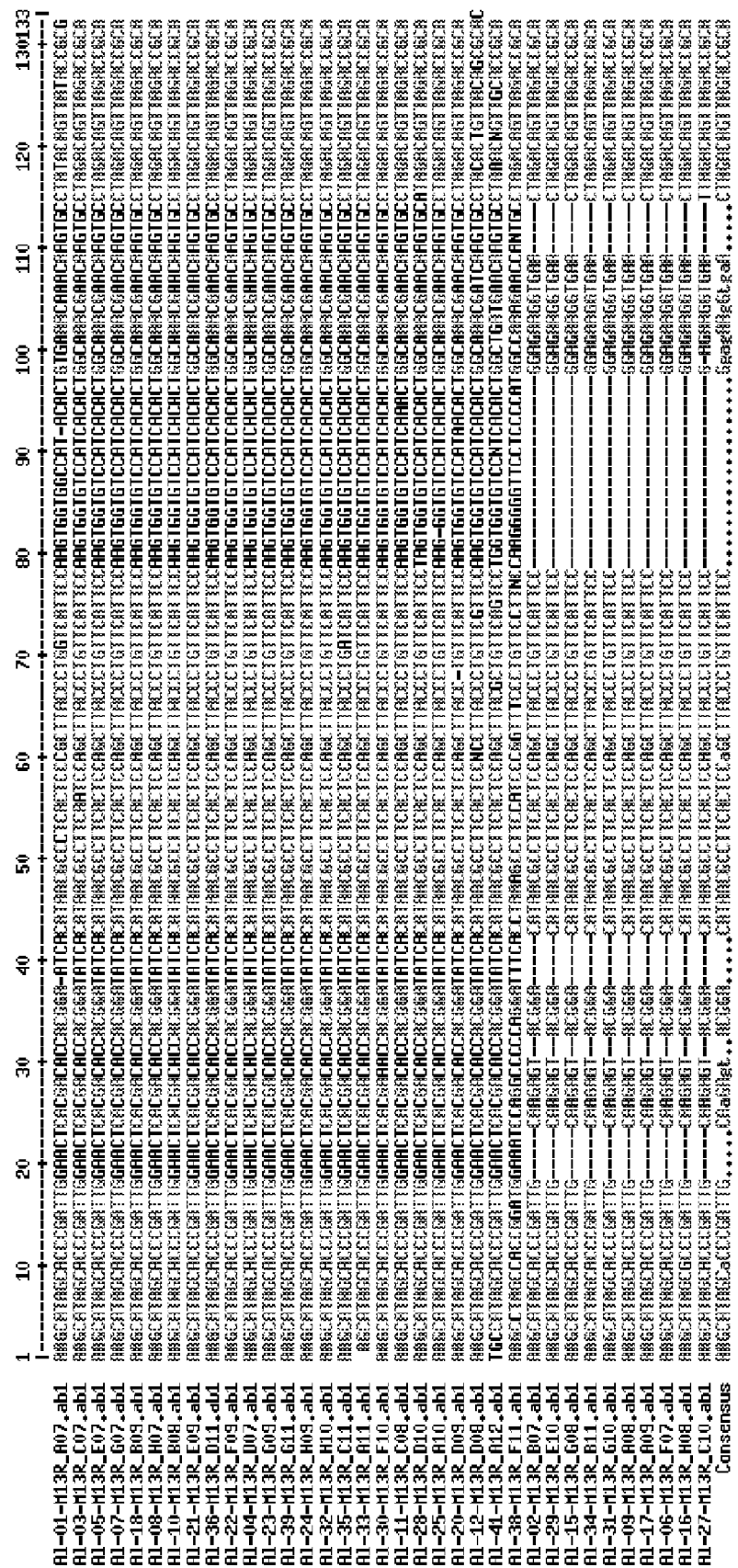

FIG. 43 shows sequence data derived from the cloned amplification product of the repeat-dependent-recombination-mediated cDNA generation/PCR amplification product of TKR_2_click_S and TKR_2_click_L mixture in free solution.

DETAILED DESCRIPTION

We have developed complexes having at least one linkage (e.g., a chemical linkage) for which a polymerase has reduced ability to read or translocate through. The ability to tag libraries without being constrained by readability of a polymerase greatly expands the range of tagging methods that can be used. Possible, non-limiting advantages include decreased mass of tags and/or library members; increased solubility of library members in various reaction conditions (e.g., in aqueous and/or organic conditions suitable for both chemical entity and tag synthesis); increased stability (e.g., in aqueous and/or organic reaction conditions, where such oligonucleotide tags and linkages may be more resistant to particular reaction conditions, as compared to tag without such linkages); decreased cost (e.g., reduce use of expensive enzyme reagents); increased ease of use (e.g., use of cyanovinylcarbazole cross-linking occurs over a broad pH range of 5.5-9.5, which permits cross-linking under reaction conditions suitable for forming the chemical entity-portion of the complex); reduced number of reaction steps and reduced use of reagent(s) (e.g., reduced use of a buffer exchange step, such as during combinatorial split reactions, where thousands of individual, small aliquots need to be independently processed; a precipitation step, or a pH-modification step); increased fidelity (e.g., when hybridization-mediated methods are used to reduce the frequency of occurrence of mis-tagging events); and increased compatibility with reaction conditions for forming the chemical entity (e.g., allows for use of orthogonal functionalities, where unique, tagging chemistries (e.g., use of UV irradiation) can be used that will not occur during post-split/mix step(s), which will also reduce the frequency of mis-tagging events).

Because such linkages may have reduced readability by a polymerase, we have also developed methods to allow for sequencing such complexes. These methods include use of relay primers to span the linkages and/or use of releasable cross-linking oligonucleotides. These complexes and methods can be used to create diverse libraries of selectable chemical entities by establishing an encoded relationship between particular tags and particular chemical reactions or building blocks. To identify one or more chemical entities, the oligonucleotide tags can be amplified, cloned, sequenced, and correlated by using the established relationship. Methods of creating and tagging libraries of these complexes are described in detail below.

Complexes

This invention features a complex including a chemical entity, one or more tags, and a headpiece operatively associated with the chemical entity and one or more tags. At least one of the linkages between the headpiece and the tag or between two tags is a linkage for which a polymerase has reduced ability to read or translocate through. The chemical entities, headpieces, tags, linkages, and bifunctional spacers are further described below.

Chemical Entities

The chemical entities or members (e.g., small molecules or peptides) of the invention can include one or more building blocks and optionally include one or more scaffolds.

The scaffold S can be a single atom or a molecular scaffold. Exemplary single atom scaffolds include a carbon atom, a boron atom, a nitrogen atom, or a phosphorus atom, etc. Exemplary polyatomic scaffolds include a cycloalkyl group, a cycloalkenyl group, a heterocycloalkyl group, a heterocycloalkenyl group, an aryl group, or a heteroaryl group. Particular embodiments of a heteroaryl scaffold include a triazine, such as 1,3,5-triazine, 1,2,3-triazine, or 1,2,4-triazine; a pyrimidine; a pyrazine; a pyridazine; a furan; a pyrrole; a pyrroline; a pyrrolidine; an oxazole; a pyrazole; an isoxazole; a pyran; a pyridine; an indole; an indazole; or a purine.

The scaffold S can be operatively linked to the tag by any useful method. In one example, S is a triazine that is linked directly to the headpiece. To obtain this exemplary scaffold, trichlorotriazine (i.e., a chlorinated precursor of triazine having three chlorines) is reacted with a nucleophilic group of the headpiece. Using this method, S has three positions having chlorine that are available for substitution, where two positions are available diversity nodes and one position is attached to the headpiece. Next, building block $A_n$ is added to a diversity node of the scaffold, and tag $A_n$ encoding for building block $A_n$ ("tag $A_n$") is ligated to the headpiece, where these two steps can be performed in any order. Then, building block $B_n$ is added to the remaining diversity node, and tag $B_n$ encoding for building block $B_n$ is ligated to the end of tag $A_n$. In another example, S is a triazine that is operatively linked to a tag, where trichlorotriazine is reacted with a nucleophilic group (e.g., an amino group) of a PEG, aliphatic, or aromatic linker of a tag. Building blocks and associated tags can be added, as described above.

In yet another example, S is a triazine that is operatively linked to building block $A_n$. To obtain this scaffold, building block $A_n$ having two diversity nodes (e.g., an electrophilic group and a nucleophilic group, such as an Fmoc-amino acid) is reacted with the nucleophilic group of a linker (e.g., the terminal group of a PEG, aliphatic, or aromatic linker, which is attached to a headpiece). Then, trichlorotriazine is reacted with a nucleophilic group of building block $A_n$. Using this method, all three chlorine positions of S are used as diversity nodes for building blocks. As described herein, additional building blocks and tags can be added, and additional scaffolds $S_n$ can be added.

Exemplary building block $A_n$'s include, e.g., amino acids (e.g., alpha-, beta-, gamma-, delta-, and epsilon-amino acids, as well as derivatives of natural and unnatural amino acids), chemical-reactive reactants (e.g., azide or alkyne chains) with an amine, or a thiol reactant, or combinations thereof. The choice of building block $A_n$ depends on, for example, the nature of the reactive group used in the linker, the nature of a scaffold moiety, and the solvent used for the chemical synthesis.

Exemplary building block $B_n$'s and $C_n$'s include any useful structural unit of a chemical entity, such as optionally substituted aromatic groups (e.g., optionally substituted phenyl or benzyl), optionally substituted heterocyclyl groups (e.g., optionally substituted quinolinyl, isoquinolinyl, indolyl, isoindolyl, azaindolyl, benzimidazolyl, azabenzimidazolyl, benzisoxazolyl, pyridinyl, piperidyl, or pyrrolidinyl), optionally substituted alkyl groups (e.g., optionally substituted linear or branched $C_{1-6}$ alkyl groups or optionally substituted $C_{1-6}$ aminoalkyl groups), or optionally substituted carbocyclyl groups (e.g., optionally substituted cyclopropyl, cyclohexyl, or cyclohexenyl). Particularly useful building block $B_n$'s and $C_n$'s include those with one or more reactive groups, such as an optionally substituted group (e.g., any described herein) having one or optional substituents that are reactive groups or can be chemically modified to form reactive groups. Exemplary reactive groups include one or more of amine (—$NR_2$, where each R is, independently, H or an optionally substituted $C_{1-6}$ alkyl), hydroxy, alkoxy (—OR, where R is an optionally substituted $C_{1-6}$ alkyl, such as methoxy), carboxy (—COOH), amide, or chemical-reactive substituents. A restriction site may be introduced, for example, in tag $B_n$ or $C_n$, where a complex can be identified by performing PCR and restriction digest with one of the corresponding restriction enzymes.

Headpiece

In the library, the headpiece operatively links each chemical entity to its encoding oligonucleotide tag. Generally, the headpiece is a starting oligonucleotide having two functional groups that can be further derivatized, where the first functional group operatively links the chemical entity (or a component thereof) to the headpiece and the second functional group operatively links one or more tags to the headpiece. A bifunctional spacer can optionally be used as a spacing moiety between the headpiece and the chemical entity.

The functional groups of the headpiece can be used to form a covalent bond with a component of the chemical entity and another covalent bond with a tag. The component can be any part of the small molecule, such as a scaffold having diversity nodes or a building block. Alternatively, the headpiece can be derivatized to provide a spacer (i.e., a spacing moiety separating the headpiece from the small molecule to be formed in the library) terminating in a functional group (e.g., a hydroxyl, amine, carboxyl, sulfhydryl, alkynyl, azido, or phosphate group), which is used to form the covalent linkage with a component of the chemical entity. The spacer can be attached to the 5'-terminus, at one of the internal positions, or to the 3'-terminus of the headpiece. When the spacer is attached to one of the internal positions, the spacer can be operatively linked to a derivatized base (e.g., the C5 position of uridine) or placed internally within the oligonucleotide using standard techniques known in the art. Exemplary spacers are described herein.

The headpiece can have any useful structure. The headpiece can be, e.g., 1 to 100 nucleotides in length, preferably 5 to 20 nucleotides in length, and most preferably 5 to 15 nucleotides in length. The headpiece can be single-stranded or double-stranded and can consist of natural or modified nucleotides, as described herein. For example, the chemical moiety can be operatively linked to the 3'-terminus or 5'-terminus of the headpiece. In particular embodiments, the headpiece includes a hairpin structure formed by complementary bases within the sequence. For example, the chemical moiety can be operatively linked to the internal position, the 3'-terminus, or the 5'-terminus of the headpiece.

Generally, the headpiece includes a non-self-complementary sequence on the 5'- or 3'-terminus that allows for binding an oligonucleotide tag by polymerization, enzymatic ligation, or chemical reaction. The headpiece can allow for ligation of oligonucleotide tags and optional purification and phosphorylation steps. After the addition of the last tag, an additional adapter sequence can be added to the 5'-terminus of the last tag. Exemplary adapter sequences include a primer-binding sequence or a sequence having a label (e.g., biotin). In cases where many building blocks and corresponding tags are used (e.g., 100), a mix-and-split strategy may be employed during the oligonucleotide synthesis step to create the necessary number of tags. Such mix-and-split strategies for DNA synthesis are known in the art. The resultant library members can be amplified by PCR following selection for binding entities versus a target(s) of interest.

The headpiece or the complex can optionally include one or more primer-binding sequences. For example, the headpiece has a sequence in the loop region of the hairpin that serves as a primer-binding region for amplification, where the primer-binding region has a higher melting temperature for its complementary primer (e.g., which can include flanking identifier regions) than for a sequence in the headpiece. In other embodiments, the complex includes two primer-binding sequences (e.g., to enable a PCR reaction) on either side of one or more tags that encode one or more building blocks. Alternatively, the headpiece may contain one primer-binding sequence on the 5'- or 3'-terminus. In other embodiments, the headpiece is a hairpin, and the loop region forms a primer-binding site or the primer-binding site is introduced through hybridization of an oligonucleotide to the headpiece on the 3' side of the loop. A primer oligonucleotide, containing a region homologous to the 3'-terminus of the headpiece and carrying a primer-binding region on its 5'-terminus (e.g., to enable a PCR reaction) may be hybridized to the headpiece and may contain a tag that encodes a building block or the addition of a building block. The primer oligonucleotide may contain additional information, such as a region of randomized nucleotides, e.g., 2 to 16 nucleotides in length, which is included for bioinformatics analysis.

The headpiece can optionally include a hairpin structure, where this structure can be achieved by any useful method. For example, the headpiece can include complementary bases that form intermolecular base pairing partners, such as by Watson-Crick DNA base pairing (e.g., adenine-thymine and guanine-cytosine) and/or by wobble base pairing (e.g., guanine-uracil, inosine-uracil, inosine-adenine, and inosine-cytosine). In another example, the headpiece can include modified or substituted nucleotides that can form higher affinity duplex formations compared to unmodified nucleotides, such modified or substituted nucleotides being known in the art. In yet another example, the headpiece includes one or more cross-linked bases to form the hairpin structure. For example, bases within a single strand or bases in different double strands can be cross-linked, e.g., by using psoralen.

The headpiece or complex can optionally include one or more labels that allow for detection. For example, the headpiece, one or more oligonucleotide tags, and/or one or more primer sequences can include an isotope, a radioimaging agent, a marker, a tracer, a fluorescent label (e.g., rhodamine or fluorescein), a chemiluminescent label, a quantum dot, and a reporter molecule (e.g., biotin or a his-tag).

In other embodiments, the headpiece or tag may be modified to support solubility in semi-, reduced-, or non-aqueous (e.g., organic) conditions. Nucleotide bases of the headpiece or tag can be rendered more hydrophobic by modifying, for example, the C5 positions of T or C bases with aliphatic chains without significantly disrupting their ability to hydrogen bond to their complementary bases. Exemplary modified or substituted nucleotides are 5'-dimethoxytrityl-N4-diisobutylaminomethylidene-5-(1-propynyl)-2'-deoxycytidine, 3'-[(2-cyanoethyl)-(N,N-diisopropyl)]-phosphoramidite; 5'-dimethoxytrityl-5-(1-propynyl)-2'-deoxyuridine, 3'-[(2-cyanoethyl)-(N,N-diisopropyl)]-phosphoramidite; 5'-dimethoxytrityl-5-fluoro-2'-deoxyuridine, 3'-[(2-cyanoethyl)-(N,N-diisopropyl)]-phosphoramidite; and 5'-dimethoxytrityl-5-(pyren-1-yl-ethynyl)-2'-deoxyuridine, or 3'-[(2-cyanoethyl)-(N,N-diisopropyl)]-phosphoramidite.

In addition, the headpiece oligonucleotide can be interspersed with modifications that promote solubility in organic solvents. For example, azobenzene phosphoramidite can introduce a hydrophobic moiety into the headpiece design. Such insertions of hydrophobic amidites into the headpiece can occur anywhere in the molecule. However, the insertion cannot interfere with subsequent tagging using additional DNA tags during the library synthesis or ensuing PCR once a selection is complete or microarray analysis, if used for tag deconvolution. Such additions to the headpiece design described herein would render the headpiece soluble in, for example, 15%, 25%, 30%, 50%, 75%, 90%, 95%, 98%, 99%, or 100% organic solvent. Thus, addition of hydrophobic residues into the headpiece design allows for improved solubility in semi- or non-aqueous (e.g., organic) conditions, while rendering the headpiece competent for oligonucleotide tagging. Furthermore, DNA tags that are subsequently introduced into the library can also be modified at the C5 position of T or C bases such that they also render the library more hydrophobic and soluble in organic solvents for subsequent steps of library synthesis.

In particular embodiments, the headpiece and the first tag can be the same entity, i.e., a plurality of headpiece-tag entities can be constructed that all share common parts (e.g., a primer-binding region) and all differ in another part (e.g., encoding region). These may be utilized in the "split" step and pooled after the event they are encoding has occurred.

In particular embodiments, the headpiece can encode information, e.g., by including a sequence that encodes the first split(s) step or a sequence that encodes the identity of the library, such as by using a particular sequence related to a specific library.

Oligonucleotide Tags

The oligonucleotide tags described herein (e.g., a tag or a portion of a headpiece or a portion of a tailpiece) can be used to encode any useful information, such as a molecule, a portion of a chemical entity, the addition of a component (e.g., a scaffold or a building block), a headpiece in the library, the identity of the library, the use of one or more library members (e.g., use of the members in an aliquot of a library), and/or the origin of a library member (e.g., by use of an origin sequence).

Any sequence in an oligonucleotide can be used to encode any information. Thus, one oligonucleotide sequence can serve more than one purpose, such as to encode two or more types of information or to provide a starting oligonucleotide that also encodes for one or more types of information. For example, the first tag can encode for the addition of a first building block, as well as for the identification of the library. In another example, a headpiece can be used to provide a starting oligonucleotide that operatively links a chemical entity to a tag, where the headpiece additionally includes a sequence that encodes for the identity of the library (i.e., the library-identifying sequence). Accordingly, any of the information described herein can be encoded in separate oligonucleotide tags or can be combined and encoded in the same oligonucleotide sequence (e.g., an oligonucleotide tag, such as a tag, or a headpiece).

A building block sequence encodes for the identity of a building block and/or the type of binding reaction conducted with a building block. This building block sequence is included in a tag, where the tag can optionally include one or more types of sequence described below (e.g., a library-identifying sequence, a use sequence, and/or an origin sequence).

A library-identifying sequence encodes for the identity of a particular library. In order to permit mixing of two or more libraries, a library member may contain one or more library-identifying sequences, such as in a library-identifying tag (i.e., an oligonucleotide including a library-identifying sequence), in a ligated tag, in a part of the headpiece sequence, or in a tailpiece sequence. These library-identifying sequences can be used to deduce encoding relationships, where the sequence of the tag is translated and correlated with chemical (synthesis) history information. Accordingly, these library-identifying sequences permit the mixing of two or more libraries together for selection, amplification, purification, sequencing, etc.

A use sequence encodes the history (i.e., use) of one or more library members in an individual aliquot of a library. For example, separate aliquots may be treated with different reaction conditions, building blocks, and/or selection steps. In particular, this sequence may be used to identify such aliquots and deduce their history (use) and thereby permit the mixing together of aliquots of the same library with different histories (uses) (e.g., distinct selection experiments) for the purposes of the mixing together of samples together for selection, amplification, purification, sequencing, etc. These use sequences can be included in a headpiece, a tailpiece, a tag, a use tag (i.e., an oligonucleotide including a use sequence), or any other tag described herein (e.g., a library-identifying tag or an origin tag).

An origin sequence is a degenerate (random, stochastically-generated) oligonucleotide sequence of any useful length (e.g., about six oligonucleotides) that encodes for the origin of the library member. This sequence serves to stochastically subdivide library members that are otherwise identical in all respects into entities distinguishable by sequence information, such that observations of amplification products derived from unique progenitor templates (e.g., selected library members) can be distinguished from observations of multiple amplification products derived from the same progenitor template (e.g., a selected library member). For example, after library formation and prior to the selection step, each library member can include a different origin sequence, such as in an origin tag. After selection, selected library members can be amplified to produce amplification products, and the portion of the library member expected to include the origin sequence (e.g., in the origin tag) can be observed and compared with the origin sequence in each of the other library members. As the origin sequences are degenerate, each amplification product of each library member should have a different origin sequence. However, an observation of the same origin sequence in the amplification product could indicate multiple amplicons derived from the same template molecule. When it is desired to determine the statistics and demographics of the population of encoding tags prior to amplification, as opposed to post-amplification, the origin tag may be used. These origin sequences can be included in a headpiece, a tailpiece, a tag, an origin tag (i.e., an oligonucleotide including an origin sequence), or any other tag described herein (e.g., a library-identifying tag or a use tag).

Any of the types of sequences described herein can be included in the headpiece. For example, the headpiece can include one or more of a building block sequence, a library-identifying sequence, a use sequence, or an origin sequence.

Any of these sequences described herein can be included in a tailpiece. For example, the tailpiece can include one or more of a library-identifying sequence, a use sequence, or an origin sequence.

Any of tags described herein can include a connector at or in proximity to the 5'- or 3'-terminus having a fixed sequence. Connectors facilitate the formation of linkages (e.g., chemical linkages) by providing a reactive group (e.g., a chemical-reactive group or a photo-reactive group) or by providing a site for an agent that allows for a linkage (e.g., an agent of an intercalating moiety or a reversible reactive group in the connector(s) or cross-linking oligonucleotide). Each 5'-connector may be the same or different, and each 3'-connector may be the same or different. In an exemplary, non-limiting complex having more than one tags, each tag can include a 5'-connector and a 3'-connector, where each 5'-connector has the same sequence and each 3'-connector has the same sequence (e.g., where the sequence of the 5'-connector can be the same or different from the sequence of the 3'-connector). The connector provides a sequence that can be used for one or more linkages. To allow for binding of a relay primer or for hybridizing a cross-linking oligonucleotide, the connector can include one or more functional groups allowing for a linkage (e.g., a linkage for which a polymerase has reduced ability to read or translocate through, such as a chemical linkage).

These sequences can include any modification described herein for oligonucleotides, such as one or more modifications that promote solubility in organic solvents (e.g., any described herein, such as for the headpiece), that provide an analog of the natural phosphodiester linkage (e.g., a phosphorothioate analog), or that provide one or more non-natural oligonucleotides (e.g., 2'-substituted nucleotides, such as 2'-O-methylated nucleotides and 2'-fluoro nucleotides, or any described herein).

These sequences can include any characteristics described herein for oligonucleotides. For example, these sequences can be included in tag that is less than 20 nucleotides (e.g., as described herein). In other examples, the tags including one or more of these sequences have about the same mass (e.g., each tag has a mass that is about +/−10% from the average mass between within a specific set of tags that encode a specific variable); lack a primer-binding (e.g., constant) region; lack a constant region; or have a constant region of reduced length (e.g., a length less than 30 nucleotides, less than 25 nucleotides, less than 20 nucleotides, less than 19 nucleotides, less than 18 nucleotides, less than 17 nucleotides, less than 16 nucleotides, less than 15 nucleotides, less than 14 nucleotides, less than 13 nucleotides, less than 12 nucleotides, less than 11 nucleotides, less than 10 nucleotides, less than 9 nucleotides, less than 8 nucleotides, or less than 7 nucleotides).

Sequencing strategies for libraries and oligonucleotides of this length may optionally include concatenation or catenation strategies to increase read fidelity or sequencing depth, respectively. In particular, the selection of encoded libraries that lack primer-binding regions has been described in the literature for SELEX, such as described in Jarosch et al., *Nucleic Acids Res.* 34: e86 (2006), which is incorporated herein by reference. For example, a library member can be modified (e.g., after a selection step) to include a first adapter sequence on the 5'-terminus of the complex and a second adapter sequence on the 3'-terminus of the complex, where the first sequence is substantially complementary to the second sequence and result in forming a duplex. To further improve yield, two fixed dangling nucleotides (e.g., CC) are added to the 5'-terminus. In particular embodiments, the first adapter sequence is 5'-GTGCTGC-3' (SEQ ID NO: 1), and the second adapter sequence is 5'-GCAGCACCC-3' (SEQ ID NO: 2).

Linkages

The linkages of the invention are present between oligonucleotides that encode information (e.g., such as between the headpiece and a tag, between two tags, or between a tag and a tailpiece), where such linkages include any linkage for which a polymerase has reduced ability to read or translocate through. Exemplary linkages include chemical linkages including one or more of a chemical-reactive group, a photo-reactive group, an intercalating moiety, a cross-linking oligonucleotide, or a reversible co-reactive group.

A linkage may be tested to determine whether a polymerase has reduced ability to read or translocate through that linkage. This ability can be tested by any useful method, such as liquid chromatography-mass spectrometry, RT-PCR analysis, sequence demographics, and/or PCR analysis.

In particular embodiments, chemical ligation includes the use of one or more chemical-reactive pairs to provide a linkage. Exemplary chemical-reactive pairs are a pair including an optionally substituted alkynyl group and an optionally substituted azido group to form a triazole via a Huisgen 1,3-dipolar cycloaddition reaction; an optionally substituted diene having a 4 $\pi$-electron system (e.g., an optionally substituted 1,3-unsaturated compound, such as optionally substituted 1,3-butadiene, 1-methoxy-3-trimethylsilyloxy-1,3-butadiene, cyclopentadiene, cyclohexadiene, or furan) and an optionally substituted dienophile or an optionally substituted heterodienophile having a 2 $\pi$-electron system (e.g., an optionally substituted alkenyl group or an optionally substituted alkynyl group) to form a cycloalkenyl via a Diels-Alder reaction; a nucleophile (e.g., an optionally substituted amine or an optionally substituted thiol) with a strained heterocyclyl electrophile (e.g., optionally substituted epoxide, aziridine, aziridinium ion, or episulfonium ion) to form a heteroalkyl via a ring opening reaction; a phosphorothioate group with an iodo group, such as in a splinted ligation of an oligonucleotide containing 5'-iodo dT with a 3'-phosphorothioate oligonucleotide; an optionally substituted amino group with an aldehyde group or a ketone group, such as a reaction of a 3'-aldehyde-modified oligonucleotide, which can optionally be obtained by oxidizing a commercially available 3'-glyceryl-modified oligonucleotide, with 5'-amino oligonucleotide (i.e., in a reductive amination reaction) or a 5'-hydrazido oligonucleotide; a pair of an optionally substituted amino group and a carboxylic acid group or a thiol group (e.g., with or without the use of succinimidyl trans-4-(maleimidylmethyl)cyclohexane-1-carboxylate (SMCC) or 1-ethyl-3-(3-dimethylaminopropyl)carbodiimide (EDAC); a pair of an optionally substituted hydrazine and an aldehyde or a ketone group; a pair of an optionally substituted hydroxylamine and an aldehyde or a ketone group; or a pair of a nucleophile and an optionally substituted alkyl halide.

Platinum complexes, alkylating agents, or furan-modified nucleotides can also be used as a chemical-reactive group to form inter- or intra-strand linkages. Such agents can be used between two oligonucleotides and can optionally be present in the cross-linking oligonucleotide.

Exemplary, non-limiting platinum complexes include cis-platin (cis-diamminedichloroplatinum(II), e.g., to form GG intra-strand linkages), transplatin (trans-diaminedichloroplatinum(II), e.g., to form GXG inter-strand linkages, where X can be any nucleotide), carboplatin, picolatin (ZD0473), ormaplatin, or oxaliplatin to form, e.g., GC, CG, AG, or GG linkages. Any of these linkages can be inter- or intra-strand linkages.

Exemplary, non-limiting alkylating agents include nitrogen mustard (mechlorethamine, e.g., to form GG linkages), chlorambucil, melphalan, cyclophosphamide, prodrug forms of cyclophosphamide (e.g., 4-hydroperoxycyclophosphamide and ifosfamide)), 1,3-bis(2-chloroethyl)-1-nitrosourea (BCNU, carmustine), an aziridine (e.g., mitomycin C, triethylenemelamine, or triethylenethiophosphoramide (thio-tepa) to form GG or AG linkages), hexamethylmelamine, an alkyl sulfonate (e.g., busulphan to form GG linkages), or a nitrosourea (e.g., 2-chloroethylnitrosourea to form GG or CG linkages, such as carmustine (BCNU), chlorozotocin, lomustine (CCNU), and semustine (methyl-CCNU)). Any of these linkages can be inter- or intra-strand linkages.

Furan-modified nucleotides can also be used to form linkages. Upon in situ oxidation (e.g., with N-bromosuccinimide (NBS)), the furan moiety forms a reactive oxo-enal derivative that reacts with a complementary base to form an inter-strand linkage. In some embodiments, the furan-modified nucleotides forms linkages with a complementary A or C nucleotide. Exemplary, non-limiting furan-modified nucleotides include any 2'-(furan-2-yl)propanoylamino-modified nucleotide; or an acyclic, modified nucleotides of 2-(furan-2-yl)ethyl glycol nucleic acid.

Photo-reactive groups can also be used as a reactive group. Exemplary, non-limiting photo-reactive groups include an intercalating moiety, a psoralen derivative (e.g., psoralen, HMT-psoralen, or 8-methoxypsoralen), an optionally substituted cyanovinylcarbazole group, an optionally substituted vinylcarbazole group, an optionally substituted cyanovinyl group, an optionally substituted acrylamide group, an optionally substituted diazirine group, an optionally substituted benzophenone (e.g., succinimidyl ester of 4-benzoylbenzoic acid or benzophenone isothiocyanate), an optionally substituted 5-(carboxy)vinyl-uridine group (e.g., 5-(carboxy)vinyl-2'-deoxyuridine), or an optionally substituted azide group (e.g., an aryl azide or a halogenated aryl azide, such as succinimidyl ester of 4-azido-2,3,5,6-tetrafluorobenzoic acid (ATFB)).

Intercalating moieties can also be used as a reactive group. Exemplary, non-limiting intercalating moieties include a psoralen derivative, an alkaloid derivative (e.g., berberine, palmatine, coralyne, sanguinarine (e.g., iminium or alkanolamine forms thereof), or aristololactam-β-D-glucoside), an ethidium cation (e.g., ethidium bromide), an acridine derivative (e.g., proflavine, acriflavine, or amsacrine), an anthracycline derivative (e.g., doxorubicin, epirubicin, daunorubicin (daunomycin), idarubicin, and aclarubicin), or thalidomide.

For a cross-linking oligonucleotide, any useful reactive group (e.g., described herein) can be used to form inter- or intra-strand linkages. Exemplary reactive groups include chemical-reactive group, a photo-reactive group, an intercalating moiety, and a reversible co-reactive group. Cross-linking agents for use with cross-linking oligonucleotides include, without limitation, alkylating agents (e.g., as described herein), cisplatin (cis-diamminedichloroplatinum (II)), trans-diaminedichloroplatinum(II), psoralen, HMT-psoralen, 8-methoxypsoralen, furan-modified nucleotides, 2-fluoro-deoxyinosine (2-F-dI), 5-bromo-deoxycytosine (5-Br-dC), 5-bromo deoxyuridine (5-Br-dU), 5-iodo-deoxycytosine (5-I-dC), 5-iodo-deoxyuridine (5-I-dU), succinimidyl trans-4-(maleimidylmethyl)cyclohexane-1-carboxylate, SMCC, EDAC, or succinimidyl acetylthioacetate (SATA).

Oligonucleotides can also be modified to contain thiol moieties that can be reacted with a variety of thiol reactive groups such as maleimides, halogens, iodoacetamides and thus can be used for cross-linking two oligonucleotides. The thiol groups can be linked to the 5'- or the 3'-terminus of an oligonucleotide.

For inter-strand cross-linking between duplex oligonucleotides at a pyrimidine (e.g., thymidine) position, the intercalating, photo-reactive moiety psoralen can be chosen. Psoralen intercalates into the duplex and forms covalent inter-strand cross-links with pyrimidines, preferentially at 5'-TpA sites, upon irradiation with ultraviolet light (about 254 nm). The psoralen moiety can be covalently attached to a modified oligonucleotide (e.g., by an alkane chain, such as a $C_{1-10}$ alkyl, or a polyethylene glycol group, such as —$(CH_2CH_2O)_nCH_2CH_2$—, where n is an integer from 1 to 50). Exemplary psoralen derivatives can also be used, where non-limiting derivatives include 4'-(hydroxyethoxymethy)-4,5',8-trimethylpsoralen (HMT-psoralen) and 8-methoxypsoralen.

Various portions of the cross-linking oligonucleotide can be modified to introduce a linkage. For example, terminal phosphorothioates in oligonucleotides can also be used for linking two adjacent oligonucleotides. Halogenated uracils/cytosines can also be used as cross-linker modifications in the oligonucleotide. For example, 2-fluoro-deoxyinosine (2-F-dI) modified oligonucleotides can be reacted with disulfide-containing diamines or thiopropylamines to form disulfide linkages.

As described below, reversible co-reactive groups include those selected from a cyanovinylcarbazole group, a cyanovinyl group, an acrylamide group, a thiol group, or a sulfonylethyl thioethers. An optionally substituted cyanovinylcarbazole (CNV) group can also be used in oligonucleotides to cross-link to a pyrimidine base (e.g., cytosine, thymine, and uracil, as well as modified bases thereof) in complementary strands. CNV groups promote [2+2] cycloaddition with the adjacent pyrimidine base upon irradiation at 366 nm, which results in an inter-strand cross-link. Irradiation at 312 nm reverses the cross-link and thus provides a method for reversible cross-linking of oligonucleotide strands. A non-limiting CNV group is 3-cyanovinylcarbozaole, which can be included as a carboxyvinylcarbazole nucleotide (e.g., as 3-carboxyvinylcarbazole-1'-β-deoxyriboside-5'-triphosphate).

The CNV group can be modified to replace the reactive cyano group with another reactive group to provide an optionally substituted vinylcarbazole group. Exemplary non-limiting reactive groups for a vinylcarbazole group include an amide group of —$CONR_{N1}R_{N2}$, where each $R_{N1}$ and $R_{N2}$ can be the same or different and is independently H and $C_{1-6}$ alkyl, e.g., —$CONH_2$; a carboxyl group of —$CO_2H$; or a $C_{2-7}$ alkoxycarbonyl group (e.g., methoxycarbonyl). Furthermore, the reactive group can be located on the alpha or beta carbon of the vinyl group. Exemplary vinylcarbazole groups include a cyanovinylcarbazole group, as described herein; an amidovinylcarbazole group (e.g., an amidovinylcarbazole nucleotide, such as 3-amidovinylcarbazole-1'-β-deoxyriboside-5'-triphosphate); a carboxyvinylcarbazole group (e.g., a carboxyvinylcarbazole nucleotide, such as 3-carboxyvinylcarbazole-1'-β-deoxyriboside-5'-triphosphate); and a $C_{2-7}$ alkoxycarbonylvinylcarbazole group (e.g., an alkoxycarbonylvinylcarbazole nucleotide, such as 3-methoxycarbonylvinylcarbazole-1'-β-deoxyriboside-5'-triphosphate). Additional optionally substituted vinylcarbazole groups and nucleotides having such groups are provided in the chemical formulas of U.S. Pat. No. 7,972,792 and Yoshimura and Fujimoto, *Org. Lett.* 10:3227-3230 (2008), which are both hereby incorporated by reference in their entirety.

Other reversible reactive groups include a thiol group and another thiol group to form a disulfide, as well as a thiol group and a vinyl sulfone group to form a sulfonylethyl thioethers. Thiol-thiol groups can optionally include a linkage formed by a reaction with bis-((N-iodoacetyl)piperazinyl)sulfonerhodamine. Other reversible reactive groups (e.g., such as some photo-reactive groups) include optionally substituted benzophenone groups. A non-limiting example is benzophenone uracil (BPU), which can be used for site- and sequence-selective formation of an interstrand cross-link of BPU-containing oligonucleotide duplexes. This cross-link can be reversed upon heating, providing a method for the reversible cross-linking of two oligonucleotide strands.

In other embodiments, chemical ligation includes introducing an analog of the phosphodiester bond, e.g., for post-selection PCR analysis and sequencing. Exemplary analogs of a phosphodiester include a phosphorothioate linkage (e.g., as introduced by use of a phosphorothioate group and a leaving group, such as an iodo group), a phosphoramide linkage, or a phosphorodithioate linkage (e.g., as introduced by use of a phosphorodithioate group and a leaving group, such as an iodo group).

For any of the groups described herein (e.g., a chemical-reactive group, a photo-reactive group, an intercalating moiety, a cross-linking oligonucleotide, or a reversible co-reactive group), the group can be incorporated at or in proximity to the terminus of an oligonucleotide or between the 5'- and 3'-termini. Furthermore, one or more groups can be present in each oligonucleotide. When pairs of reactive groups are required, then oligonucleotides can be designed to facilitate a reaction between the pair of groups. In the non-limiting example of a cyanovinylcarbazole group that co-reacts with a pyrimidine base, the first oligonucleotide can be designed to include the cyanovinylcarbazole group at or in proximity to the 5'-terminus. In this example, a second oligonucleotide can be designed to be complementary to the first oligonucleotide and to include the co-reactive pyrimidine base at a position that aligns with the cyanovinylcarbazole group when the first and second oligonucleotide hybridizes. Any of the groups herein and any of the oligonucleotides having one or more groups can be designed to facilitate reaction between the groups to form one or more linkages.

Bifunctional Spacers

The bifunctional spacer between the headpiece and the chemical entity can be varied to provide an appropriate spacing moiety and/or to increase the solubility of the headpiece in organic solvent. A wide variety of spacers are commercially available that can couple the headpiece with the small molecule library. The spacer typically consists of linear or branched chains and may include a $C_{1-10}$ alkyl, a heteroalkyl of 1 to 10 atoms, a $C_{2-10}$ alkenyl, a $C_{2-10}$ alkynyl, $C_{5-10}$ aryl, a cyclic or polycyclic system of 3 to 20 atoms, a phosphodiester, a peptide, an oligosaccharide, an oligonucleotide, an oligomer, a polymer, or a poly alkyl glycol (e.g., a poly ethylene glycol, such as —$(CH_2CH_2O)_nCH_2CH_2$—, where n is an integer from 1 to 50), or combinations thereof.

The bifunctional spacer may provide an appropriate spacing moiety between the headpiece and a chemical entity of the library. In certain embodiments, the bifunctional spacer includes three parts. Part 1 may be a reactive group, which forms a covalent bond with DNA, such as, e.g., a carboxylic acid, preferably activated by a N-hydroxy succinimide (NHS) ester to react with an amino group on the DNA (e.g., amino-modified dT), an amidite to modify the 5' or 3'-terminus of a single-stranded headpiece (achieved by means of standard oligonucleotide chemistry), chemical-reactive pairs (e.g., azido-alkyne cycloaddition in the presence of Cu(I) catalyst, or any described herein), or thiol reactive groups. Part 2 may also be a reactive group, which forms a covalent bond with the chemical entity, either building block $A_n$ or a scaffold. Such a reactive group could be, e.g., an amine, a thiol, an azide, or an alkyne. Part 3 may be a chemically inert spacing moiety of variable length, introduced between Part 1 and 2. Such a spacing moiety can be a chain of ethylene glycol units (e.g., PEGs of different lengths), an alkane, an alkene, a polyene chain, or a peptide chain. The spacer can contain branches or inserts with hydrophobic moieties (such as, e.g., benzene rings) to improve solubility of the headpiece in organic solvents, as well as fluorescent moieties (e.g. fluorescein or Cy-3) used for library detection purposes. Hydrophobic residues in the headpiece design may be varied with the spacer design to facilitate library synthesis in organic solvents. For example, the headpiece and spacer combination is designed to have appropriate residues wherein the octanol:water coefficient ($P_{oct}$) is from, e.g., 1.0 to 2.5.

Spacers can be empirically selected for a given small molecule library design, such that the library can be synthesized in organic solvent, for example, in 15%, 25%, 30%, 50%, 75%, 90%, 95%, 98%, 99%, or 100% organic solvent. The spacer can be varied using model reactions prior to library synthesis to select the appropriate chain length that solubilizes the headpiece in an organic solvent. Exemplary spacers include those having increased alkyl chain length, increased poly ethylene glycol units, branched species with positive charges (to neutralize the negative phosphate charges on the headpiece), or increased amounts of hydrophobicity (for example, addition of benzene ring structures).

Examples of commercially available spacers include amino-carboxylic spacers, such as those being peptides (e.g., Z-Gly-Gly-Gly-Osu (N-alpha-benzyloxycarbonyl-(Glycine)$_3$-N-succinimidyl ester) or Z-Gly-Gly-Gly-Gly-Gly-Gly-Osu (N-alpha-benzyloxycarbonyl-(Glycine)$_6$-N-succinimidyl ester, SEQ ID NO: 3)), PEG (e.g., Fmoc-aminoPEG2000-NHS or amino-PEG (12-24)-NHS), or alkane acid chains (e.g., Boc-ε-aminocaproic acid-Osu); chemical-reactive pair spacers, such as those chemical-reactive pairs described herein in combination with a peptide moiety (e.g., azidohomoalanine-Gly-Gly-Gly-OSu (SEQ ID NO: 4) or propargylglycine-Gly-Gly-Gly-OSu (SEQ ID NO: 5)), PEG (e.g., azido-PEG-NHS), or an alkane acid chain moiety (e.g., 5-azidopentanoic acid, (S)-2-(azidomethyl)-1-Boc-pyrrolidine, 4-azidoaniline, or 4-azido-butan-1-oic acid N-hydroxysuccinimide ester); thiol-reactive spacers, such as those being PEG (e.g., SM(PEG)n NHS-PEGmaleimide), alkane chains (e.g., 3-(pyridin-2-yldisulfanyl)-propionic acid-Osu or sulfosuccinimidyl 6-(3'-[2-pyridyldithio]-propionamido)hexanoate)); and amidites for oligonucleotide synthesis, such as amino modifiers (e.g., 6-(trifluoroacetylamino)-hexyl-(2-cyanoethyl)-(N,N-diisopropyl)-phosphoramidite), thiol modifiers (e.g., S-trityl-6-mercaptohexyl-1-[(2-cyanoethyl)-(N,N-diisopropyl)]-phosphoramidite, or chemical-reactive pair modifiers (e.g., 6-hexyn-1-yl-(2-cyanoethyl)-(N,N-diisopropyl)-phosphoramidite, 3-dimethoxytrityloxy-2-(3-(3-propargyloxypropanamido)propanamido)propyl-1-O-succinoyl, long chain alkylamino CPG, or 4-azido-butan-1-oic acid N-hydroxysuccinimide ester)). Additional spacers are known in the art, and those that can be used during library synthesis include, but are not limited to, 5'-O-dimethoxytrityl-1',2'-dideoxyribose-3'-[(2-cyanoethyl)-(N,N-diisopropyl)]-phosphoramidite; 9-O-dimethoxytrityl-triethylene glycol, 1[(2-cyanoethyl)-(N,N-diisopropyl)]-phosphoramidite; 3-(4,4'-dimethoxytrityloxy)propyl-1-[(2-cyanoethyl)-(N,N-diisopropyl)]-phosphoramidite; and 18-O-dimethoxytrityl hexaethyleneglycol, 1-[(2-cyanoethyl)-(N,N-diisopropyl)]-phosphoramidite. Any of the spacers herein can be added in tandem to one another in different combinations to generate spacers of different desired lengths.

Spacers may also be branched, where branched spacers are well known in the art and examples can consist of symmetric or asymmetric doublers or a symmetric trebler. See, for example, Newcome et al., Dendritic Molecules: Concepts, Synthesis, Perspectives, VCH Publishers (1996); Boussif et al., *Proc. Natl. Acad. Sci. USA* 92:7297-7301 (1995); and Jansen et al., *Science* 266:1226 (1994).

Enzymatic Ligation and Chemical Ligation Techniques

Various ligation techniques can be used to add scaffolds, building blocks, spacers, linkages, tags, and/or the headpiece to produce a complex. Accordingly, any of the binding steps described herein can include any useful ligation techniques, such as enzymatic ligation and/or chemical ligation. These binding steps can include the addition of one or more tags to the headpiece or complex; the addition of a spacer to the headpiece; and the addition of one or more scaffolds or building blocks to the headpiece or complex. In particular embodiments, the ligation techniques used for any oligonucleotide provide a resultant product that can be transcribed and/or reverse transcribed to allow for decoding of the library or for template-dependent polymerization with one or more DNA or RNA polymerases.

Generally, enzymatic ligation produces an oligonucleotide having a native phosphodiester bond that can be transcribed and/or reverse transcribed. Exemplary methods of enzyme ligation are provided herein and include the use of one or more RNA or DNA ligases, such as T4 RNA ligase, T4 DNA ligase, CircLigase™ ssDNA ligase, CircLigase™ II ssDNA ligase, and ThermoPhage™ ssDNA ligase (Prokazyme Ltd., Reykjavik, Iceland).

Chemical ligation can also be used to produce oligonucleotides capable of being transcribed or reverse transcribed. The efficacy of a chemical ligation technique to provide oligonucleotides capable of being transcribed or reverse transcribed may need to be tested. This efficacy can be tested by any useful method, such as liquid chromatography-mass spectrometry, RT-PCR analysis, and/or PCR analysis. In particular embodiments, chemical ligation includes the use of one or more chemical-reactive pairs to provide a spacing moiety that can be transcribed or reverse transcribed. In particular, reactions suitable for chemical-reactive pairs are preferred candidates for the ligation process (Kolb et al., *Angew. Chem. Int. Ed.,* 40:2004-2021 (2001); Van der Eycken et al., *QSAR Comb. Sci.,* 26:1115-1326 (2007)). In one embodiment, the ligated oligonucleotides contain a linkage that polymerases have a reduced ability to read or translocate through, e.g. an "unreadable" linkage.

Reaction Conditions to Promote Enzymatic Ligation or Chemical Ligation

The methods described herein can include one or more reaction conditions that promote enzymatic or chemical ligation between the headpiece and a tag or between two tags. These reaction conditions include using modified nucleotides within the tag, as described herein; using donor tags and acceptor tags having different lengths and varying the concentration of the tags; using different types of ligases, as well as combinations thereof (e.g., CircLigase™ DNA ligase and/or T4 RNA ligase), and varying their concentration; using poly ethylene glycols (PEGs) having different molecular weights and varying their concentration; use of non-PEG crowding agents (e.g., betaine or bovine serum albumin); varying the temperature and duration for ligation; varying the concentration of various agents, including ATP, $Co(NH_3)_6Cl_3$, and yeast inorganic pyrophosphate; using enzymatically or chemically phosphorylated oligonucleotide tags; using 3'-protected tags; and using preadenylated tags. These reaction conditions also include chemical ligations.

The headpiece and/or tags can include one or more modified or substituted nucleotides. In preferred embodiments, the headpiece and/or tags include one or more modified or substituted nucleotides that promote enzymatic ligation, such as 2'-O-methyl nucleotides (e.g., 2'-O-methyl guanine or 2'-O-methyl uracil), 2'-fluoro nucleotides, or any other modified nucleotides that are utilized as a substrate for ligation. Alternatively, the headpiece and/or tags are modified to include one or more chemically reactive groups to support chemical ligation (e.g. an optionally substituted alkynyl group and an optionally substituted azido group). Optionally, the tag oligonucleotides are functionalized at both termini with chemically reactive groups, and, optionally, one of these termini is protected, such that the groups may be addressed independently and side-reactions may be reduced (e.g., reduced polymerization side-reactions).

Enzymatic ligation can include one or more ligases. Exemplary ligases include CircLigase™ ssDNA ligase (EPICENTRE Biotechnologies, Madison, Wis.), CircLigase™ II ssDNA ligase (also from EPICENTRE Biotechnologies), ThermoPhage™ ssDNA ligase (Prokazyme Ltd., Reykjavik, Iceland), T4 RNA ligase, and T4 DNA ligase. In preferred embodiments, ligation includes the use of an RNA ligase or a combination of an RNA ligase and a DNA ligase. Ligation can further include one or more soluble multivalent cations, such as $Co(NH_3)_6Cl_3$, in combination with one or more ligases.

Before or after the ligation step, the complex can be purified for three reasons. First, the complex can be purified to remove unreacted headpiece or tags that may result in cross-reactions and introduce "noise" into the encoding process. Second, the complex can be purified to remove any reagents or unreacted starting material that can inhibit or lower the ligation activity of a ligase. For example, phosphate may result in lowered ligation activity. Third, entities that are introduced into a chemical or ligation step may need to be removed to enable the subsequent chemical or ligation step. Methods of purifying the complex are described herein.

Enzymatic and chemical ligation can include poly ethylene glycol having an average molecular weight of more than 300 Daltons (e.g., more than 600 Daltons, 3,000 Daltons, 4,000 Daltons, or 4,500 Daltons). In particular embodiments, the poly ethylene glycol has an average molecular weight from about 3,000 Daltons to 9,000 Daltons (e.g., from 3,000 Daltons to 8,000 Daltons, from 3,000 Daltons to 7,000 Daltons, from 3,000 Daltons to 6,000 Daltons, and from 3,000 Daltons to 5,000 Daltons). In preferred embodiments, the poly ethylene glycol has an average molecular weight from about 3,000 Daltons to about 6,000 Daltons (e.g., from 3,300 Daltons to 4,500 Daltons, from 3,300 Daltons to 5,000 Daltons, from 3,300 Daltons to 5,500 Daltons, from 3,300 Daltons to 6,000 Daltons, from 3,500 Daltons to 4,500 Daltons, from 3,500 Daltons to 5,000 Daltons, from 3,500 Daltons to 5,500 Daltons, and from 3,500 Daltons to 6,000 Daltons, such as 4,600 Daltons). Poly ethylene glycol can be present in any useful amount, such as from about 25% (w/v) to about 35% (w/v), such as 30% (w/v).

In a preferred embodiment of this invention, the tags are installed by ligation of a single-stranded oligonucleotide to a single-stranded oligonucleotide using the ligation protocol outlined below: Headpiece: 25 µM (5' terminus: 5'-monophospho/2'-OMe G, intervening nucleotides: 2'-deoxy, and 3' terminus: 2'-blocked/3'-blocked); Tag: 25 µM (5'-terminus: 2'-OMe/5'-OH G, intervening nucleotides: 2'-deoxy, and 3'-terminus: 3'-OH/2'-OMe); Co(NH$_3$)$_6$Cl$_3$: 1 mM; PEG 4600: 30% (w/v); T4 RNA Ligase (Promega): 1.5 units/µl; Yeast Inorganic Pyrophosphatase: 0.0025 units/µl; Tris: 50 mM; MgCl$_2$: 10 mM; ATP: 1 mM; pH: 7.5; and Water: Balance. In further embodiments, the protocol includes incubation at 37° C. for 20 hours. For the purposes of actual library construction, higher concentration of headpiece, tags, and/or ligase may be used, and such modifications to these concentrations would be apparent to those skilled in the art. Chemical ligation methodologies can include any chemical method that enables the operative association of two encoding tags, whether or not a polymerase is able to read or translocate through the operatively-associated linkage.

Methods for Determining the Nucleotide Sequence of a Complex

This invention features a method for determining the nucleotide sequence of a complex, such that encoding relationships may be established between the sequence of the tag and the structural units (or building blocks) of the chemical entity. In particular, the identity and/or history of a chemical entity can be inferred from the sequence of bases in the oligonucleotide. Using this method, a library including diverse chemical entities or members (e.g., small molecules or peptides) can be addressed with a particular tag sequence.

FIGS. 1-4 provide various exemplary methods for determining the nucleotide sequence of a complex. These figures provide exemplary methods to span unreadable linkage and/or release cross-linking oligonucleotides, which result in the formation of an oligonucleotide template.

FIG. 1b provides an exemplary method using relay primers. In particular, the relay primers hybridize to the fixed constant sequence portions (e.g., the 5'- and 3'-connectors), where each sequence for the relay primers can be the same or different. The relay primers span the unreadable linkage, and extension proceeds along the readable portions of the complex (i.e., the encoding sequence, e.g., one or more tags) to produce oligonucleotide fragments. Then, the relay primers and fragments can be ligated to form a template, which can be optionally amplified and sequenced.

Figure 1:
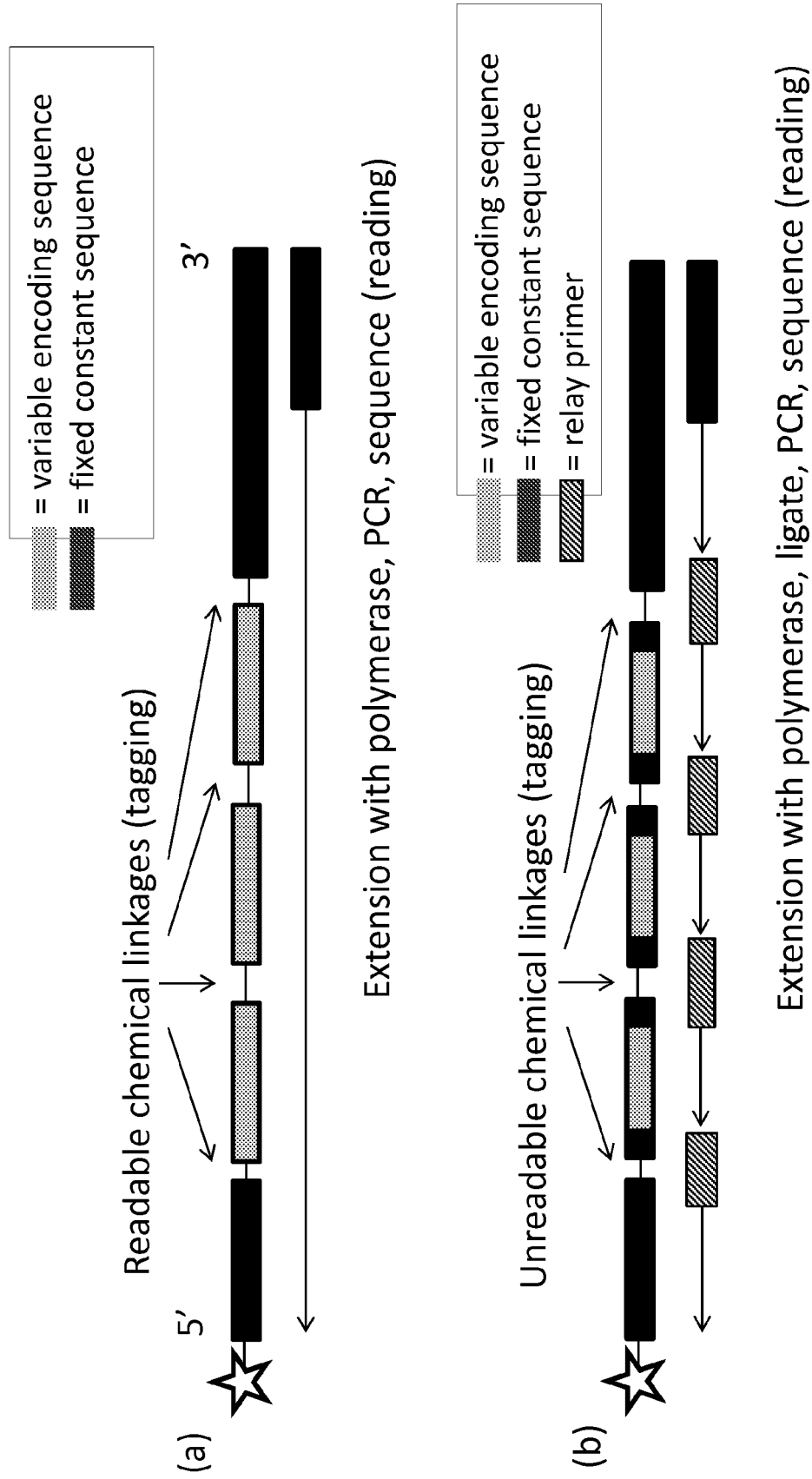
FIGS. 1A-1B shows exemplary complexes.
Figure 2:
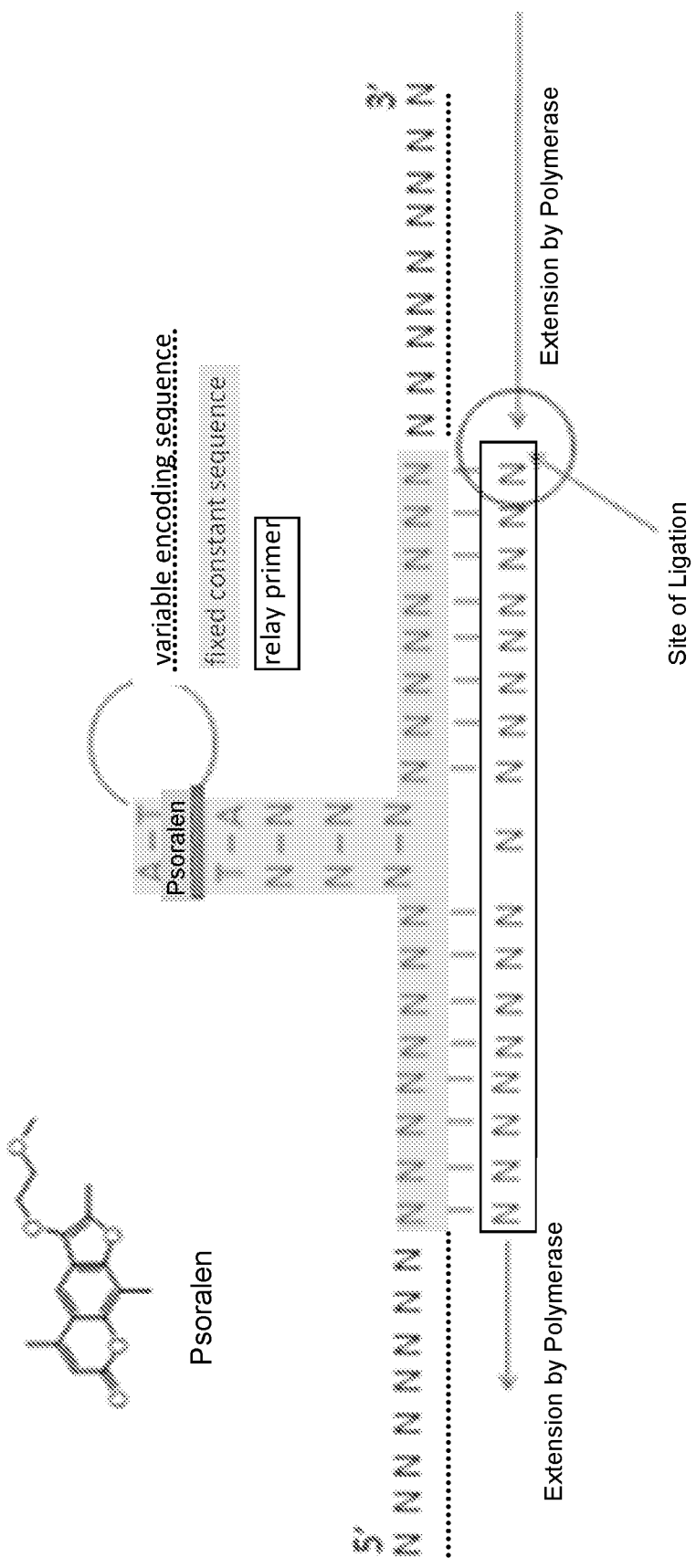
FIG. 2 show an exemplary complex having an unreadable linkage formed by psoralen. The schematic provides (from the 5' to 3' direction) a variable encoding sequence, a 3'-connector, a 5'-connector, and another variable encoding sequence. The 3'-connector and 5'-connector hybridizes to form a duplex, and psoralen (an intercalating, photo-reactive moiety) forms an unreadable linkage between the 5'- and 3'-connectors. The relay primer hybridizes to the 5'- and 3'-connectors and spans the unreadable linkage. The readable portions of the complex (e.g., the variable encoding sequence) are extended with a polymerase to form oligonucleotide fragments. The fragments and relay primers are ligated using ligase, optionally amplified with PCR, and sequenced. The reading process (e.g., extension, ligation, optional amplification, and sequencing) may optionally be entirely performed after selection. Alternatively, the extension and ligation part of the reading process may be performed prior to selection.
Figure 3:
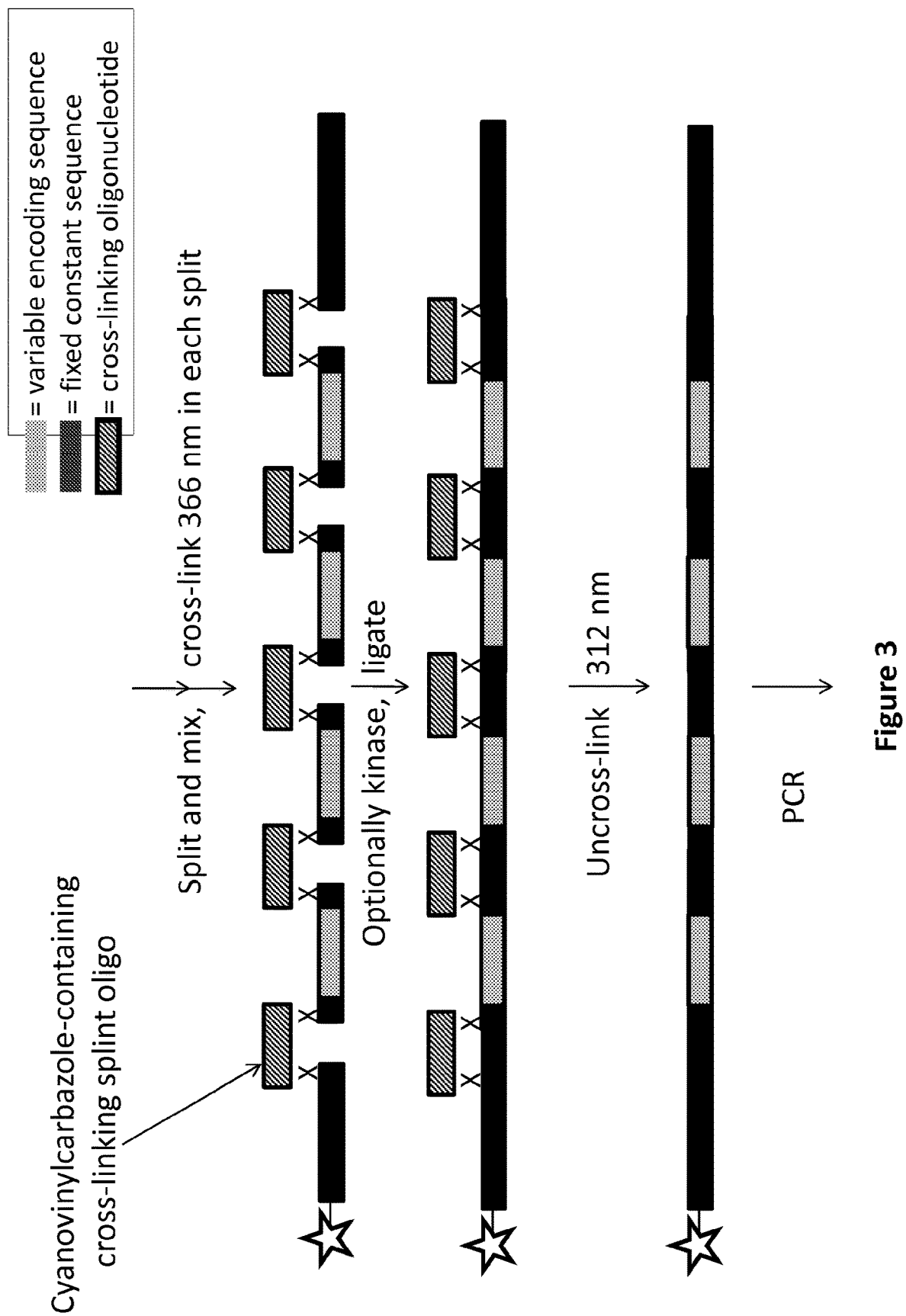
FIG. 3 show an exemplary complex having unreadable linkages formed by a cross-linking oligonucleotide. In the top schematic, the complex includes (from the 5' to 3' direction) a chemical entity (star), a fixed constant sequence (e.g., a headpiece), a cross-linking oligonucleotide that is cross-linked via a reversible co-reactive group (e.g., cyanovinylcarbazole groups cross-linked at about 366 nm, cross-links marked with X), and followed by a variable encoding sequence having fixed constant sequences at the 5'- and 3'-termini (e.g., a tag having 5'- and 3'-connectors). The combination of the cross-linking oligonucleotide and variable encoding sequence are repeated three more times. Then, the final cross-linking oligonucleotide and another fixed constant sequence (e.g., a tailpiece) follows. The cross-links are marked with X. Next, the complex is reacted with a chemical process and/or an enzymatic process (e.g., a ligase and optionally a kinase) to ligate the tags. Next, the cross-linking oligonucleotides are released to form a template (e.g., using absorption at about 312 nm). Finally, the template is optionally amplified with PCR and sequenced. The reading process (e.g., optional kinase step, ligation, optional amplification, and sequencing) may optionally be entirely performed after selection. Alternatively, the optional kinase step and ligation step of the reading process may be performed prior to selection.
Figure 4:
FIG. 4 shows an exemplary reversible reaction with reversible co-reactive groups (a pair of a cyanovinylcarbazole group and a thymidine) and use of these groups permits the formation of cross-links between the cross-linking oligonucleotide and the fixed constant sequence of the oligonucleotide tag. Reversible co-reactive groups (marked by X and X') are present in the 3'-connector, 5'-connector, and cross-linking oligonucleotide.

FIGS. 2-4 provide exemplary unreadable linkages FIG. 2 provides a linkage formed by psoralen, which reacts within a duplex formed by adjacent 5'- and 3'-connectors. FIG. 3 provides a linkage formed by a cross-linked oligonucleotide, which hybridized to adjacent 5'- and 3'-connectors.

Any of the linkages described herein can be reversible or irreversible. Reversible linkages include photo-reactive linkages (e.g., a cyanovinylcarbozole group and thymidine, as in FIG. 4) and redox linkages. Additional linkages are described herein.

In an alternative embodiment, an "unreadable" linkage can be enzymatically repaired in order to generate a readable or at least translocatable linkage. Enzymatic repair processes are well known to those skilled in the art and include, but are not limited to, pyrimidine (e.g., thymidine) dimer repair mechanisms (e.g., using a photolyase or a glycosylase (e.g., T4 pyrimidine dimer glycosylase (PDG))), base excision repair mechanisms (e.g., using a glycosylase, an apurinic/apyrimidinic (AP) endonuclease, a Flap endonuclease, or a poly ADP ribose polymerase (e.g., human apurinic/apyrimidinic (AP) endonuclease, APE 1; endonuclease III (Nth) protein; endonuclease IV; endonuclease V; formamidopyrimidine [fapy]-DNA glycosylase (Fpg); human 8-oxoguanine glycosylase 1 (a isoform) (hOGG1); human endonuclease VIII-like 1 (hNEIL1); uracil-DNA glycosylase (UDG); human single-strand selective monofunctional uracil DNA glycosylase (SMUG1); and human alkyladenine DNA glycosylase (hAAG)), which can be optionally combined with one or more endonucleases, DNA or RNA polymerases, and/or a ligases for the repair), methylation repair mechanisms (e.g., using a methyl guanine methyltransferase), AP repair mechanisms (e.g., using an apurinic/apyrimidinic (AP) endonuclease (e.g., APE 1; endonuclease III; endonuclease IV; endonuclease V; Fpg; hOGG1; and hNEIL1), which can be optionally combined with one or more endonucleases, DNA or RNA polymerases, and/or a ligases for the repair), nucleotide excision repair mechanisms (e.g., using excision repair cross-complementing proteins or excision nucleases, which can be optionally combined with one or more endonucleases, DNA or RNA polymerases, and/or a ligases for the repair), and mismatch repair mechanisms (e.g., using an endonuclease (e.g., T7 endonuclease I; MutS, MutH, and/or MutL), which can be optionally combined with one or more exonucleases, endonucleases, helicases, DNA or RNA polymerases, and/or ligases for the repair). Commercial enzyme mixtures are available to readily provide these kinds of repair mechanisms, e.g., PreCR® Repair Mix (New England Biolabs Inc., Ipswich Mass.), which includes Taq DNA Ligase, Endonuclease IV, Bst DNA Polymerase, Fpg, Uracil-DNA Glycosylase (UDG), T4 PDG (T4 Endonuclease V), and Endonuclease VIII.

Methods for Tagging Encoded Libraries

This invention features a method for operatively associating oligonucleotide tags with chemical entities, such that encoding relationships may be established between the sequence of the tag and the structural units (or building blocks) of the chemical entity. In particular, the identity and/or history of a chemical entity can be inferred from the sequence of bases in the oligonucleotide. Using this method, a library including diverse chemical entities or members (e.g., small molecules or peptides) can be encoded with a particular tag sequence.

Generally, these methods include the use of a headpiece, which has at least one functional group that may be elaborated chemically and at least one functional group to which a single-stranded oligonucleotide may be bound (or ligated). Binding can be effectuated by any useful means, such as by enzymatic binding (e.g., ligation with one or more of an RNA ligase and/or a DNA ligase) or by chemical binding (e.g., by a substitution reaction between two functional groups, such as a nucleophile and a leaving group).

To create numerous chemical entities within the library, a solution containing the headpiece can be divided into multiple aliquots and then placed into a multiplicity of physically separate compartments, such as the wells of a multi-well plate. Generally, this is the "split" step. Within each compartment or well, successive chemical reaction and ligation steps are performed with a single-stranded tag within each aliquot. The relationship between the chemical reaction conditions and the sequence of the single-stranded tag are recorded. The reaction and ligation steps may be performed in any order. Then, the reacted and ligated aliquots are combined or "pooled," and optionally purification may be performed at this point. These split and pool steps can be optionally repeated.

Next, the library can be tested and/or selected for a particular characteristic or function, as described herein. For example, the mixture of tagged chemical entities can be separated into at least two populations, where the first population binds to a particular biological target and the second population does not (e.g., by negative selection or positive selection). The first population can then be selectively captured (e.g., by eluting on a column providing the target of interest or by incubating the aliquot with the target of interest) and, optionally, further analyzed or tested, such as with optional washing, purification, negative selection, positive selection, or separation steps.

Finally, the chemical histories of one or more members (or chemical entities) within the selected population can be determined by the sequence of the operatively linked oligonucleotide. Upon correlating the sequence with the particular building block, this method can identify the individual members of the library with the selected characteristic (e.g., an increased tendency to bind to the target protein and thereby elicit a therapeutic effect). For further testing and optimization, candidate therapeutic compounds may then be prepared by synthesizing the identified library members with or without their associated oligonucleotide tags.

The methods described herein can include any number of optional steps to diversify the library or to interrogate the members of the library. For any tagging method described herein, successive "n" number of tags can be added with additional "n" number of ligation, separation, and/or phosphorylation steps. Exemplary optional steps include restriction of library member-associated encoding oligonucleotides using one or more restriction endonucleases; repair of the associated encoding oligonucleotides, e.g., with any repair enzyme, such as those described herein; ligation of one or more adapter sequences to one or both of the termini for library member-associated encoding oligonucleotides, e.g., such as one or more adapter sequences to provide a priming sequence for amplification and sequencing or to provide a label, such as biotin, for immobilization of the sequence; reverse-transcription or transcription, optionally followed by reverse-transcription, of the assembled tags in the complex using a reverse transcriptase, transcriptase, or another template-dependent polymerase; amplification of the assembled tags in the complex using, e.g., PCR; generation of clonal isolates of one or more populations of assembled tags in the complex, e.g., by use of bacterial transformation, emulsion formation, dilution, surface capture techniques, etc.; amplification of clonal isolates of one or more populations of assembled tag in the complex, e.g., by using clonal isolates as templates for template-dependent polymerization of nucleotides; and sequence determination of clonal isolates of one or more populations of assembled tags in the complex, e.g., by using clonal isolates as templates for template-dependent polymerization with fluorescently labeled nucleotides. Additional methods for amplifying and sequencing the oligonucleotide tags are described herein.

These methods can be used to identify and discover any number of chemical entities with a particular characteristic or function, e.g., in a selection step. The desired characteristic or function may be used as the basis for partitioning the library into at least two parts with the concomitant enrichment of at least one of the members or related members in the library with the desired function. In particular embodiments, the method comprises identifying a small drug-like library member that binds or inactivates a protein of therapeutic interest. In another embodiment, a sequence of chemical reactions is designed, and a set of building blocks is chosen so that the reaction of the chosen building blocks under the defined chemical conditions will generate a combinatorial plurality of molecules (or a library of molecules), where one or more molecules may have utility as a therapeutic agent for a particular protein. For example, the chemical reactions and building blocks are chosen to create a library having structural groups commonly present in kinase inhibitors. In any of these instances, the oligonucleotide tags encode the chemical history of the library member and, in each case, a collection of chemical possibilities may be represented by any particular tag combination.

In one embodiment, the library of chemical entities, or a portion thereof, is contacted with a biological target under conditions suitable for at least one member of the library to bind to the target, followed by removal of library members that do not bind to the target, and analyzing the one or more oligonucleotide tags associated with the target. This method can optionally include amplifying the tags by methods known in the art. Exemplary biological targets include enzymes (e.g., kinases, phosphatases, methylases, demethylases, proteases, and DNA repair enzymes), proteins involved in protein:protein interactions (e.g., ligands for receptors), receptor targets (e.g., GPCRs and RTKs), ion channels, bacteria, viruses, parasites, DNA, RNA, prions, and carbohydrates.

In another embodiment, the chemical entities that bind to a target are not subjected to amplification but are analyzed directly. Exemplary methods of analysis include microarray analysis, including evanescent resonance photonic crystal analysis; bead-based methods for deconvoluting tags (e.g., by using his-tags); label-free photonic crystal biosensor analysis (e.g., a BIND® Reader from SRU Biosystems, Inc., Woburn, Mass.); or hybridization-based approaches (e.g. by using arrays of immobilized oligonucleotides complementary to sequences present in the library of tags).

In addition, chemical-reactive pairs (or functional groups) can be readily included in solid-phase oligonucleotide synthesis schemes and will support the efficient chemical ligation of oligonucleotides. In addition, the resultant ligated oligonucleotides can act as templates for template-dependent polymerization with one or more polymerases. Accordingly, any of the binding steps described herein for tagging encoded libraries can be modified to include one or more of enzymatic ligation and/or chemical ligation techniques. Exemplary ligation techniques include enzyme ligation, such as use of one of more RNA ligases and/or DNA ligases; and chemical ligation, such as use of chemical-reactive pairs (e.g., a pair including optionally substituted alkynyl and azido functional groups).

Furthermore, one or more libraries can be combined in a split-and-mix step. In order to permit mixing of two or more libraries, the library member may contain one or more library-identifying sequences, such as in a library-identifying tag, in a ligated tag, or as part of the headpiece sequence, as described herein.

Methods Having Reduced Mass

Much of the motivation for single-stranded encoding strategies arises from the reduced mass of a single-stranded tag when compared to a double-stranded tag. Reduced mass potentially confers several benefits including increased solubility, decreased cost, increased reactivity, increased target accessibility, decreased hydrodynamic radius, increased accuracy of analytical assessments, etc. In addition to using a single-stranded tagging methodology, further reductions in mass can be achieved by including the use of one or more of the following: one or more tags having a reduced length, constant mass tag sets, an encoding headpiece, one or more members of a library lacking a primer-binding region and/or a constant region, one or more members of a library having a reduced constant region, or any other methodologies described herein.

To minimize the mass of the members in the library, the length of one or more tags can be reduced, such as to a length that is as short as possible to encode each split size. In particular, the tags can be less than 20 nucleotides (e.g., less than 19 nucleotides, less than 18 nucleotides, less than 17 nucleotides, less than 16 nucleotides, less than 15 nucleotides, less than 14 nucleotides, less than 13 nucleotides, less than 12 nucleotides, less than 11 nucleotides, less than 10 nucleotides, less than 9 nucleotides, less than 8 nucleotides, or less than 7 nucleotides). As described below in the Examples, shorter tags (e.g, about 10 nucleotides or shorter) can be used for tag ligation.

Constant mass strategies can also be used, which could aid in analysis during library synthesis. In addition, constant mass tag sets could permit the recognition of all single error occurrences (e.g., errors arising from misreading a sequence or from chemical or enzymatic ligation of a tag) and most multiple error occurrences. The relationship between the length of a constant mass single-stranded tag set and encoding ability (e.g., minimum lengths to support specific building block split sizes or library identities, etc.) is outlined below in Table 1. Accordingly, use of constant mass tag sets could be used to provide beneficial encoding ability, while maintaining error recognition during library formation.

TABLE 1

| Length | Base #1 | Base #2 | Base #3 | Base #4 | Combinations |
|---|---|---|---|---|---|
| 1 | 1 | 0 | 0 | 0 | 1 |
| 2 | 1 | 1 | 0 | 0 | 2 |
| 3 | 1 | 1 | 1 | 0 | 6 |
| 4 | 1 | 1 | 1 | 1 | 24 |
| 5 | 2 | 1 | 2 | 1 | 60 |
| 6 | 2 | 2 | 1 | 1 | 180 |
| 7 | 2 | 2 | 2 | 1 | 630 |
| 8 | 2 | 2 | 2 | 2 | 2,520 |
| 9 | 3 | 2 | 2 | 2 | 7,560 |
| 10 | 3 | 3 | 2 | 2 | 25,200 |
| 11 | 3 | 3 | 3 | 2 | 92,400 |
| 12 | 3 | 3 | 3 | 3 | 369,600 |
| 13 | 4 | 3 | 3 | 3 | 1,201,200 |
| 14 | 4 | 4 | 3 | 3 | 4,204,200 |
| 15 | 4 | 4 | 4 | 3 | 15,765,750 |
| 16 | 4 | 4 | 4 | 4 | 63,063,000 |
| 17 | 5 | 4 | 4 | 4 | 214,414,200 |
| 18 | 5 | 5 | 4 | 4 | 771,891,120 |
| 19 | 5 | 5 | 5 | 4 | 2,933,186,256 |
| 20 | 5 | 5 | 5 | 5 | 11,732,745,024 |

To minimize mass in the library, the headpiece can be used not only to link the chemical moiety and a tag but to also encode for the identity of a particular library or for a particular step. For example, the headpiece can encode information, e.g., a plurality of headpieces that encode the first split(s) or the identity of the library, such as by using a particular sequence related to a specific library.

In addition, primer-binding (e.g., constant) regions from the library of DNA-encoded chemical entities can be excluded during the selection step(s). Then, these regions can be added after selection by, e.g., single-stranded ligation. One exemplary strategy would include providing a chemical entity at the 5'-terminus of a encoding oligonucleotide, selecting a particular chemical entity based on any useful particular characteristic or function, and ligating a tailpiece oligonucleotide to the 3'-terminus of the encoding oligonucleotide that includes a primer-binding sequence and may optionally contain one or more tags, e.g. a "use" tag, an "origin" tag, etc., as described herein. This primer-binding sequence could then be used to initiate template-dependent polymerization to generate cDNA (or cRNA) that is complementary to the selected library member. The cDNA or cRNA would then be ligated at its 3'-terminus to an oligonucleotide that contains a primer-binding sequence and, now that the encoding information is flanked on both sides by primer-binding sequences, the oligonucleotide may be sequenced and/or amplified using established approaches, such as any described herein.

Mass may further be minimized by omitting or reducing the size of one or more constant sequences that separate encoding tags. Single-stranded ligation requires no complementary relationship between the ends to be ligated or between these ends and a splint. Therefore, no fixed sequence is required to support enzymatic ligation. Short fixed regions between tags may be useful for informatic parsing of tags or other in silico deconvolution processes.

Methods for Encoding Chemical Entities Within a Library

The methods of the invention can be used to synthesize a library having a diverse number of chemical entities that are encoded by oligonucleotide tags. Examples of building blocks and encoding DNA tags are found in U.S. Patent Application Publication No. 2007/0224607, hereby incorporated by reference.

Each chemical entity is formed from one or more building blocks and optionally a scaffold. The scaffold serves to provide one or more diversity nodes in a particular geometry (e.g., a triazine to provide three nodes spatially arranged around a heteroaryl ring or a linear geometry).

The building blocks and their encoding tags can be added directly or indirectly (e.g., via a spacer) to the headpiece to form a complex. When the headpiece includes a spacer, the building block or scaffold is added to the end of the spacer. When the spacer is absent, the building block can be added directly to the headpiece or the building block itself can include a spacer that reacts with a functional group of the headpiece. Exemplary spacers and headpieces are described herein.

The scaffold can be added in any useful way. For example, the scaffold can be added to the end of the spacer or the headpiece, and successive building blocks can be added to the available diversity nodes of the scaffold. In another example, building block $A_n$ is first added to the spacer or the headpiece, and then the diversity node of scaffold S is reacted with a functional group in building block $A_n$. Oligonucleotide tags encoding a particular scaffold can optionally be added to the headpiece or the complex. For example, $S_n$ is added to the complex in n reaction vessels, where n is an integer more than one, and tag $S_n$ (i.e., tag $S_1, S_2, \ldots S_{n-1}, S_n$) is bound to the functional group of the complex.

Building blocks can be added in multiple, synthetic steps. For example, an aliquot of the headpiece, optionally having an attached spacer, is separated into n reaction vessels, where n is an integer of two or greater. In the first step, building block $A_n$ is added to each n reaction vessel (i.e., building block $A_1, A_2, \ldots A_{n-1}, A_n$ is added to reaction vessel $1, 2, \ldots n-1, n$), where n is an integer and each building block $A_n$ is unique. In the second step, scaffold S is added to each reaction vessel to form an $A_n$-S complex. Optionally, scaffold $S_n$ can be added to each reaction vessel to from an $A_n$-$S_n$ complex, where n is an integer of more than two, and each scaffold $S_n$ can be unique. In the third step, building block $B_n$ is to each n reaction vessel containing the $A_n$-S complex (i.e., building block $B_1, B_2, \ldots B_{n-1}, B_n$ is added to reaction vessel $1, 2, \ldots n-1, n$ containing the $A_1$-S, $A_2$-S, $\ldots A_{n-1}$-S, $A_n$-S complex), where each building block $B_n$ is unique. In further steps, building block $C_n$ can be added to each n reaction vessel containing the $B_n$-$A_n$-S complex (i.e., building block $C_1, C_2, \ldots C_{n-1}, C_n$ is added to reaction vessel $1, 2, \ldots n-1, n$ containing the $B_1$-$A_1$-S $\ldots B_n$-$A_n$-S complex), where each building block $C_n$ is unique. The resulting library will have $n^3$ number of complexes having $n^3$ tags. In this manner, additional synthetic steps can be used to bind additional building blocks to further diversify the library.

After forming the library, the resultant complexes can optionally be purified and subjected to a polymerization or ligation reaction, e.g., to a tailpiece. This general strategy can be expanded to include additional diversity nodes and building blocks (e.g., D, E, F, etc.). For example, the first diversity node is reacted with building blocks and/or S and encoded by an oligonucleotide tag. Then, additional building blocks are reacted with the resultant complex, and the subsequent diversity node is derivatized by additional building blocks, which is encoded by the primer used for the polymerization or ligation reaction To form an encoded library, oligonucleotide tags are added to the complex after or before each synthetic step. For example, before or after the addition of building block $A_n$ to each reaction vessel, tag $A_n$ is bound to the functional group of the headpiece (i.e., tag $A_1, A_2, \ldots A_{n-1}, A_n$ is added to reaction vessel $1, 2, \ldots n-1, n$ containing the headpiece). Each tag $A_n$ has a distinct sequence that correlates with each unique building block $A_n$, and determining the sequence of tag $A_n$ provides the chemical structure of building block $A_n$. In this manner, additional tags are used to encode for additional building blocks or additional scaffolds.

Furthermore, the last tag added to the complex can either include a primer-binding sequence or provide a functional group to allow for binding (e.g., by ligation) of a primer-binding sequence. The primer-binding sequence can be used for amplifying and/or sequencing the oligonucleotides tags of the complex. Exemplary methods for amplifying and for sequencing include polymerase chain reaction (PCR), linear chain amplification (LCR), rolling circle amplification (RCA), or any other method known in the art to amplify or determine nucleic acid sequences.

Using these methods, large libraries can be formed having a large number of encoded chemical entities. For example, a headpiece is reacted with a spacer and building block $A_n$, which includes 1,000 different variants (i.e., n=1,000). For each building block $A_n$, a DNA tag $A_n$ is ligated or primer extended to the headpiece. These reactions may be performed in a 1,000-well plate or 10×100 well plates. All reactions may be pooled, optionally purified, and split into a second set of plates. Next, the same procedure may be performed with building block $B_n$, which also include 1,000 different variants. A DNA tag $B_n$ may be ligated to the $A_n$-headpiece complex, and all reactions may be pooled. The resultant library includes 1,000×1,000 combinations of $A_n$×$B_n$ (i.e., 1,000,000 compounds) tagged by 1,000,000 different combinations of tags. The same approach may be extended to add building blocks $C_n$, $D_n$, $E_n$, etc. The generated library may then be used to identify compounds that bind to the target. The structure of the chemical entities that bind to the library can optionally be assessed by PCR and sequencing of the DNA tags to identify the compounds that were enriched.

This method can be modified to avoid tagging after the addition of each building block or to avoid pooling (or mixing). For example, the method can be modified by adding building block $A_n$ to n reaction vessels, where n is an integer of more than one, and adding the identical building block $B_1$ to each reaction well. Here, $B_1$ is identical for each chemical entity, and, therefore, an oligonucleotide tag encoding this building block is not needed. After adding a building block, the complexes may be pooled or not pooled. For example, the library is not pooled following the final step of building block addition, and the pools are screened individually to identify compound(s) that bind to a target. To avoid pooling all of the reactions after synthesis, a BIND® Reader (from SRU Biosystems, Inc.), for example, may be used to monitor binding on a sensor surface in high throughput format (e.g., 384 well plates and 1,536 well plates). For example, building block $A_n$ may be encoded with DNA tag $A_n$, and building block $B_n$ may be encoded by its position within the well plate. Candidate compounds can then be identified by using a binding assay (e.g., using a BIND® Biosensor, also available by SRU Biosystems, Inc., or using an ELISA assay) and by analyzing the $A_n$ tags by sequencing, microarray analysis and/or restriction digest analysis. This analysis allows for the identification of combinations of building blocks $A_n$ and $B_n$ that produce the desired molecules.

The method of amplifying can optionally include forming a water-in-oil emulsion to create a plurality of aqueous microreactors. The reaction conditions (e.g., concentration of complex and size of microreactors) can be adjusted to provide, on average, a microreactor having at least one member of a library of compounds. Each microreactor can also contain the target, a single bead capable of binding to a complex or a portion of the complex (e.g., one or more tags) and/or binding the target, and an amplification reaction solution having one or more necessary reagents to perform nucleic acid amplification. After amplifying the tag in the microreactors, the amplified copies of the tag will bind to the beads in the microreactors, and the coated beads can be identified by any useful method.

Once the building blocks from the first library that bind to the target of interest have been identified, a second library may be prepared in an iterative fashion. For example, one or two additional nodes of diversity can be added, and the second library is created and sampled, as described herein. This process can be repeated as many times as necessary to create molecules with desired molecular and pharmaceutical properties.

Various ligation techniques can be used to add the scaffold, building blocks, spacers, linkages, and tags. Accordingly, any of the binding steps described herein can include any useful ligation technique or techniques. Exemplary ligation techniques include enzymatic ligation, such as use of one of more RNA ligases and/or DNA ligases, as described herein; and chemical ligation, such as use of chemical-reactive pairs, as described herein.

EXAMPLE 1

General Strategy for Complexes

The complexes of the invention can be formed to include one or more linkages which a polymerase has reduced ability to read or translocate through. For example, complexes can be formed to include (from the 5' to 3' direction) a chemical entity (star), a fixed constant sequence (e.g., a headpiece), followed by three variable encoding sequences (e.g., three tags), and another fixed constant sequence (e.g., a tailpiece), where the linkage between the fixed constant sequences and variable encoding sequences can be unreadable (FIG. 1B).

Unreadable linkages can be formed by any useful moiety or functional group. A non-limiting example is psoralen (FIG. 2), which can form an unreadable linkage between the 5'- and 3'-connectors.

Unreadable linkages can be formed by a cross-linking oligonucleotide with a reversible co-reactive group of a cyanovinylcarbazole group. The complex can include (from the 5' to 3' direction) a chemical entity (star), a fixed constant sequence (e.g., a headpiece), a cross-linking oligonucleotide that is cross-linked via a reversible co-reactive group of a cyanovinylcarbazole group (cross-linked at about 366 nm, marked with X), and followed by a variable encoding sequence having fixed constant sequences at the 5'- and 3'-termini (e.g., a tag having 5'- and 3'-connectors) (FIG. 3). An exemplary reversible reaction with reversible co-reactive groups (a pair of a cyanovinylcarbazole group and a thymidine), which can be present in the 3'-connector, 5'-connector, and cross-linking oligonucleotide (FIG. 4). Other unreadable linkages may be rendered deconvolutable by the use of repair enzyme(s).

As part of the reading or deconvolution process, the complex can be reacted with a chemical process and/or an enzymatic process (e.g., a ligase and optionally a kinase) to ligate the tags. When the junction between adjacent tags is a nick, then ligase can be used to ligate the tags. Optionally, a kinase can be used to convert terminal 5'-hydroxyl groups to phosphate groups. When the junction between adjacent tags is a gap requiring extension with one or more nucleotides, then a polymerase can be used to extend across the gap prior to the ligation of the tags (optionally including kinase). Optionally the polymerase has reduced strand-displacement activity. Next, the cross-linking oligonucleotides are released to form a template (e.g., using irradiation at about 312 nm). Finally, the template is optionally amplified with PCR and sequenced.

For any of these complexes, each of the variable encoding sequences can optionally include a 5'-connector and a 3'-connector that are fixed constant sequences. Because the linkages are unreadable, relay primers can be used to span the linkages and to allow for extension with a polymerase, thus forming oligonucleotide fragments. The fragments can then be ligated using ligase, optionally amplified with PCR, and sequenced.

Alternatively encoding sequences on either side of an unreadable linkage may be copied into a single cDNA sequence using a recombination-mediated process in which recombination events are favored to occur for sequences derived from the same ancestral template sequence. This mechanism preserves tag association information and renders these associations deducible from derived sequence data. One possible method of generating unreadable linkages that may become templates for recombination-prone cDNA is to establish repeat homologous regions either side of the linkage.

EXAMPLE 2

Figure 5:
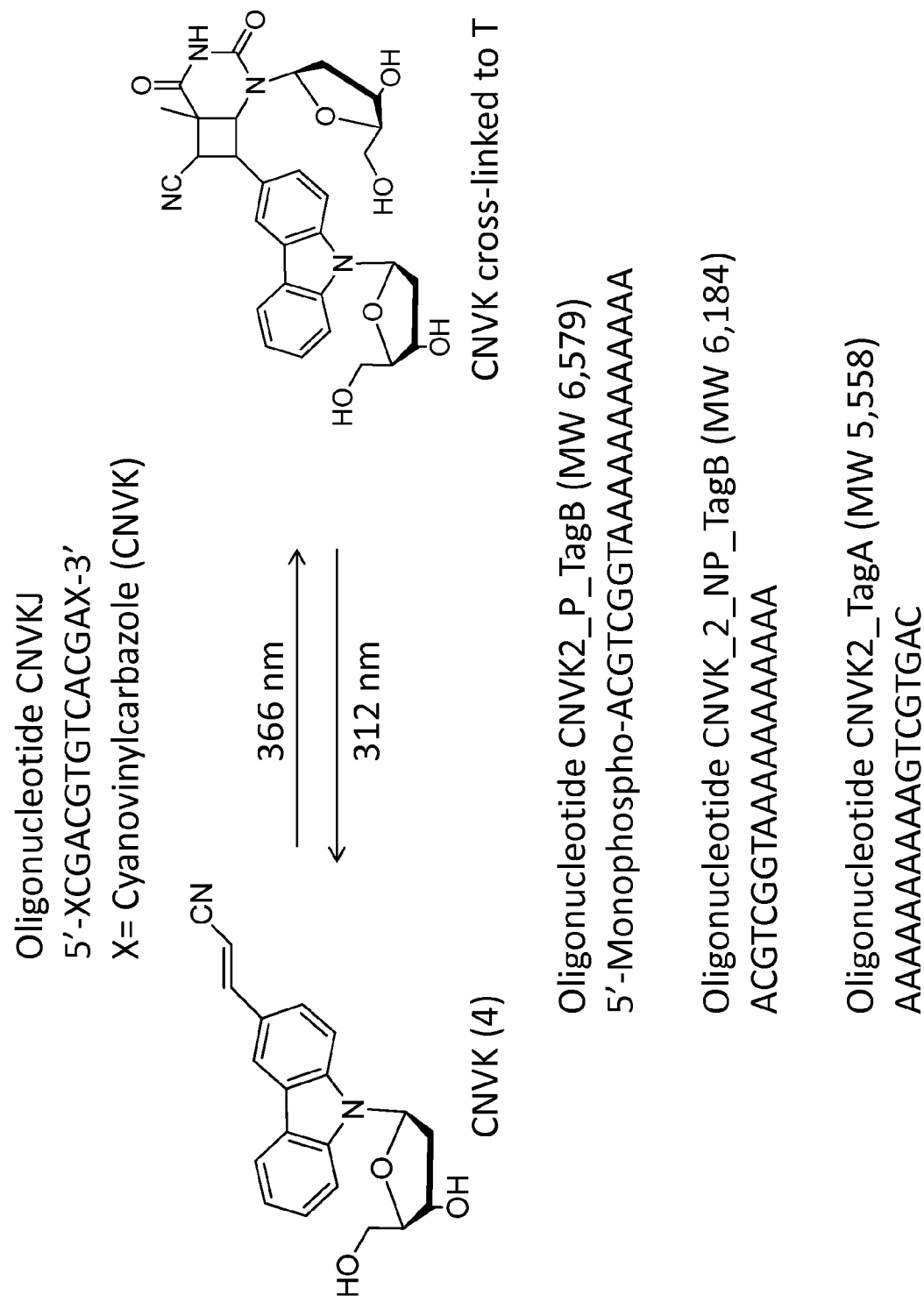
FIG. 5 shows Oligonucleotide CNVKJ, containing two cyanovinyl carbazole modifications, CNVK2_P_TagB, CNVK_2_NP_TagB, and CNVK2_TagA.

Photochemical Oligonucleotide Cross-Linking Using Cyanovinyl Carbazole to Model One Tagging Event Oligonucleotide CNVKJ, containing two cyanovinyl carbazole modifications, was obtained from Nihon Techno Service (Japan) (FIG. 5). Oligonucleotides CNVK2_P_TagB, CNVK2_NP_TagB and CNVK2_TagA were obtained from Integrated DNA Technologies (IDT) (IA). Each oligonucleotide was dissolved in water to a concentration of 1 mM.

Figure 6:
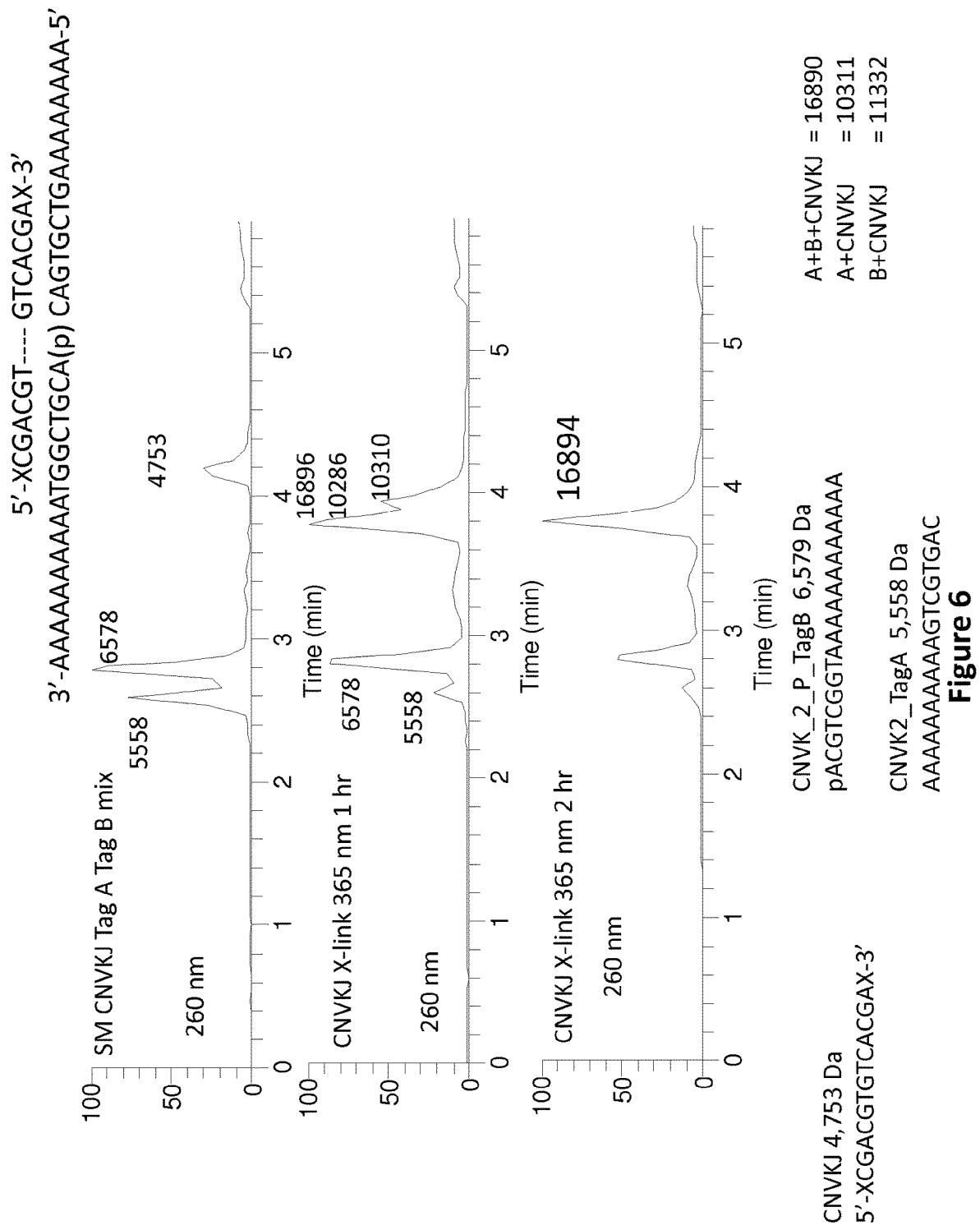
FIG. 6 shows the results of electrophoresis of the products of photochemical cross-linking of Oligonucleotides CNVKJ, CNVK2_P_TagB and CNVK2_TagA.

Photochemical cross-linking conditions were as follows: Oligonucleotides CNVKJ, CNVK2_P_TagB and CNVK2_TagA and were mixed at equimolar ratio at 100 uM each in 500 mM phosphate buffer at pH 7.0 in 20 uL or 50 uL aliquots in 1.5 mL natural color polypropylene microcentrifuge tubes (Fisher Scientific, 02-682-550). Each reaction was then was irradiated using a UVL-21 (4 Watt) lamp (95-0018-02) (Ultra Violet Products, CA) at 365 nm for 2 hours at 4° C. The products of the reactions were then analyzed by electrophoresis on a 10% denaturing PAAG as well as by LCMS (Thermo Fisher Scientific) (FIG. 6). Over 70% of the starting material was converted into the photochemically cross-linked oligonucleotide conjugate with an observed MW of 16,894 Da (calculated 16,890 Da). When the same cross-linking reaction was performed in 500 mM phosphate buffer at pH 5.5 or 500 mM Borate buffer at pH 9.5 similar results and yields were observed.

The photochemically cross-linked oligonucleotide conjugate of CNVK2_P_TagB, CNVK2_TagA and CNVKJ was purified on a 10% denaturing PAAG and was un-crosslinked by heating at 80° C. in 50 uL aliquots in 1.5 mL natural color polypropylene microcentrifuge tubes (Fisher Scientific, 02-682-550) with irradiation (at 80° C.) using a Spectroline E-Series EB-160C (6 Watt) lamp (Spectronics Corp., NY) at 312 nm for 1 hour. The products were analyzed by LCMS. The reaction quantitatively yields unaltered starting oligonucleotide model tags CNVK2_P_TagB observed MW 6,578 Da (calculated 6,579 Da) and CNVK2_TagA observed MW 5,558 Da (calculated 5,558 Da) (FIG. 7).

Figure 8:
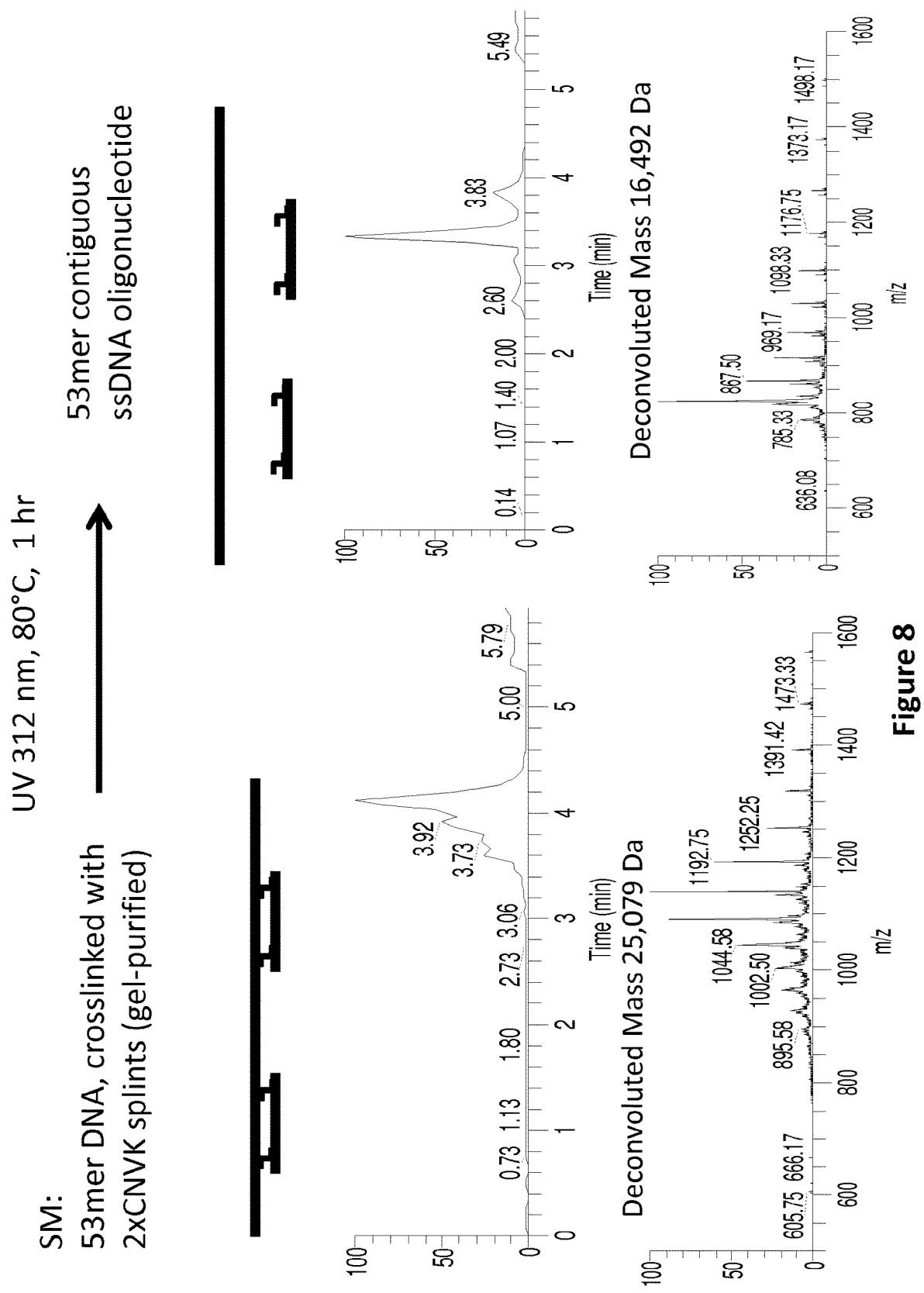
FIG. 8 shows the LCMS of the recovery of the starting Double_CNVK_template.

In order to study the dissociation of multiple CNVK-containing cross-linked oligonucleotides, we adapted the above protocol to prepare a complex with two CNVK oligos, CNVKJ and Splint_14_CNVK, (Splint_14_CNVK is CGAXCGTGTCAXCG, where X is CNVK, synthesized by Biosearch Technologies, CA), photochemically crosslinked to a single oligonucleotide, Double_CNVK_Template (AAAAAAGTCGTGACACGTCG-GAAAAAAAAAAAACGGTGACACGGTCGAAAAAA, IDT (IA)). This complex was analyzed by LCMS: observed MW 25,079 Da (calculated 25,055 Da). Then it was dissolved in water to 100 uM concentration and was irradiated by UV 312 nm for 1 hour at 80° C., again as described above. The products were analyzed by LCMS to find the recovery of the starting Double_CNVK_template: observed MW 16,492 Da (calculated 16,492 Da) (FIG. 8).

EXAMPLE 3

Ligation and Photochemical Un-Cross-Linking of Cyanovinylcarbazole Photochemically Cross-Linked Oligonucleotides to Model the Recovery of Sequence Information From Photochemically Cross-Linked Tags A complex of CNVK2_P_TagB, CNVK2_TagA and CNVKJ was prepared, photochemically cross-linked, and gel-purified as described in Example 2.

Figure 9:
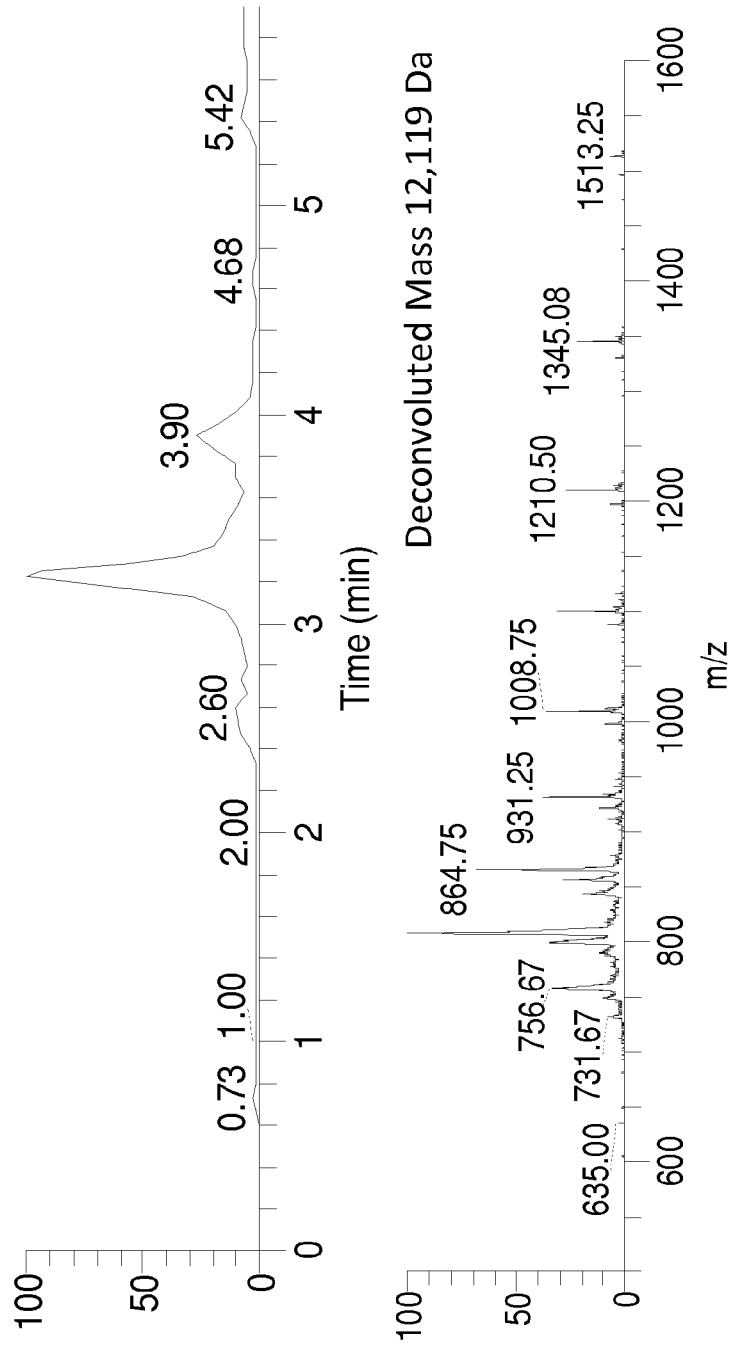
FIG. 9 shows the LCMS of treatment of a complex of CNVK2_P_TagB, CNVK2_TagA and CNVKJ with T4 DNA ligase.

The photochemically cross-linked model tag pair was dissolved in 1×T4 DNA Ligase buffer (NEB, MA) and was incubated with T4 DNA ligase (NEB, MA) for 1 hour at 37° C. The product of this reaction was then uncross-linked as described Example 2 and was analyzed by denaturing gel electrophoresis and LCMS (FIG. 9). The product of the ligation reaction was observed in high yield, observed MW 12,119 Da (calculated 12,119 Da).

Figure 10:
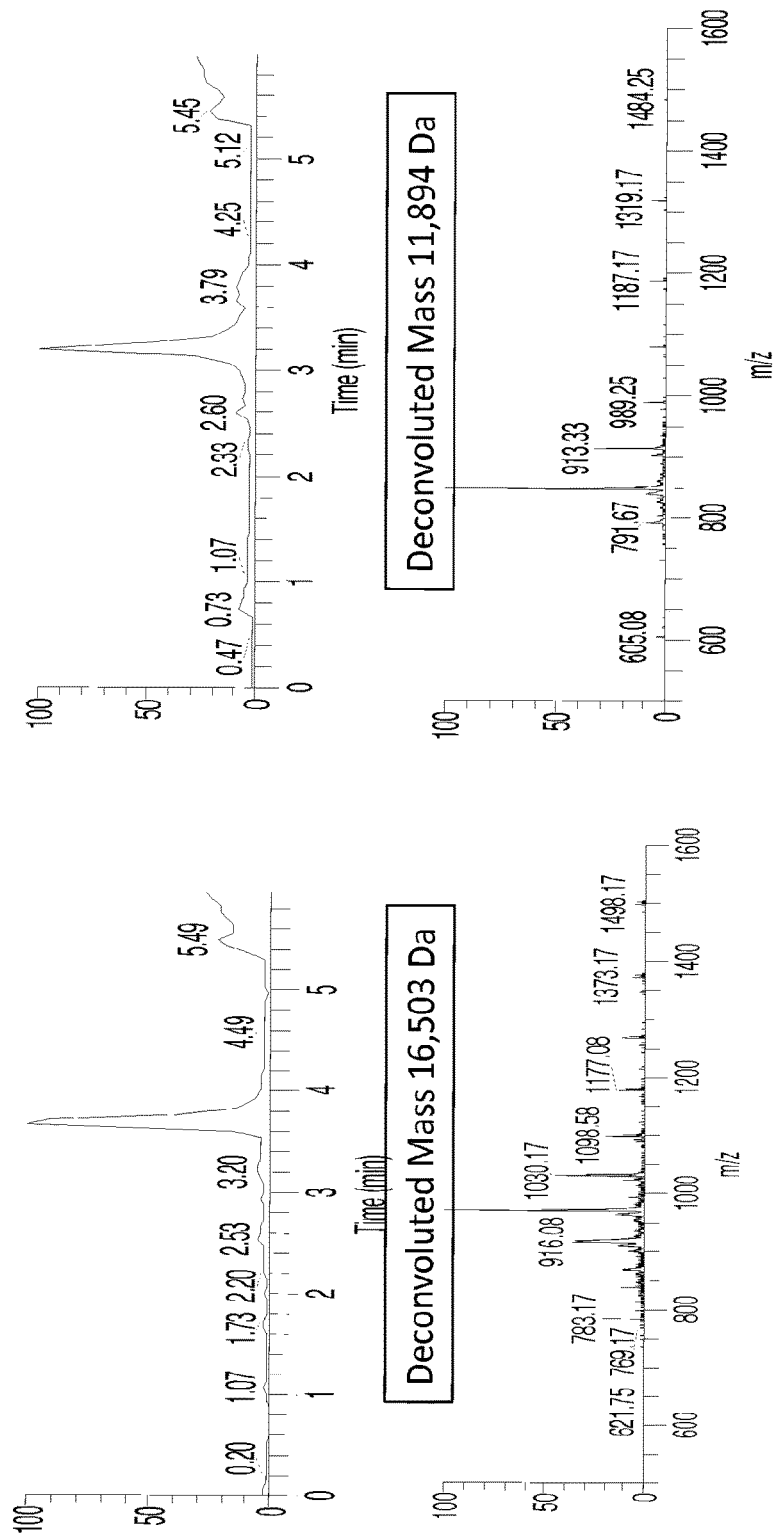
FIG. 10 shows the LCMS results of the phosphorylation-ligation reaction of photochemically cross-linked non-phosphorylated model tag pair CNVK2_NP_TagB with CNVK2_TagA and CNVKJ.

The corresponding photochemically cross-linked non-phosphorylated model tag pair CNVK2_NP_TagB with CNVK2_TagA and CNVKJ was also prepared, as described above. The LCMS analysis of this complex revealed an observed MW of 16,503 Da (calculated 16,499 Da, FIG. 10). The photochemically cross-linked complex was dissolved in 1×T4 Ligase buffer (NEB) and was incubated with a mixture of T4 Polynucleotide Kinase and T4 DNA Ligase (NEB) for 1 hour at 37° C. The product of this coupled phosphorylation-ligation reaction was then photochemically uncross-linked by irradiation with UV at 312 nm for 1 hour at 80° C. as described in Example 2. The product of this phosphorylation-ligation reaction was observed by denaturing gel electrophoresis and LCMS, revealing an observed MW of 11,894 Da (calculated MW 11,896 Da (additional phosphorylation at the 5' end of the ligated product)) (FIG. 10).

EXAMPLE 4

Figure 12:
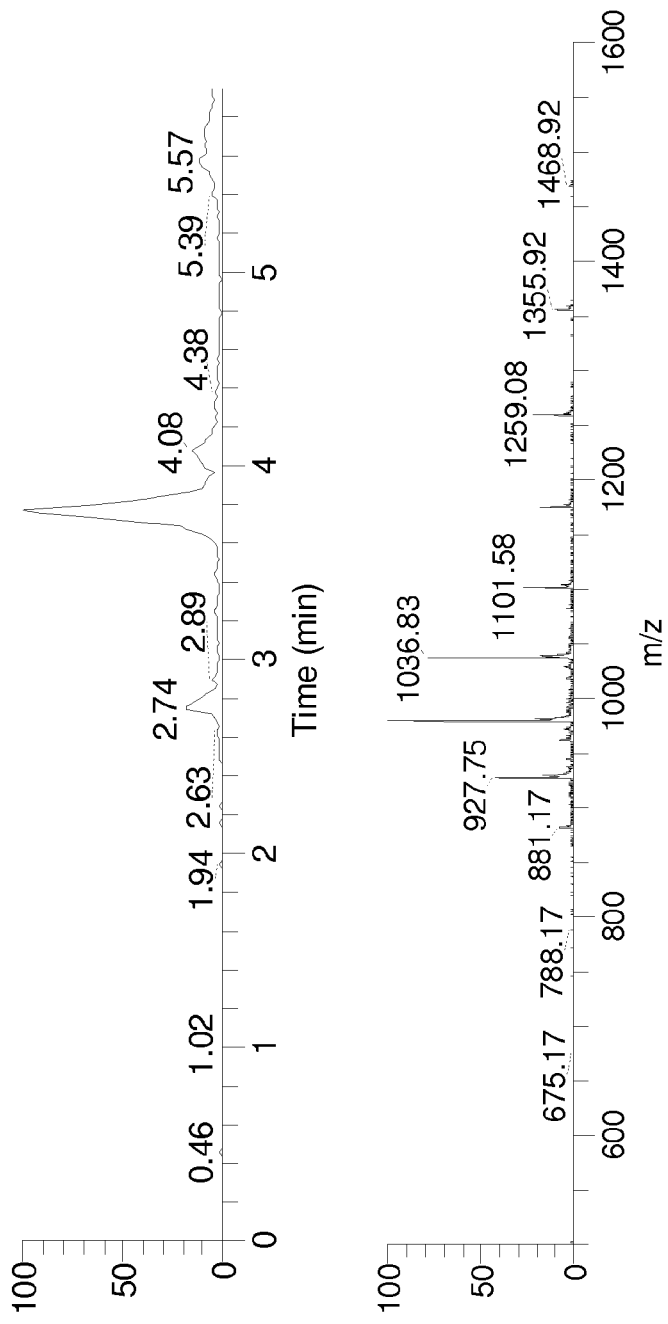
FIG. 12 shows the LCMS of the photochemical oligonucleotide cross-linking using psoralen within a stem to model one tagging event of Oligonucleotide 5PSO2_A9_TA, modified with C2-Psoralen at the 5'-terminus and Oligonucleotide PSO_HP_A9_TCT.

Photochemical Oligonucleotide Cross-Linking Using Psoralen Within a Stem to Model One Tagging Event Oligonucleotide 5PSO2_A9_TA, modified with C2-Psoralen at the 5'-terminus was obtained from Biosearch, CA (FIG. 11). Oligonucleotide PSO_HP_A9_TCT was obtained from IDT (IA) (FIG. 11). Both oligonucleotides were dissolved to 0.5 mM concentration each in 500 mM phosphate buffer at pH 7.0 and were annealed by heating to 95° C. and subsequently cooling to room temperature. The reaction was then irradiated with UV light at 365 nm at 4° C. using a UVL-21 compact UV lamp (UVP) for 30 minutes. The products were analyzed by LCMS. We observed rapid formation of the photochemically cross-linked product with an observed MW of 17,643 Da (calculated MW 17,643.4 Da, see FIG. 12).

EXAMPLE 5

Figure 13:
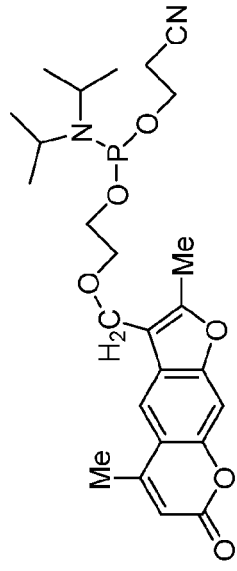
FIG. 13 shows Oligonucleotides Tag1_PsoCVU and SplintC_PsoC2 and Oligonucleotide SPSOC2_A9_GA (modified at 5'-terminus with C2 psoralen).

Photochemical Oligonucleotide Ligation Using Psoralen to Model One Tagging Event Oligonucleotides Tag1_PsoCVU and SplintC_PsoC2 were obtained from IDT (IA) (FIG. 13). Oligonucleotide 5PSOC2_A9_GA (modified at 5'-terminus with C2 psoralen) was obtained from Biosearch (CA) (FIG. 13).

Figure 14:
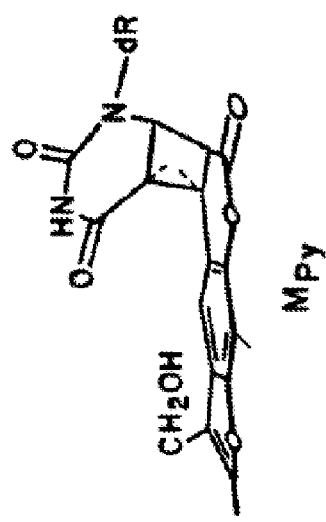
FIG. 14 shows a schematic of psoralen photoligation.

The photochemically ligated oligonucleotide conjugate of Tag1_PsoCVU and 5PSOC2_A9_GA was prepared as follows. Photoligation is achieved by the photochemical reaction of the 5'-psoralen pyrone moiety of one oligonucleotide with the 3' thymidine of a second oligonucleotide in the presence of a third oligonucleotide designed to hybridize to both of the first and second oligonucleotides and co-locate their reactive termini (FIG. 14).

Figure 15:
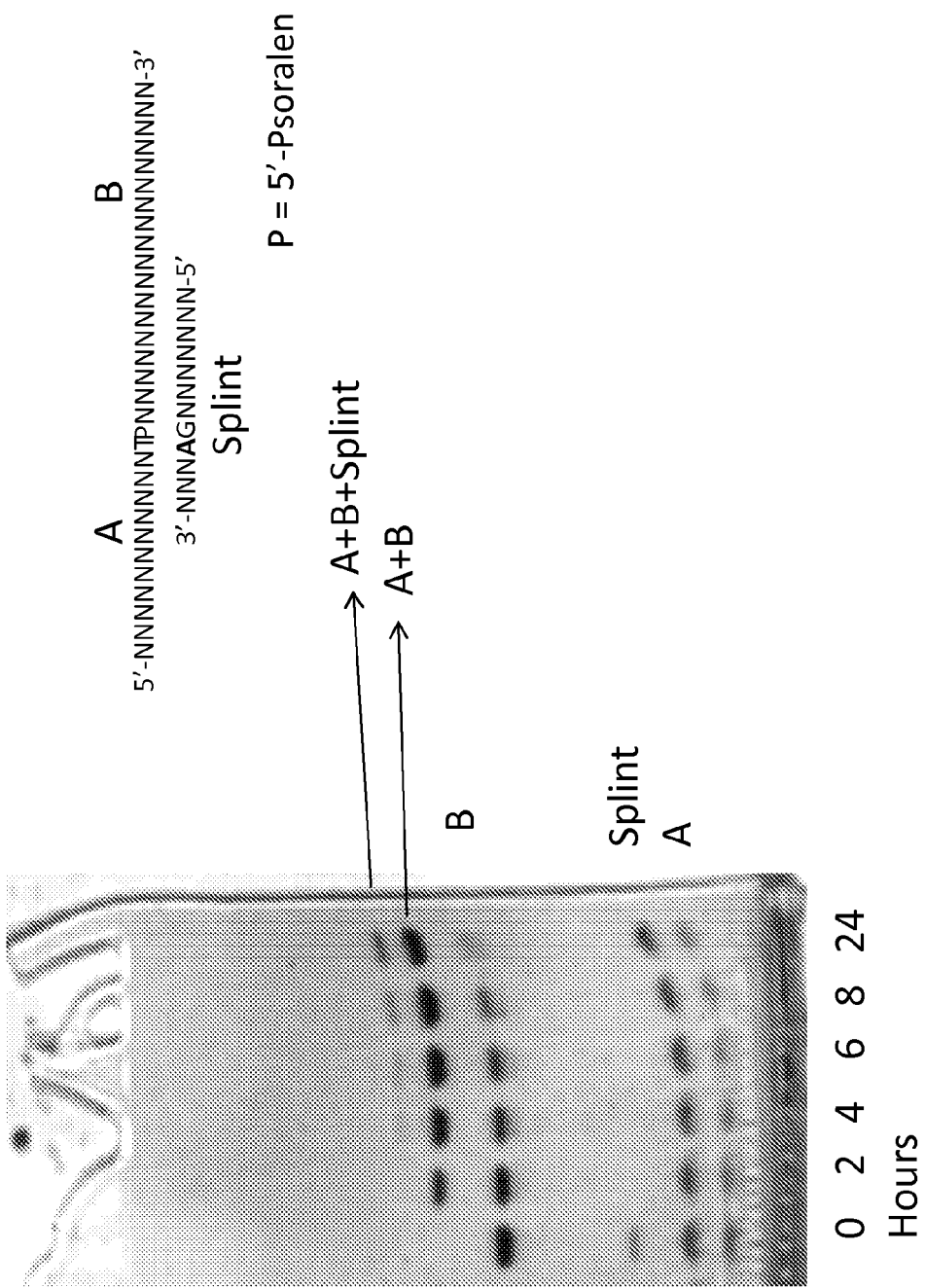
FIG. 15 shows a gel of the time-course of psoralen photoligation.

Photochemical ligation conditions were as follows: Oligonucleotides 5PsoC2_A9_GA (final 1 mM) and Tag1_PsoCVU (final 1.1 mM) and SplintC_PsoC2 (final 1.1 mM) were combined in a 10 uL photoligation reaction in 500 mM Phosphate buffer at pH 7.0 in 1.5 mL natural color polypropylene microcentrifuge tubes (Fisher Scientific, 02-682-550). The reaction mixture was first heated to 95° C. followed by slow cooling to room temperature. The reaction was then irradiated with UV light at 365 nm at 4° C. using a UVL-21 compact UV lamp (UVP). Aliquots of 1 uL were taken over a time-course and were analyzed on a 15% TBE/8M Urea denaturing polyacrylamide gel (FIG. 15). The gel was visualized and photographed using the UV shadowing of a fluorescent TLC plate. The photoligated conjugate of 5PsoC2_A9_GA and Tag1_PsoCVU formed at high yield. After 24 hours the yield is approximately 90% (FIG. 15).

Figure 16:
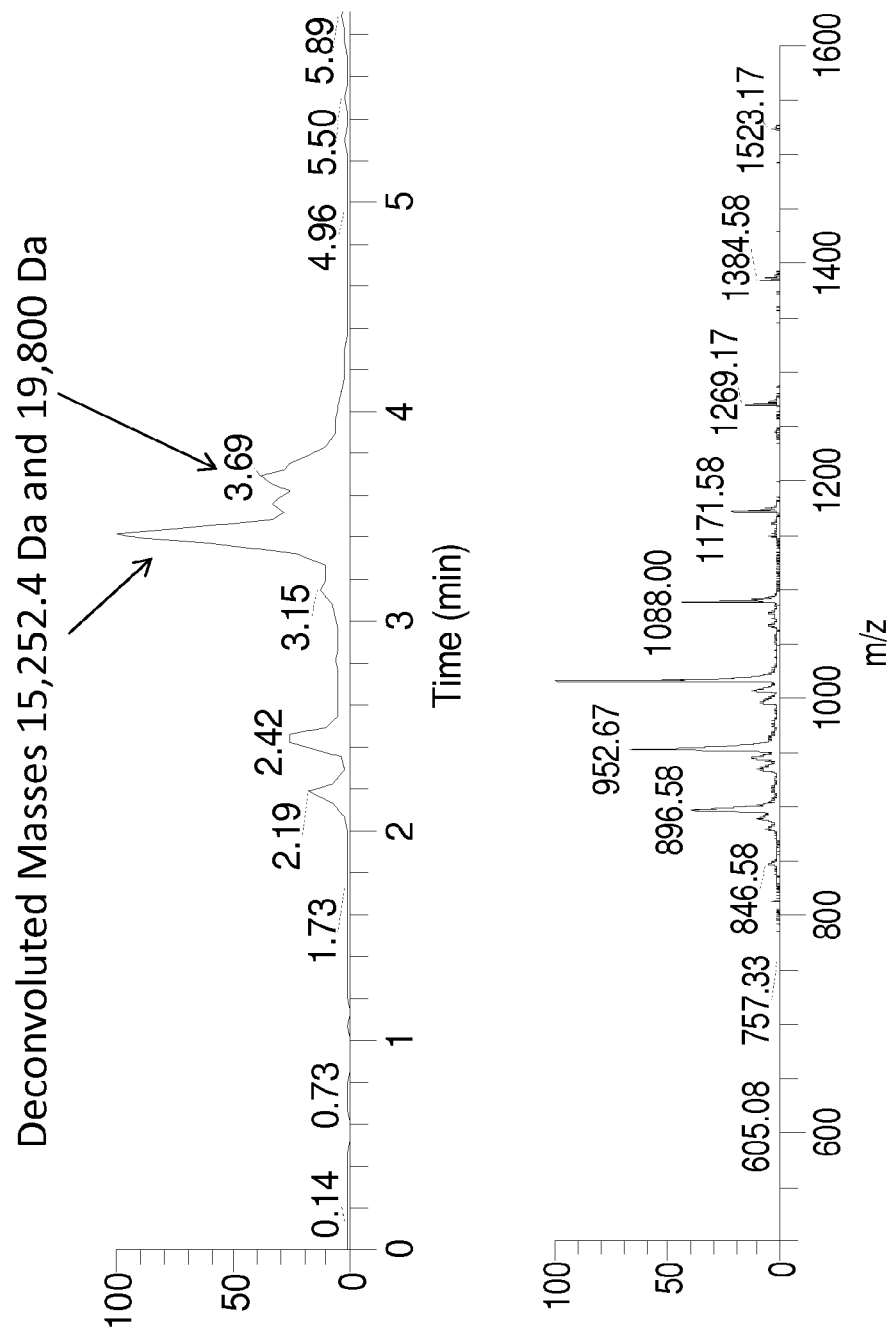
FIG. 16 shows the LCMS of the photoligated conjugate of 5PsoC2_A9_GA and Tag1_PsoCVU.

The 24-hour sample was analyzed by LCMS (FIG. 16). The major LC peak corresponded to the photoligated conjugate of 5PsoC2_A9_GA and Tag1_PsoCVU with an observed MW of 15,252.4 Da (calculated MW 15,243.1 Da).

Figure 17:
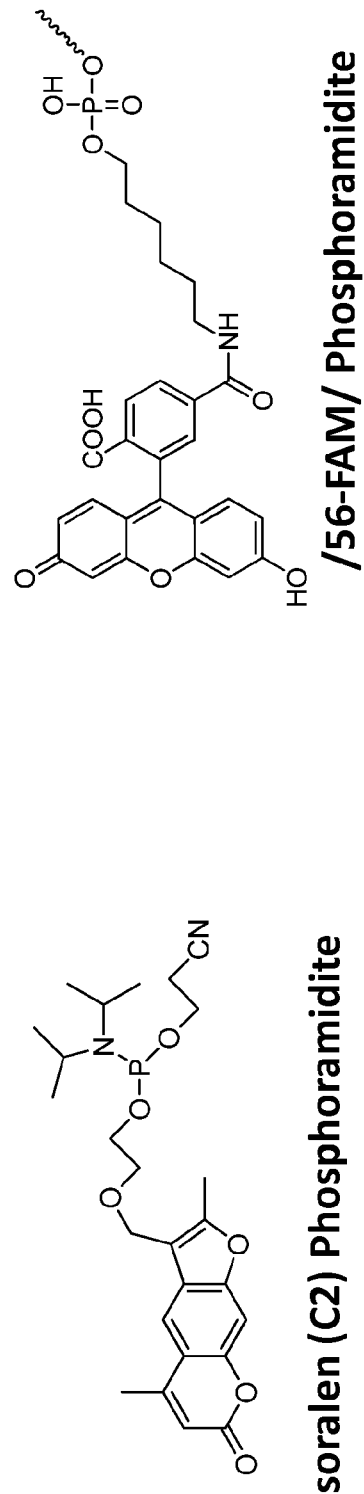
FIG. 17 shows a 5'-biotinylated oligonucleotide 5Bio_Tag_PsoCVU and a 5'-Psoralen oligonucleotide 5PsoC2_A9_GA along with a splint oligonucleotide SplintC_PsoC2.
Figure 18:
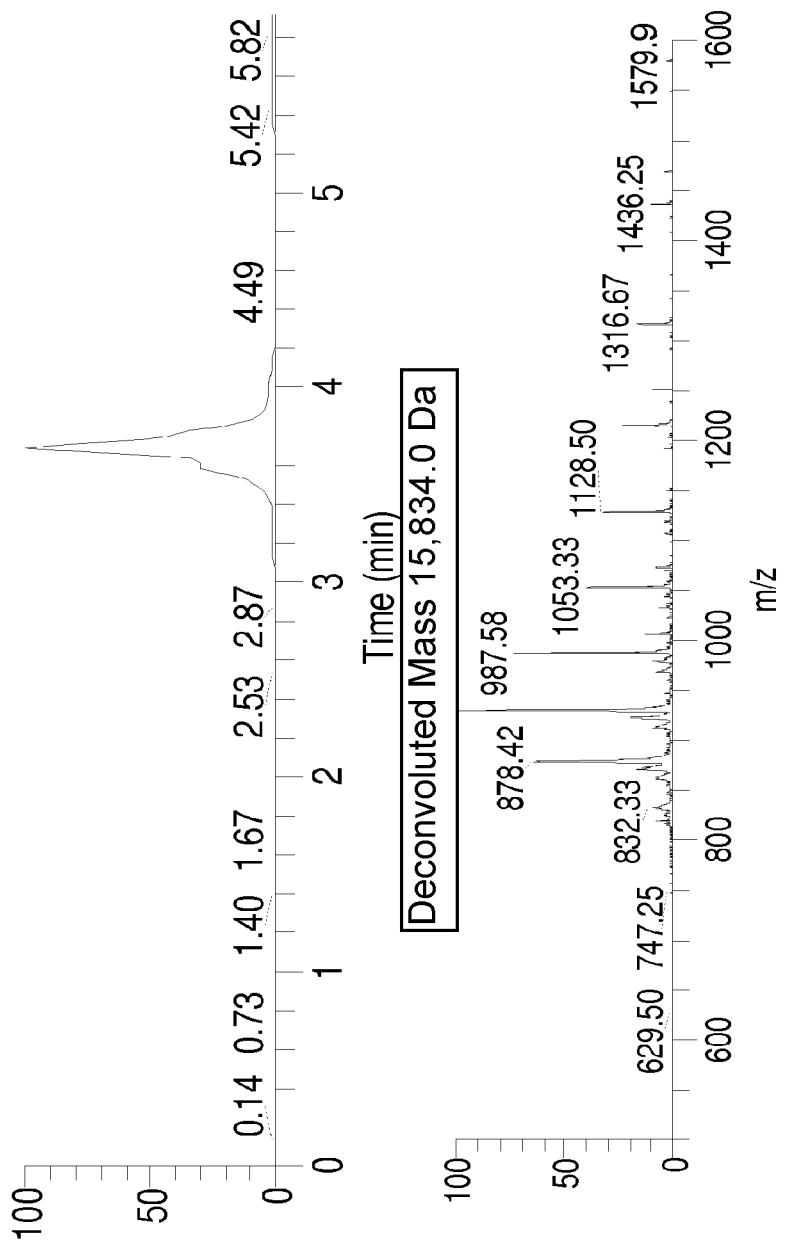
FIG. 18 shows the LCMS of a Psoralen-Thymidine photochemically ligated oligonucleotide conjugate (Bio_Pso).

EXAMPLE 6 cDNA Generation From Non-Polymerase-Readable Photochemically-Ligated Psoralen-Conjugated Model Tags Using Terminal Primer Extension, Non-Terminal Primer Extension, and Ligation to Model the Reading of a Single Tagging Event A Psoralen-Thymidine photochemically ligated oligonucleotide conjugate (Bio_Pso) was generated using a method similar to that described in Example 5 with the following two model tag oligonucleotides: a 5'-biotinylated oligonucleotide 5Bio_Tag_PsoCVU and a 5'-Psoralen oligonucleotide 5PsoC2_A9_GA along with a splint oligonucleotide SplintC_PsoC2, all three oligonucleotides were obtained from IDT (IA) and are shown in FIG. 17. After 24 hrs of the reaction Bio_Pso was purified on a 10% TBE-Urea denaturing PAAG and analyzed by LCMS, revealing a product with an observed MW of 15,834.0 Da (calculated MW 15,812.7 Da) (FIG. 18).

The Psoralen-Thymidine photochemically ligated oligonucleotide conjugate Bio_Pso was used as a template to generate cDNA by the enzymatic extension of both a terminal oligonucleotide primer (FAMprimer) and a non-terminal oligonucleotide primer (Phos-SplintC_PsoC2) with T4 DNA polymerase (NEB, MA). Phos-SplintC_PsoC2 was generated by the 5'-phosphorylation of SplintC_PsoC2 using T4 PNK (NEB, MA). The cDNA generation was conducted in a 100 uL reaction containing 10 uM each of FAMprimer, Phos-SplintC_PsoC2 and Bio_Pso in 1×T4 DNA ligase buffer (NEB, MA), supplemented with 1 mM of each dNTP and 10 uL of T4 DNA polymerase (NEB, MA). The reaction mixture was incubated at 37° C. for 1 hour and was then supplemented with 0.5 mM ATP and 5 uL of T4 DNA ligase (2,000 u/ul, NEB, MA) and then incubated for another 1 hour at 37° C.

The reaction mixture was then incubated with 200 uL of Streptavidin-coated DynaBeads M280 (Invitrogen, pre-washed with PBS for 1 hour at room temperature), the beads were washed with 1 mL of PBS and the product was eluted with 35 uL of 100 mM NaOH. The eluent was then neutralized by the addition of 5 uL of 1 M Tris HCl pH 7.0 and was analyzed by LCMS.

Figure 19:
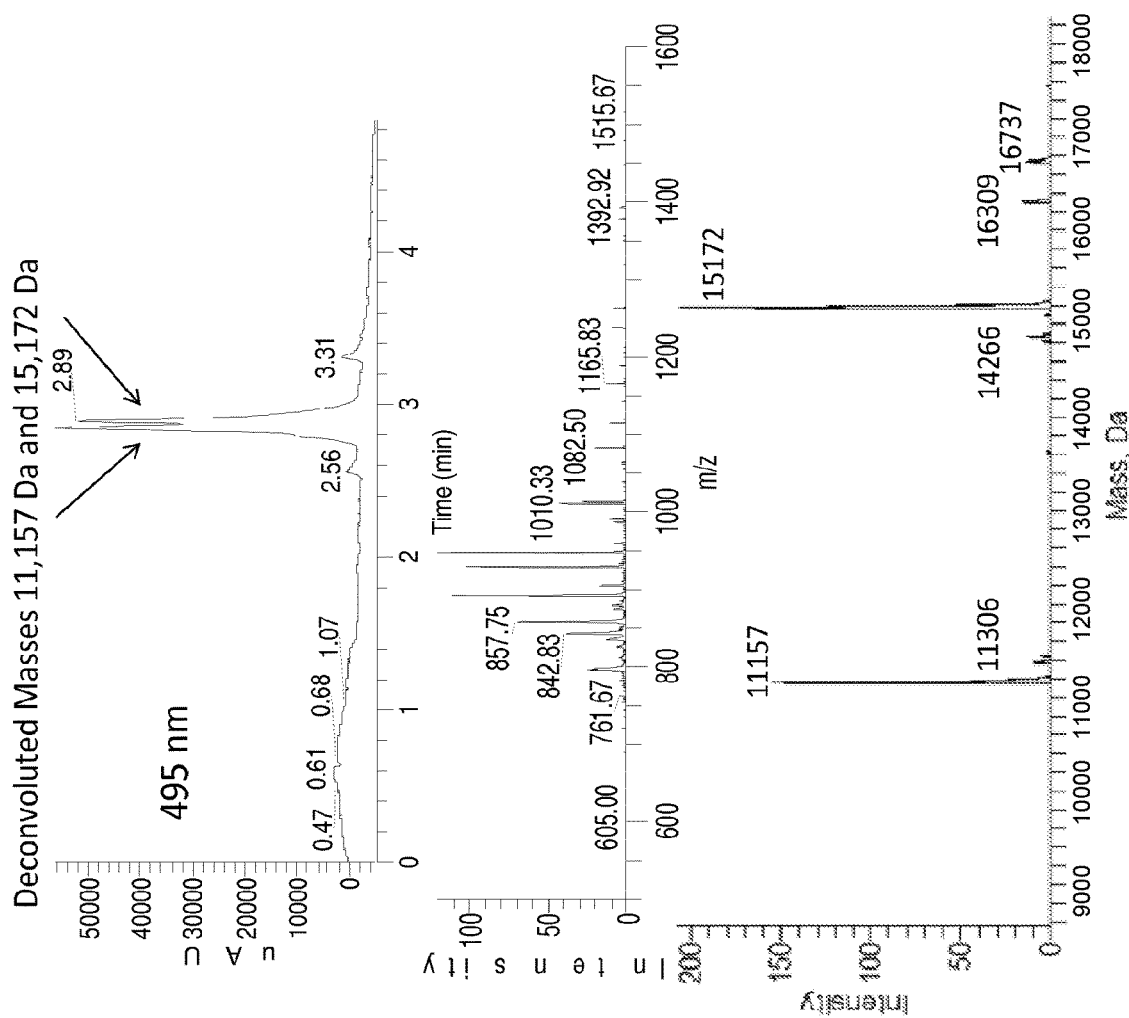
FIG. 19 shows the LCMS of cDNA generated from Bio_Pso using terminal and non-terminal primer extension and ligation.

LCMS analysis of the resultant product, with detection at 495 nm, showed that approximately 50% of the FAMprimer had been extended to the full-length complementary sequence to the Bio_Pso template minus a single dA nucleotide (observed MW 15,170 Da, expected full-length MW 15,458 Da). Most of the rest of the FAMprimer was extended up until the photochemical ligation junction (observed MW 11,154 Da, calculated MW 11,154 Da) (FIG. 19).

Figure 20:
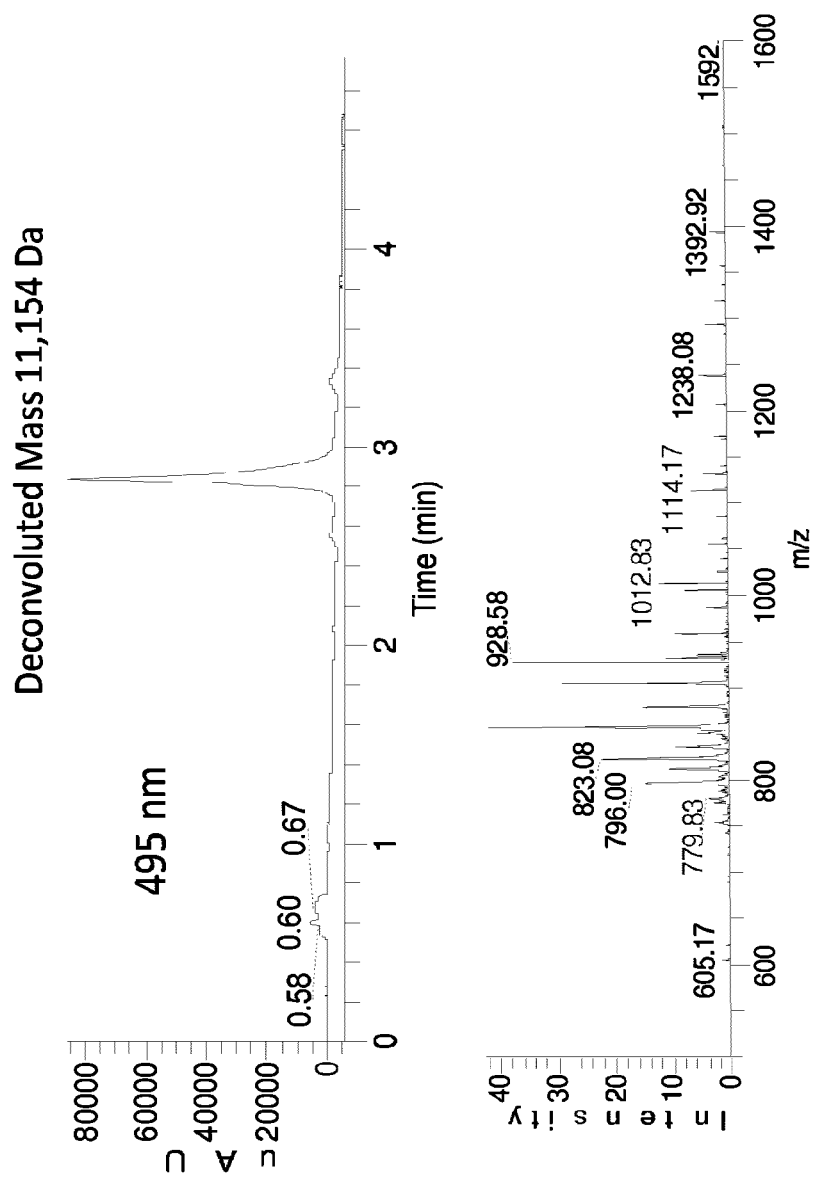
FIG. 20 shows the LCMS of no-ligation control of cDNA generated from Bio_Pso using terminal and non-terminal primer extension.

When the cDNA-generation, described above, was performed without addition of the ligase enzyme, the full-length complementary sequence (minus a single dA) was not observed (FIG. 20).

EXAMPLE 7

Figure 21:
FIG. 21 shows Oligonucleotides CVU_G and CVU_A and Oligonucleotides Tag1_PsoCVU, SplintC_CVU and SplintA_CVU.

Photochemical Oligonucleotide Ligation Using Carboxyvinyl Uridine to Model One Tagging Event Oligonucleotides CVU_G and CVU_A were synthesized by Trilink (CA) (FIG. 21). Both oligonucleotides are 5'-modified with a 5-(Carboxy)vinyl-2'-deoxyuridine (FIG. 21). Oligonucleotides Tag1_PsoCVU, SplintC_CVU and SplintA_CVU were obtained from IDT DNA (IA) (FIG. 21).

Figure 22:
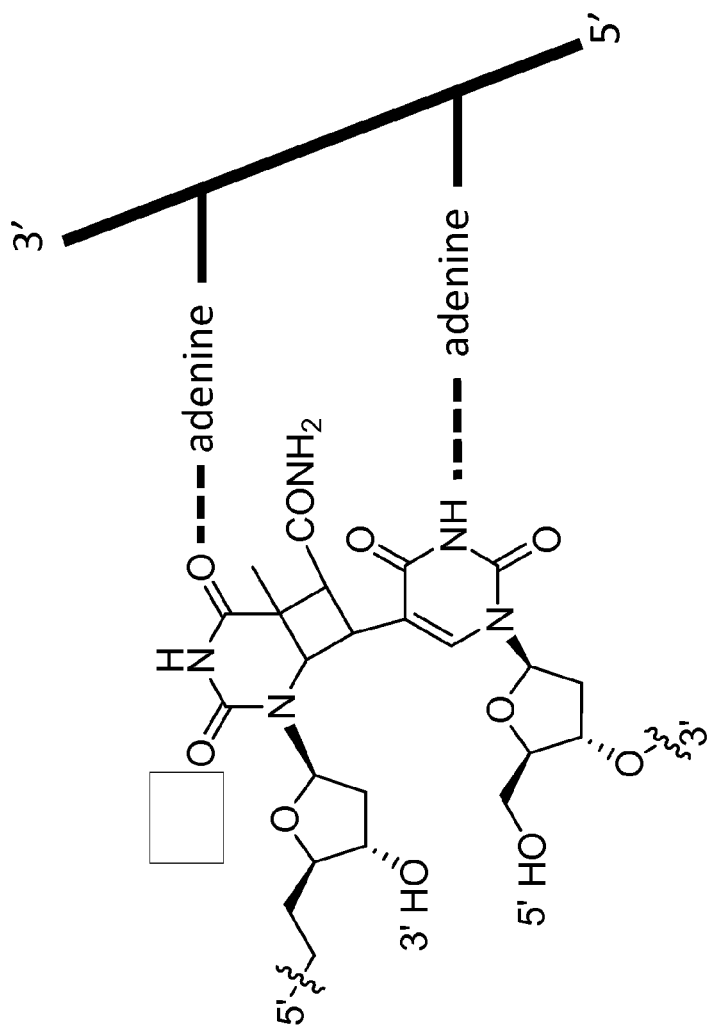
FIG. 22 shows the structure of the photochemical ligation junction formed between an irradiated 5'-5-(Carboxy)vinyl-2'-deoxyuridine and a 3'-Thymidine.

The structure of the photochemical ligation junction formed between an irradiated 5'-5-(Carboxy)vinyl-2'-deoxyuridine and a 3'-Thymidine is shown in FIG. 22.

Figure 23:
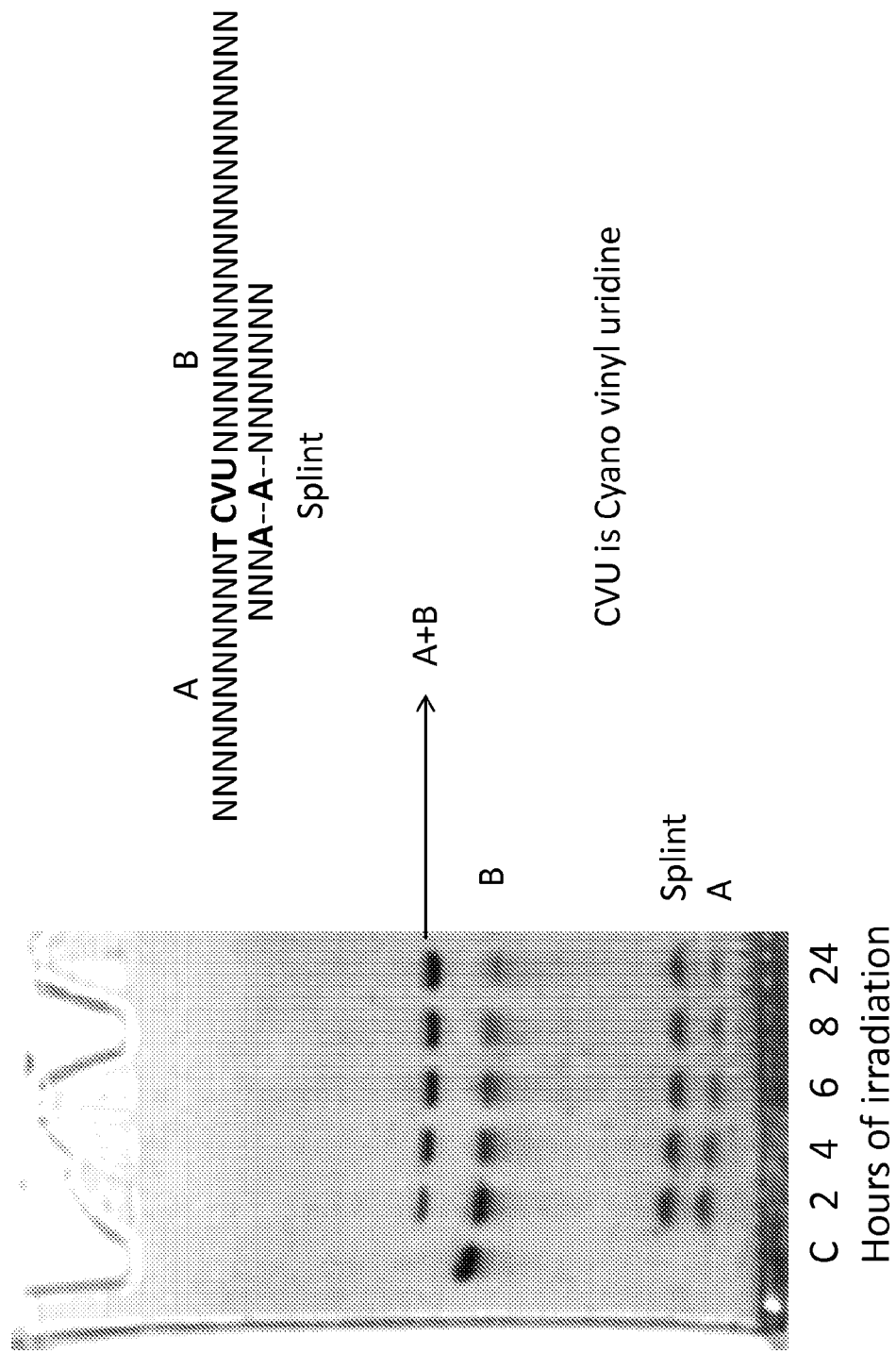
FIG. 23 shows a gel of the time-course of CVU photoligation at 365 nm.

A 10 uL photochemical ligation reaction mixture was generated with 1 mM CVU_G, 1.1 mM Tag1_PsoCVU and 1.1 mM SplintC_CVU dissolved in 500 mM Sodium Phosphate buffer pH 7.0 in a 1.5 ml natural color polypropylene microcentrifuge tubes (Fisher Scientific, 02-682-550). The reaction mixture was heated to 95° C. followed by slow cooling to the room temperature. The reaction was then irradiated by UV light at 365 nm for 24 hours at 4° C. using a UVL-21 compact UV lamp (UVP). Aliquots of 1 uL were taken over a time-course and were electrophoresed on a 15% TBE/8M Urea denaturing polyacrylamide gel (FIG. 23). The gel was visualized and photographed by UV shadowing of a fluorescent TLC plate. After 24 hours of irradiation over 90% of the CVU_G oligonucleotide had been photochemically ligated.

Figure 24:
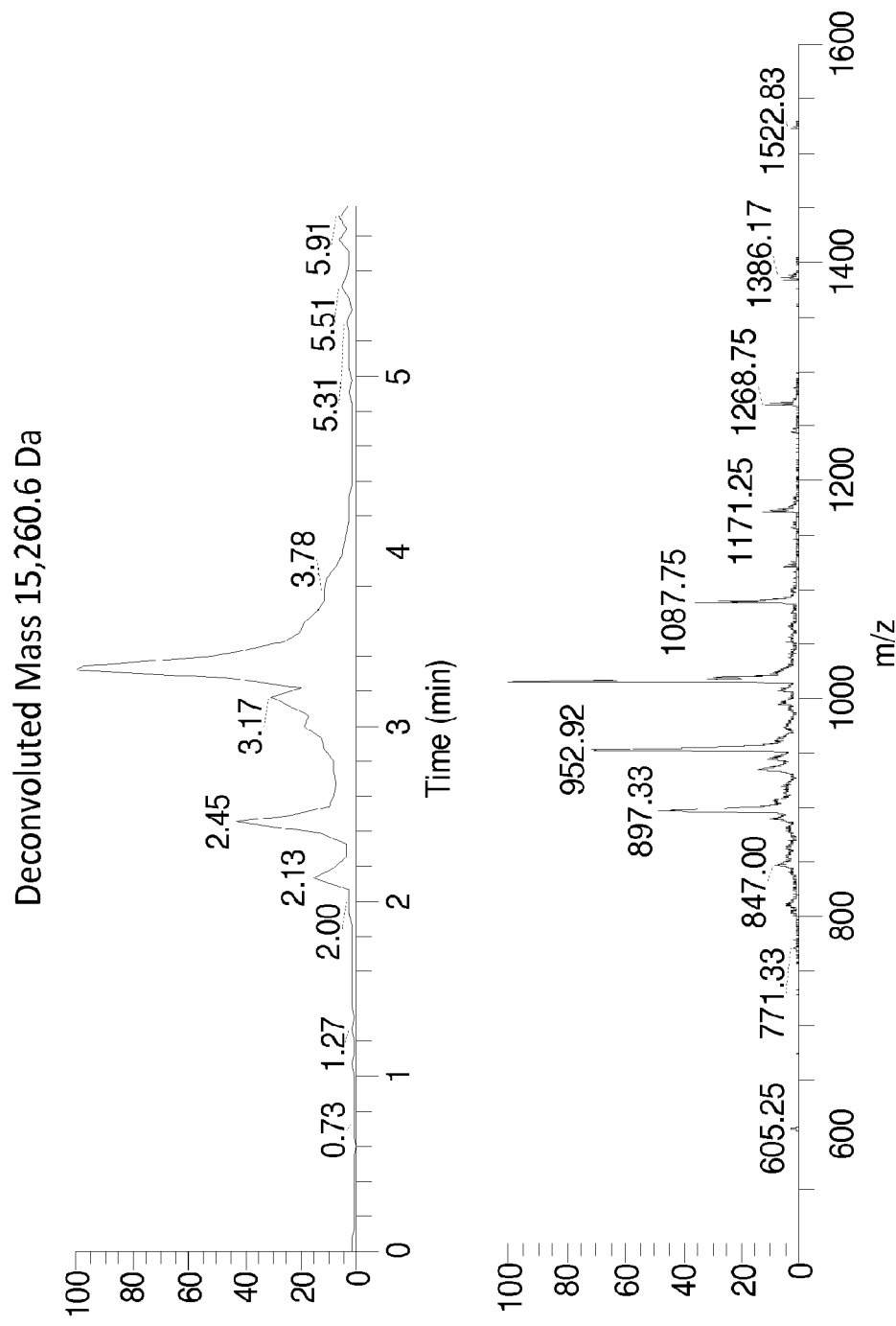
FIG. 24 shows the LCMS of photochemical ligation product of CVU_G with Tag1_PsoCVU.

The 24-hour sample was analyzed by LCMS (FIG. 24). The major peak corresponds to the photochemical ligation product of CVU_G with Tag1_PsoCVU. The observed MW was 15,260.6 Da (calculated MW 15,238.7 Da).

Figure 25:
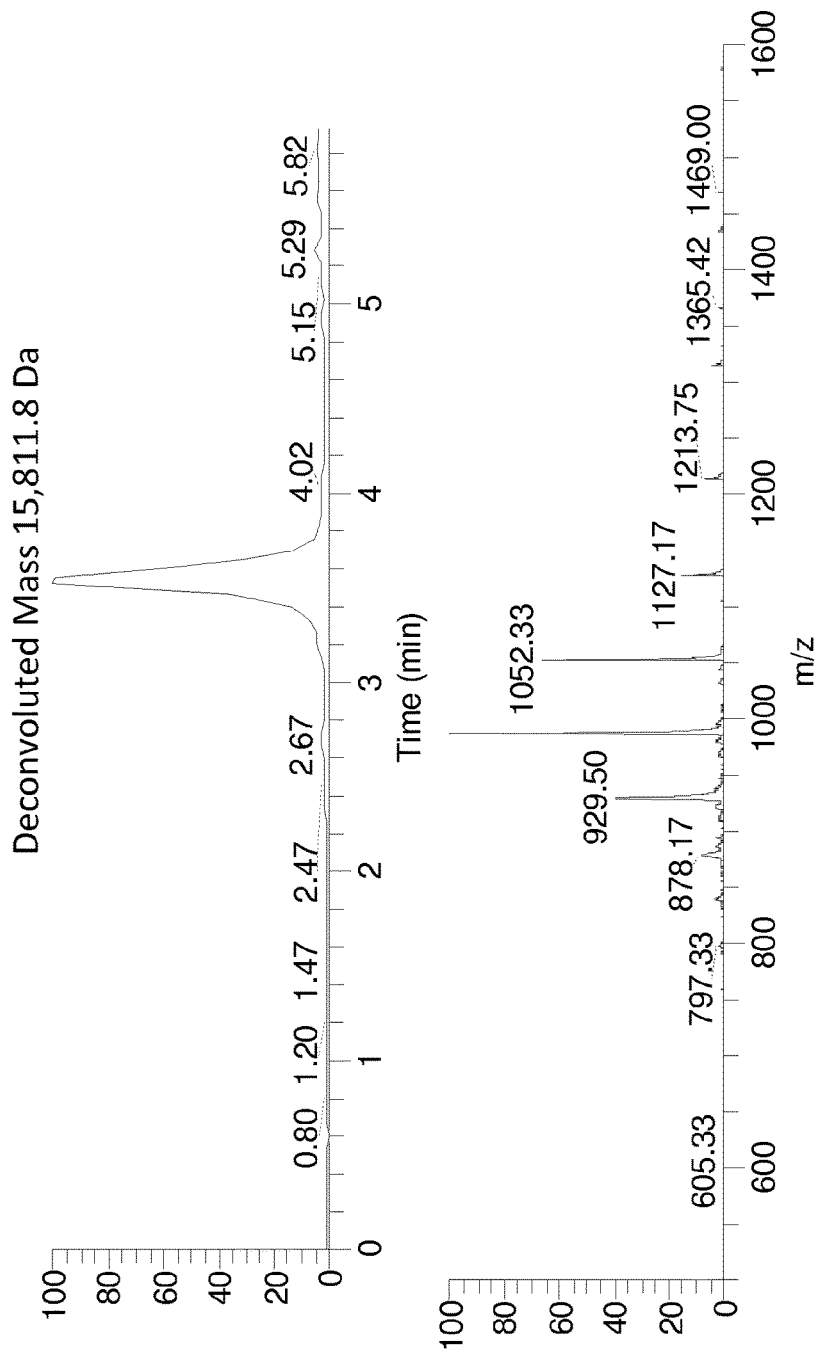
FIG. 25 shows the LCMS of a Carboxyvinyl Uridine-Thymidine photochemically-ligated oligonucleotide conjugate (Bio_CVU).

EXAMPLE 8 cDNA Generation From Non-Polymerase-Readable Photochemically-Ligated Carboxyvinyl Uridine-Conjugated Model Tags Using Terminal Primer Extension, Non-Terminal Primer Extension, and Ligation to Model the Reading of a Single Tagging Event A Carboxyvinyl Uridine-Thymidine photochemically-ligated oligonucleotide conjugate (Bio_CVU) was generated using a method similar to that described in Example 7 with the following two model tag oligonucleotides: A 5'-5-Carboxyvinyl Uridine oligonucleotide 5'-CVU_A and a 5'-Biotinylated oligonucleotide 5Bio_Tag_PsoCVU along with a splint oligonucleotide SplintA_CVU, all three oligonucleotides were obtained from IDT (IA) and are shown in FIGS. 21 and 25. The reaction product was gel-purified as described in Example 6 and LCMS analysis revealed a product with an observed MW of 15,811.8 Da (calculated MW 15,792.3 Da) (FIG. 25).

The Carboxyvinyl Uridine-Thymidine photochemically-ligated oligonucleotide conjugate Bio_CVU was used as a template to generate cDNA by the enzymatic extension of both a terminal oligonucleotide primer (FAMprimer) and a non-terminal oligonucleotide primer (Phos-SplintA_CVU) with T4 DNA polymerase (NEB, MA). Phos-SplintA_CVU was generated by the 5'-phosphorylation of SplintA_CVU using T4 PNK (NEB, MA). The cDNA generation was conducted in a 100 uL reaction containing 10 uM each of FAMprimer, Phos-SplintA_CVU and Bio_CVU in 1×T4 DNA ligase buffer (NEB, MA), supplemented with 1 mM of each dNTP and 10 uL of T4 DNA polymerase (NEB, MA). The reaction mixture was incubated at 37° C. for 1 hour and was then supplemented with 0.5 mM ATP and 5 uL of T4 DNA ligase (2,000 u/ul, NEB, MA) and then incubated for another 1 hour at 37° C.

The reaction mixture was then incubated with 200 uL of Streptavidin-coated DynaBeads M280 (Invitrogen, pre-washed with PBS for 1 hour at room temperature), the beads were washed with 1 mL of PBS and the product was eluted with 35 ul of 100 mM NaOH. The eluent was then neutralized by the addition of 5 uL of 1 M Tris HCl pH 7.0 and was analyzed by LCMS.

Figure 26:
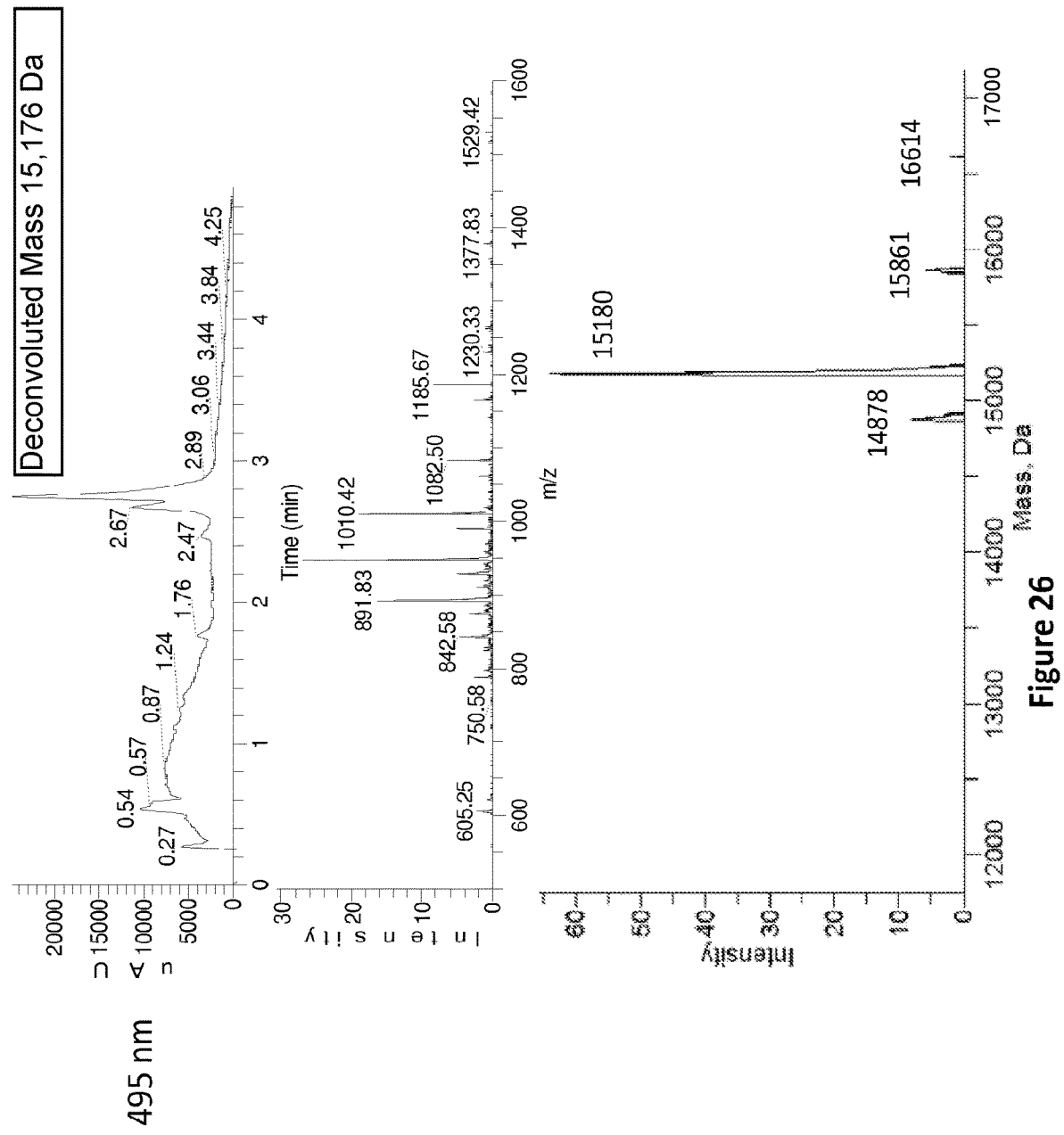
FIG. 26 shows the LCMS of Bio_CVU template minus a single dA nucleotide.

LCMS analysis of the resultant product, with detection at 495 nm, showed that approximately 80% of the FAMprimer had been extended to the full-length complementary sequence to the Bio_CVU template minus a single dA nucleotide (observed MW 15,176 Da, calculated full-length MW 15,458 Da). Most of the rest of the FAMprimer was extended up until three nucleotides before the photochemical ligation junction (observed MW 10,560 Da, calculated MW 10,559 Da) (FIG. 26).

When the cDNA-generation, described above, was performed without addition of the ligase enzyme, the full-length complementary sequence (minus a single dA) was not observed.

EXAMPLE 9

Figure 27:
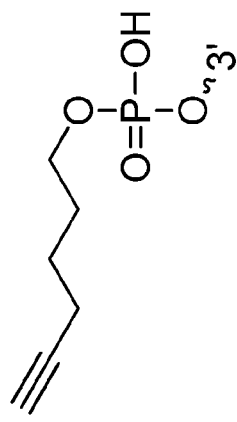
FIG. 27 shows Oligonucleotides S_IDTN$_3$ and S_ID-Talkyne.

Oligonucleotide Ligation Using a Non-Polymerase-Readable Click-Conjugation to Model One Tagging Event Oligonucleotides S_IDTN$_3$ and S_IDTalkyne were obtained from IDT (IA) (FIG. 27). The 3'-azide modification of oligonucleotide S_IDTN$_3$ is an IDT proprietary modification (3' IDT azide modification /3AzideN/ (MW 350)).

Oligonucleotides containing the /3AzideN/ modification were HPLC-purified.

Oligonucleotides containing the Hexynyl modification were desalted and used without further purification.

Figure 28:
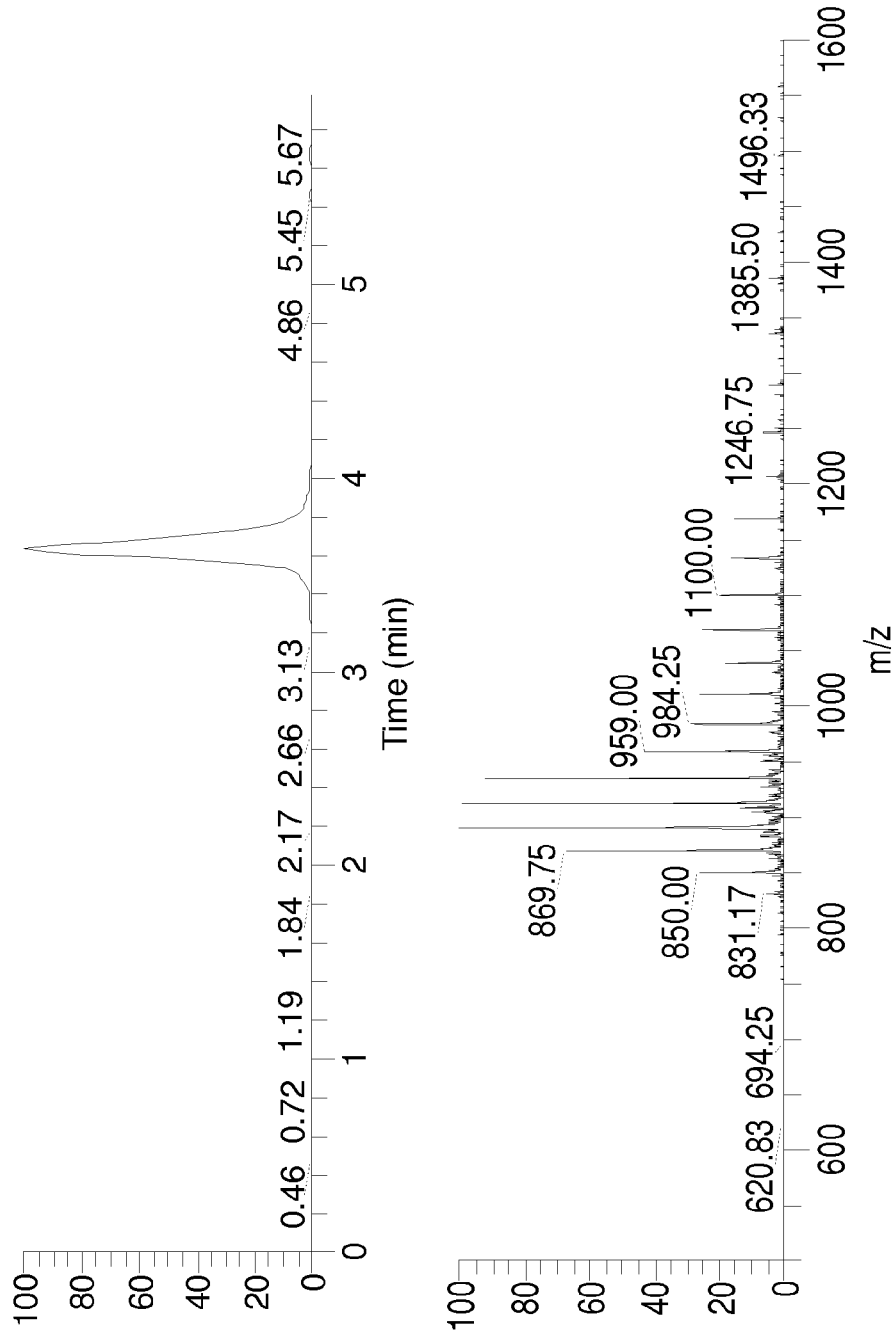
FIG. 28 shows LCMS analysis of the gel purified conjugate of S_IDTN$_3$ and S_IDTalkyne.

Click-conjugation of these model tags was achieved by a Cu (I) catalyzed 3+1 azido alkyne cycloaddition as follows:

Stock solutions were prepared as follows: Cu(OAc)$_2$.H$_2$O (FW 181.6), 10 mM in DMF; Sodium Ascorbate (FW 198.1), 20 mM in H$_2$O and Tris-(BenzylTriazolylmethyl) Amine (TBTA) (FW 530.6), 10 mM in DMF. To an Eppendorf tube was added 10 uL pH 7.0 phosphate buffer (500 mM aqueous solution), 10 uL of S_IDTalkyne (1 mM aqueous solution, 10 nmol, 1 equivalent) and 10 uL S-IDTN$_3$ (1 mM aqueous solution, 10 nmol, 1 molar equivalent). To this solution was added 5 uL of Cu_Pre-mix (2 molar equivalents of Cu(OAc)$_2$, 4 molar equivalents of sodium ascorbate, 1 molar equivalent of TBTA). The reaction was incubated at room temperature overnight. The product was analyzed by LCMS (Thermo) (FIG. 28) and the MW was found to be 26,304.8 Da (calcd: 26311.2 Da). The conjugate was further purified by electrophoresis using 10% PAAG/8M urea. This conjugation product was named Conjugate_Click_S.

EXAMPLE 10

Figure 29:
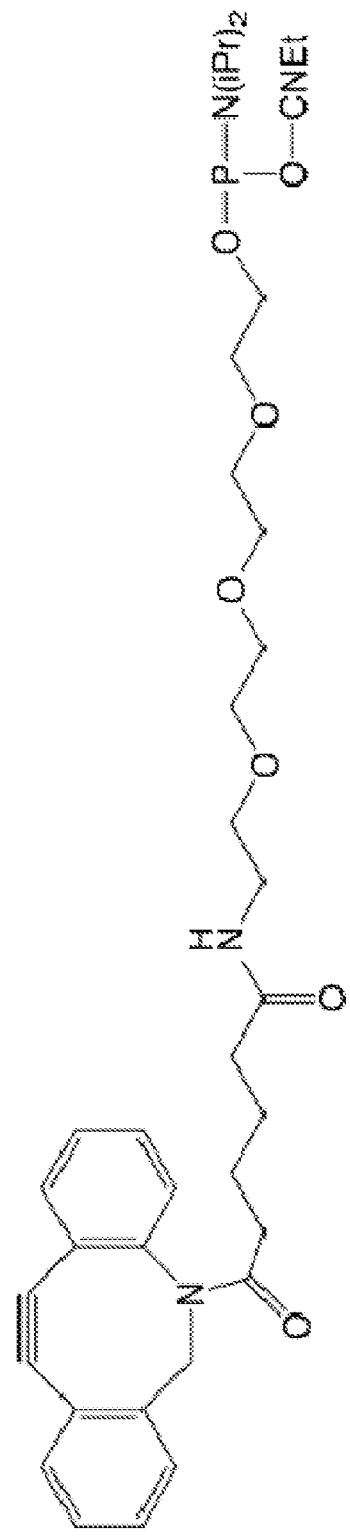
FIG. 29 shows TKR_Central and S_IDTN$_3$ oligos and 5'-dibenzo-cyclooctyne (DBCO)-modified oligo TKR_DBCO_S.

Oligonucleotide Ligation Using a Pair of Orthogonal Non-Polymerase-Readable Click-Conjugations to Model a Pair of Orthogonal Tagging Events TKR_Central and and S_IDTN$_3$ oligos were obtained from IDT (FIG. 29). The 5'-dibenzo-cyclooctyne (DBCO)-modified oligo TKR_DBCO_S was obtained from Biosearch Technologies (CA) (FIG. 29).

Figure 30:
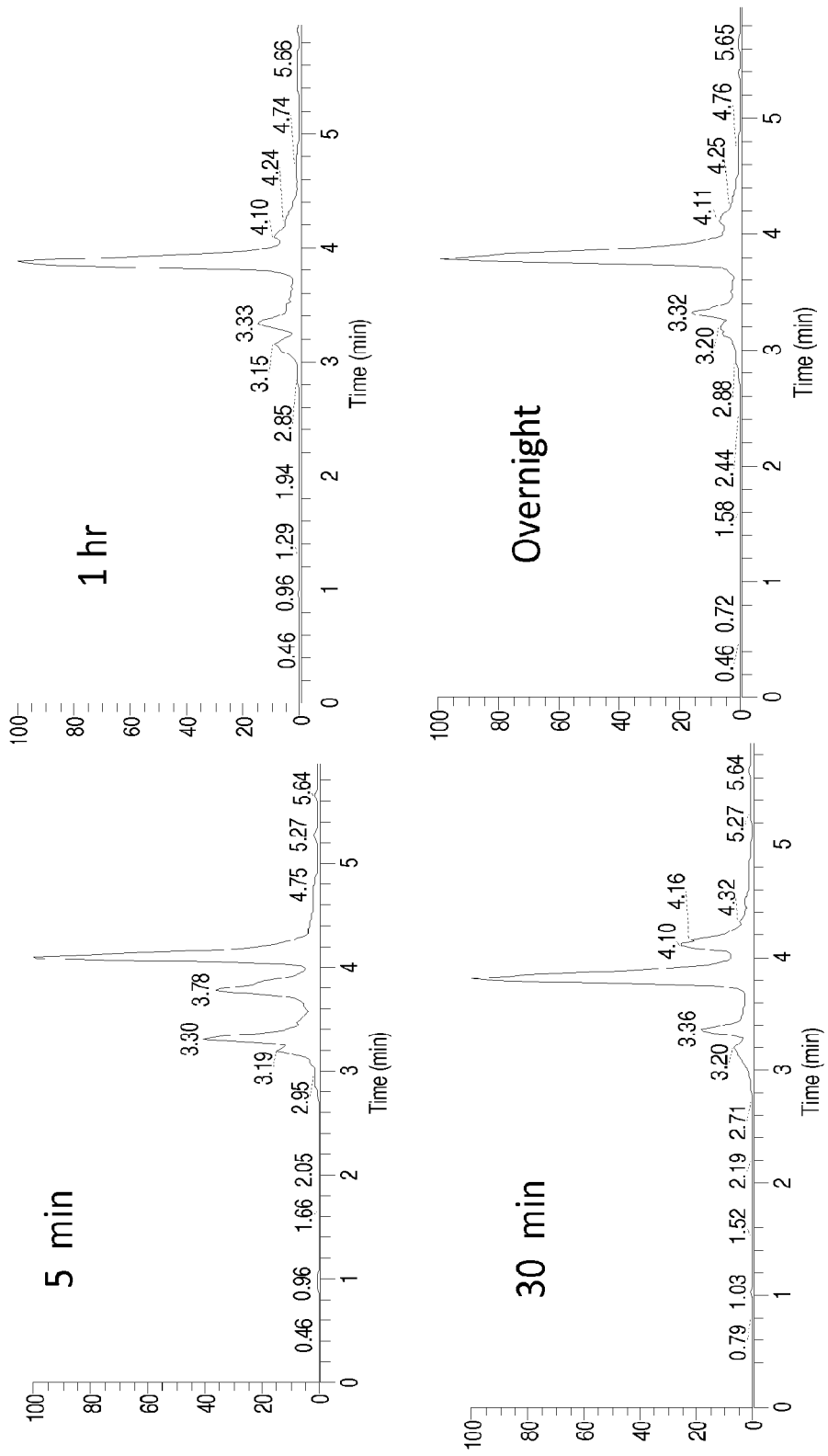
FIG. 30 shows the LCMS time course of the copper-free click reaction between TKR_DBCO_S and TKR_Central.

Firstly, a click conjugation was performed with TKR_Central and TKR_DBCO_S using a cyclooctyne-based copper-free click reaction. Equal molar amounts of each oligonucleotide (10 uL of 1 mM aqueous solutions) were mixed together in 0.2M sodium phosphate buffer at pH 7.0. The reaction progress was monitored by LCMS. The reaction was complete in 30 to 60 min, yielding over 90% of the pure conjugate. MS indicated a MW of 25,336 Da (calculated 25,341.8 Da) (FIG. 30).

Secondly, a click conjugation was performed between the conjugation product of TKR_Central and TKR_DBCO_S with S_IDTN$_3$ using the Cu (I) catalyzed click procedure described in Example 9. The resulting final conjugate, 2cl_S was purified on a 10% TBE/8M urea polyacrylamide gel and was analyzed by LCMS (Thermo) revealing the expected molecular weight for 2cl_S 38578.1 Da, (calculated 38560.4 Da) (FIG. 31).

EXAMPLE 11

PCR-Amplification of cDNA Derived From Non-Polymerase-Readable Click-Conjugated Model Tags Using Non-Terminal-Primer-Mediated Recombination in Free Solution and in Emulsified Aqueous Droplets to Model the Reading of Sequence Information From Chemically Conjugated Tags Conjugate_Click_S (FIG. 32), was prepared by the conjugation of of S_IDTN$_3$ and S_IDTalkyne, as described in Example 9.

Conjugate_Click_L (FIG. 32) was prepared by the conjugation of L_IDTN$_3$: TGCGGTCTAACTGTCTAGGCACTTGTTCGTTTGCCAGTGTGAGGAATGAACAGG/3AzideN/ and L_IDTalkyne: /5hexynyl/TACCGAATTGCCTTCCTCGTACAGTTCTAAGGCGCTTGGACACCACTTCAATCGGGTGCTATG CTT (IDT, IA) similarly to the conjugation protocol described in Example 10. LCMS after gel purification confirmed the MW as 37,582.6 Da (calculated 37,584.4 Da).

Oligodeoxynucleotide primers, including forward primer: TGCGGTCTAACTGTCTA, reverse primer: AAG CAT-AGCACCCGATT and ePsplint: GGCAAT-TCGGTACCTGTTCATTCC were obtained from (IDT, IA).

The conjugates Conjugate_Click_L and Conjugate_Click_S were each diluted to 1 nM and were used as templates for a splint-dependent-recombination-mediated cDNA generation/PCR amplification using Deep Vent (exo-) DNA polymerase (NEB, MA). A 50 uL Deep Vent (exo-) reaction was prepared as follows: 5 uL of 10× Thermopol buffer; 2.5 uL of a 10 uM solution of each forward and reverse primer, 1 uL of 100 nM ePsplint primer; 2.5 uL 10 mM dNTP mix (NEB); 5 uL of a 2 nM dilution of either conjugate or their 1:1 mixture, 2.5 uL Deep Vent (exo-) and water to 50 uL. The reaction was cycled 24 times as follows: 30 seconds at 94° C., 30 seconds at 52° C. and 60 seconds at 72° C.

Figure 33:
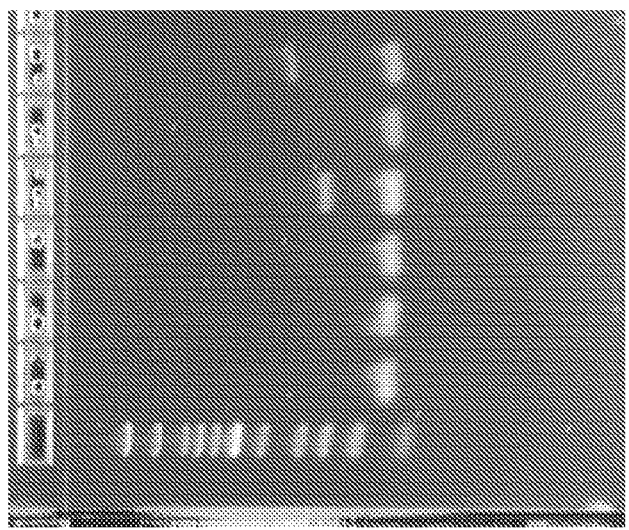
FIG. 33 shows splint-dependent-recombination-mediated cDNA generation/PCR amplification of Conjugate_Click_L and Conjugate_Click_S by Deep Vent (exo-) polymerase in the presence and absence of ePsplint. 24 cycles, 200 pM starting conjugate concentration. 1—Marker; 2—no template; 3—no template+ePsplint; 4—Conjugate_Click_S; 5—Conjugate_Click_S+ePsplint; 6—Conjugate_Click_L; 5—Conjugate_Click_L+ePsplint.
Figure 34:
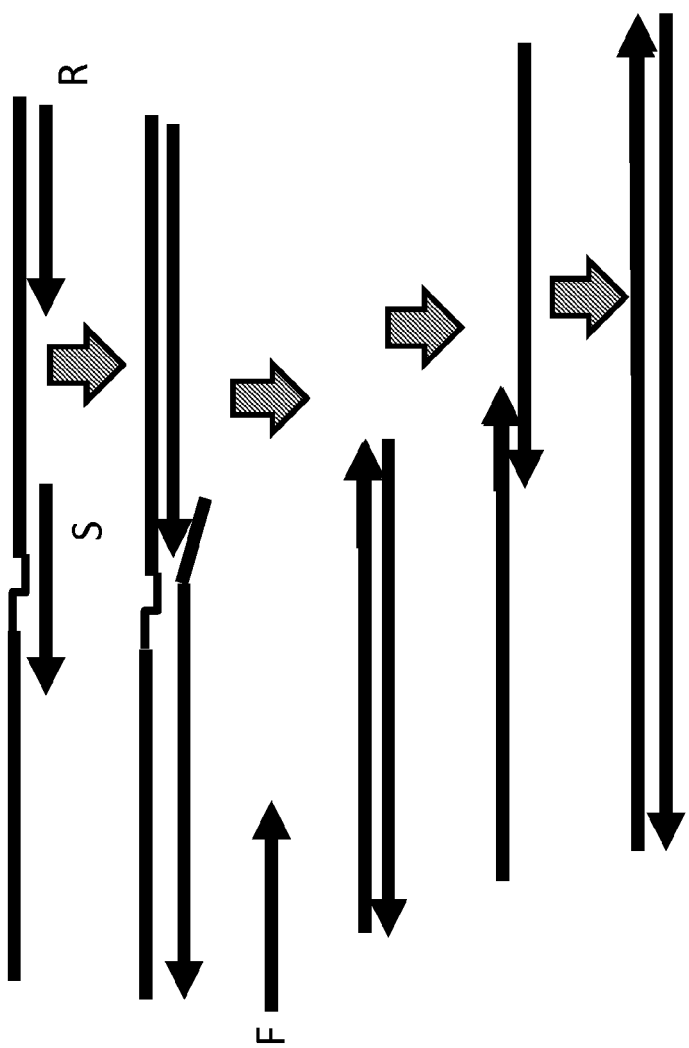
FIG. 34 shows the proposed mechanism of splint-dependent-recombination-mediated cDNA generation/PCR amplification.

When Conjugate_Click_L or Conjugate_Click_S conjugates are amplified separately in free solution in the presence of both terminal primers and the splint primer "ePsplint" and then evaluated by electrophoresis, each gives rise to a single product of with a mobility that correlates with the length of the template (lanes 5 and 7 in FIG. 33). Similar amplifications in the absence of the splint primer "ePsplint" gave no product (lanes 4 and 6 in FIG. 33). This suggests that splint-dependent-recombination-mediated cDNA generation/PCR amplification of both conjugates by Deep Vent (exo-) polymerase is dependent on the presence of ePsplint primer (FIG. 33). A possible mechanism for this recombination and amplification is presented in FIG. 34.

Figure 35:
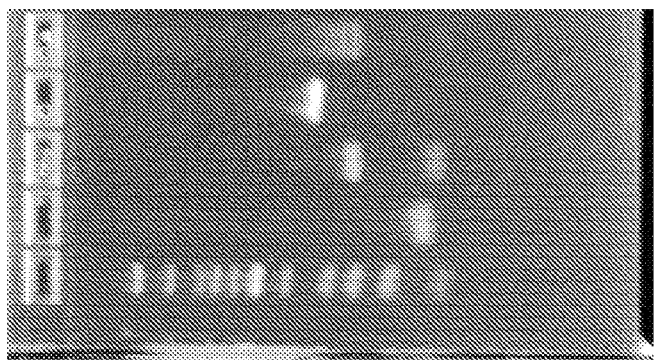
FIG. 35 shows splint-dependent-recombination-mediated cDNA generation/PCR amplification of Conjugate_Click_S and Conjugate_Click_L by Deep Vent exo-polymerase both separately and mixed together in free solution. All reactions supplemented with ePsplint. 1—Marker; 2—no template; 3—Conjugate_Click_S; 4—Conjugate_Click_L; 5—Conjugate_Click_S and Conjugate_Click_L.
Figure 36:
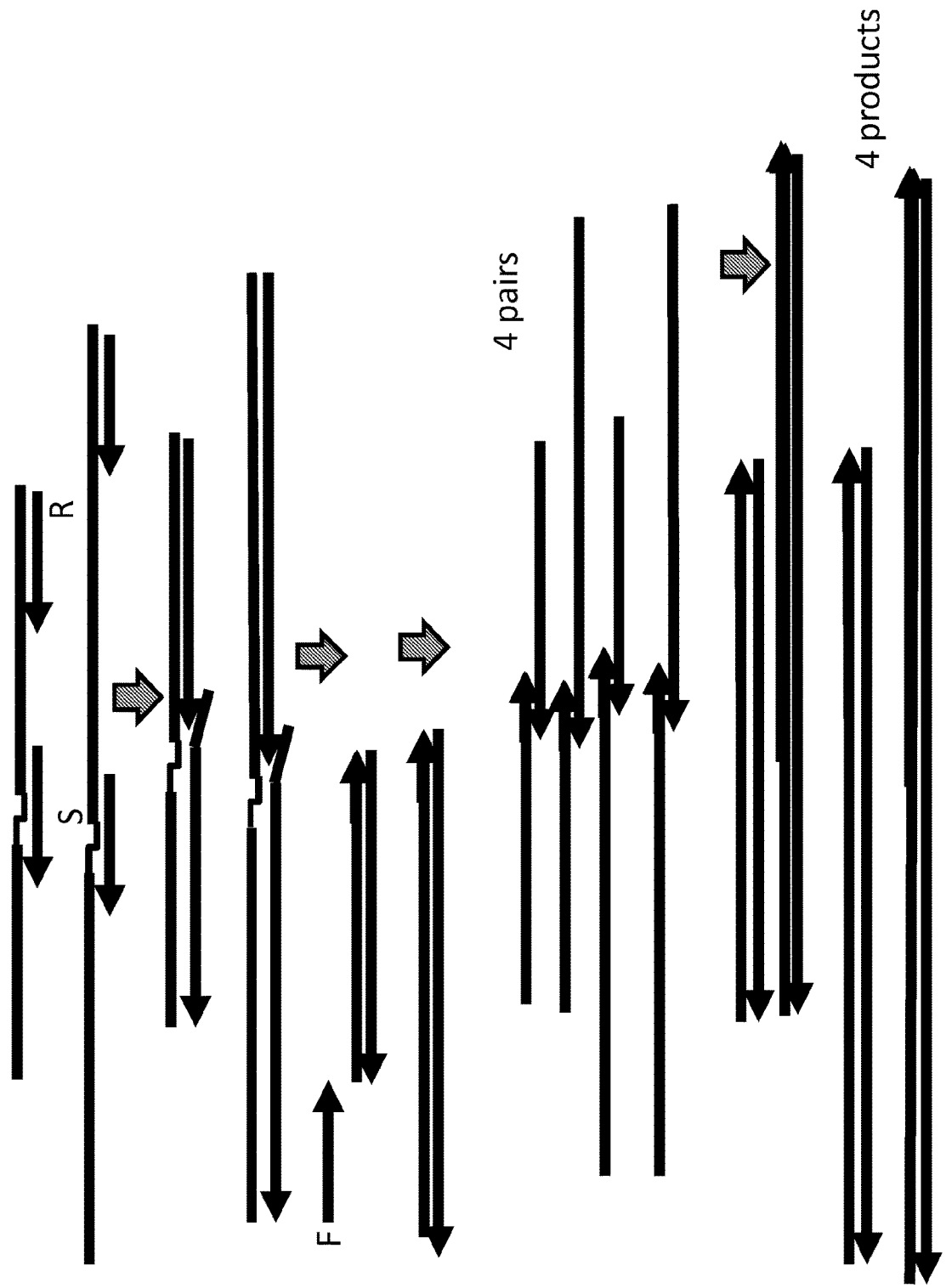
FIG. 36 shows the possible mechanism of the recombination of the splint-dependent-recombination-mediated cDNA generation/PCR amplification products in free solution with consequent shuffling (loss) of tag associations (encoded information).

When both Conjugate_Click_L and Conjugate_Click_S conjugates are mixed and amplified together in free solution in the presence of both terminal primers and the splint primer "ePsplint" and then evaluated by electrophoresis, a ladder of different-mobility products are generated with mobilities that correlate to the lengths of each of the templates as well as with mobilities that correlate to lengths intermediate between each of the templates (lane 5 in FIG. 35). A possible mechanism for this recombination and amplification is presented in FIG. 36.

Figure 37:
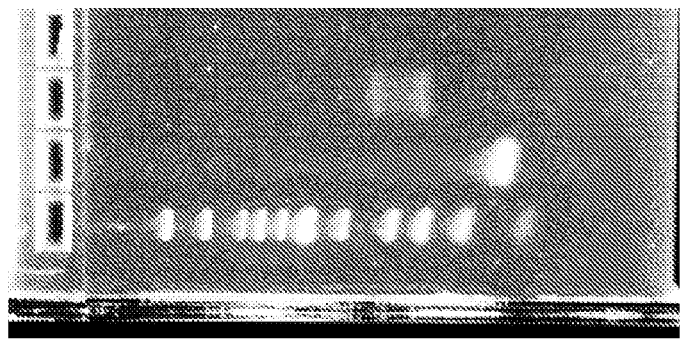
FIG. 37 shows recombination-mediated cDNA generation/PCR amplification of Conjugate_Click_S and Conjugate_Click_L mixture by Deep Vent (exo-) polymerase in free solution and in emulsified aqueous compartments with conditions as follows: 30 seconds at 94° C., 30 seconds at 52° C. and 60 seconds at 72° C. for 35 cycles, and initial conjugate concentration of 5 pM; 1—Marker; 2—free solution, 3—emulsified aqueous compartments.

When both Conjugate_Click_L and Conjugate_Click_S conjugates are mixed and amplified together in a water-in-oil emulsion in the presence of both terminal primers and the splint primer "ePsplint" at low concentration of conjugates relative to emulsion droplets, and then evaluated by electrophoresis, a pair of products are observed with mobilities that correlate to the lengths of each of the templates (lane 3 in FIG. 37). Droplets of the emulsion act as individual microreactors, within which isolated individual conjugates are amplified. The oil/surfactant phase was prepared by mixing 4.5% (vol/vol) of Span 80 (Fluka, cat #85548), 0.4% (vol/vol) of Tween 80 (Sigma, cat #S-8074) and 0.05% (vol/vol) of Triton X-100 (Sigma, cat #T-9284) in light mineral oil (Sigma, cat #M-3516). The aqueous phase (50 uL) was made by mixing 5 uL of 10× Thermopol buffer; 2.5 uL of a solution of each 10 uM primer, 1 uL of 100 nM ePsplint primer; 2.5 uL 10 mM dNTP mix (NEB); 2.5 uL DVexo-(NEB), 2.5 uL of BSA (NEB) and water to 50 uL. A 1:1 mixture of the conjugates Conjugate_Click_L and Conjugate_Click_S were added to the reaction to a final concentration of 5 pM. To 50 uL of the aqueous phase, 150 uL of the non-aqueous phase was then added and emulsification was performed by vortexing for 5 minutes. The recombination/amplification process was conducted as follows: 30 seconds at 94° C., 30 seconds at 52° C. and 60 seconds at 72° C. for 32 cycles.

Following the splint-dependent-recombination-mediated cDNA generation/PCR amplification, the emulsion was broken by microcentrifugation at 21,000 g for 20 minutes, then the non-aqueous phase was removed and the aqueous phase and interphase were extracted into chloroform. The aqueous phase was then evaluated by native electrophoresis (4% agarose minigels, Invitrogen CA).

The results of the emulsion-compartmentalized splint-dependent-recombination-mediated cDNA generation/PCR amplification show that the extent of formation of shuffled PCR products is significantly diminished or nonexistent (Lane 3, FIG. 37).

EXAMPLE 12

Figure 38:
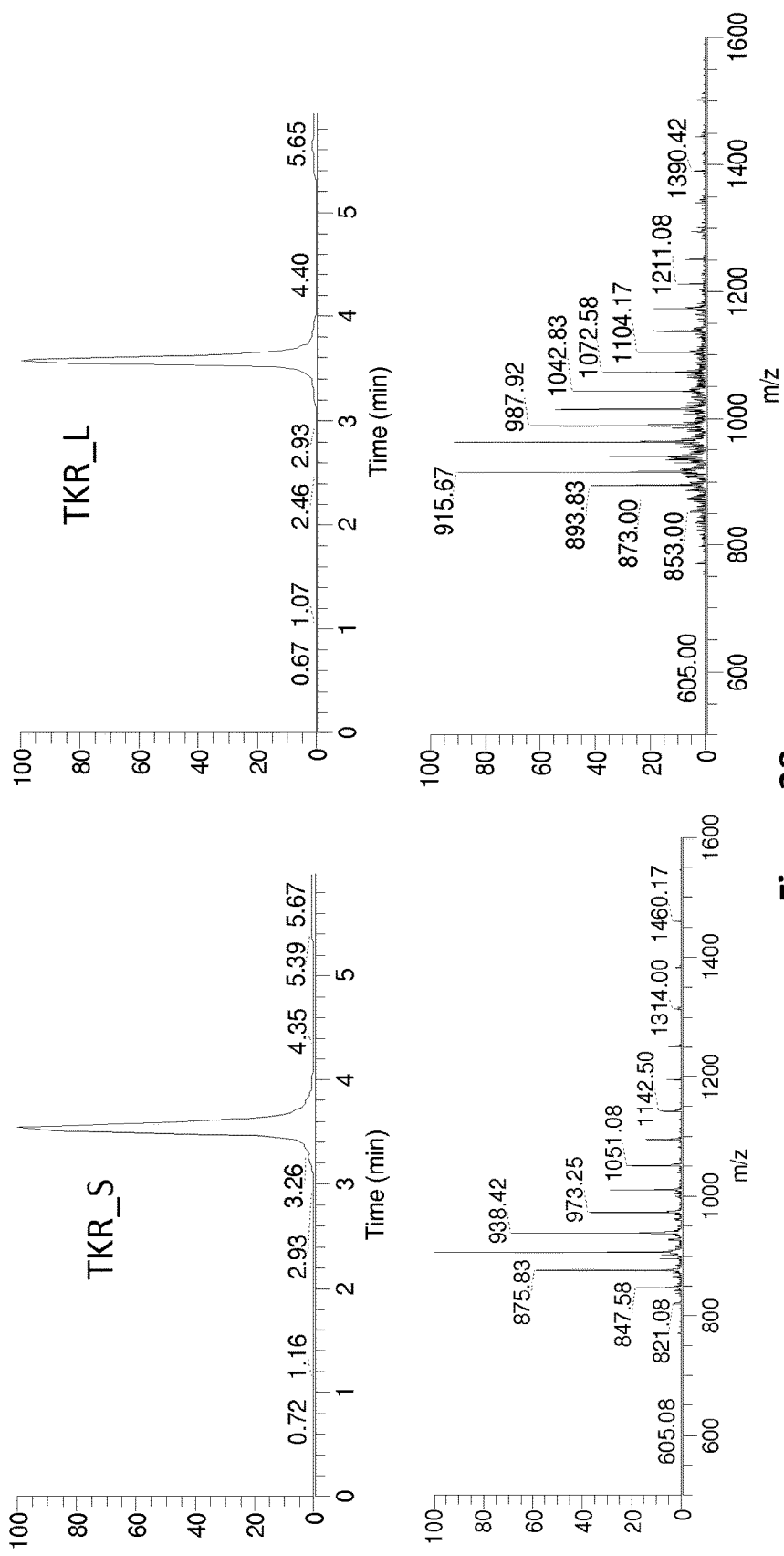
FIG. 38 shows TKR_S and TKR_L conjugates and their LCMS traces.

PCR Amplification of cDNA Derived from Non-Polymerase-Readable Click-Conjugated Model Tags Using Repeat-Homology-Mediated-Recombination in Free Solution to Model the Reading of a Single Tagging Event Two conjugates, TKR_S and TKR_L (FIG. 38), each containing a single non-polymerase-readable click-conjugation linkage formed between a 3'-azido-modified-oligonucleotide and a 5'-hexynyl-modified-oligonucleotide using Cu(I) catalyzed cycloaddition and the protocol described in Example 9. TKR_S and TKR-L each contain a duplicated 12-mer GGAATGAACAGG sequence that flanks the non-polymerase-readable linkage. TKR_S was prepared by conjugating the following two IDT DNA oligonucleotides, TKR_S_$N_3$: TGCGGTCTAACTGTCTAGTT-CACCTTCTCCGGAATGAACAGG/3AzidoN/ (also referred to as S_IDTN$_3$ in Example 9) and TKR_S_Hex: /5'-Hexynyl/GGAATGAACAGGGCCTGATT-GAAGCAATCGGGTGCTATGCTT, while TKR_L was prepared by conjugating two IDT DNA oligonucleotides TKR_L_$N_3$: TGCGGTCTAACTGTCTAGGCACTTGTTCGTTTGCCA GTGTGATGGACACCACTTGGAATGAACAGG/3AzideN/ and TKR_L_Hex: /5'Hexynyl/GGAATGAACAGGG-GAATGAACAGGTTCCTCGTACAGTTCTAAGGCGCT-CAATCGGGTGCTA TGCTT. Both conjugates were PAGE-purified under denaturing conditions and analyzed by LCMS to reveal molecular weights for TKR_S: 26,447.5 Da (26,449.2 Da calculated), and for TKR_L 37,582.6 Da (37,584.4 calculated).

The two conjugates were each diluted to 1 nM and were used for a repeat-dependent-recombination-mediated cDNA generation/PCR amplification with Deep Vent (exo-) DNA polymerase (NEB) in free solution with the forward primer TGCGGTCTAACTGTCTA and the reverse primer AAGCATAGCACCCGATT (IDT).

The repeat-dependent-recombination-mediated cDNA generation/PCR amplification reaction was performed using Deep Vent (exo-) DNA polymerase (NEB). 5 uL of 10× Thermopol buffer; 2.5 uL of a 10 uM solution of each forward and reverse primer; 2.5 uL 10 mM dNTP mix (NEB); 40 pM final concentration of either conjugate or their 1:1 mixture, 2.5 uL Deep Vent (exo-) Polymerase and water to a final volume of 50 uL. The reaction was thermally cycled 22 times as follows: 30 seconds at 94° C., 30 seconds at 52° C. and 60 seconds at 72° C.

Figure 39:
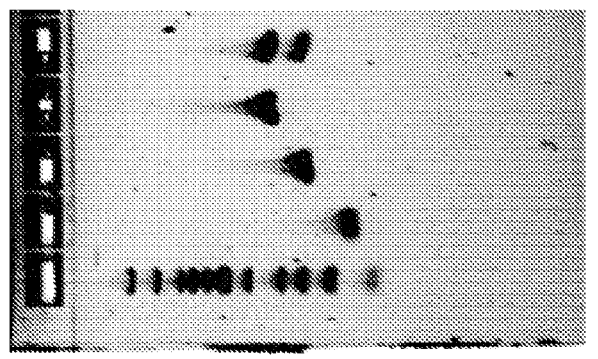
FIG. 39 shows Deep Vent (exo-) Polymerase repeat-dependent-recombination-mediated cDNA generation/PCR amplification of TKR_S and TKR_L. 1—Marker, 2—no template, 3—TKR_S, 4—TKR_L, 5—TKR L and TKR_S. Conditions: 5 uL of 10× Thermopol buffer; 2.5 uL of a 10 uM solution of each forward and reverse primer; 2.5 uL 10 mM dNTP mix (NEB); 40 pM final concentration of either conjugate or their 1:1 mixture, 2.5 uL Deep Vent (exo-)

The products were visualized on a 4% agarose minigel (Invitrogen) (FIG. 39).

The Deep Vent (exo-) Polymerase repeat-dependent-recombination-mediated cDNA generation/PCR amplification reaction produced large amounts of amplicon derived from each separately amplified conjugate (Lanes 3 and 4, FIG. 39). Amplification of the mixture of the conjugates under the same conditions did not result in the production of any intermediate-length amplification products (Lane 5, FIG. 39). To further confirm the lack of shuffling (loss) of tag associations (encoded information) in these amplification products, we cloned and sequenced the amplification products derived from the co-amplified mixture of TKR_S and TKR_L. These sequence data confirmed the complete lack of shuffling of the model tag pairs in the amplification products derived from the co-amplified conjugates (FIG. 40).

EXAMPLE 13

PCR Amplification of cDNA Derived From Unreadable Twice-Click-Conjugated Tags Using Repeat-Homology-Mediated-Recombination in Free Solution to Model the Reading of a Pair of Tagging Events Two conjugates, 2_cl_S and 2_cl_L (FIG. 41), each containing two unreadable click conjugation linkages, each flanked by different 12-mer repeat sequences (GAAGGCGTTATG-click-GAAGGCGTTATG) and (GGAATGAACAGG-click-GGAATGAACAGG), respectively, were prepared in a two-step procedure similar to that described in Example 10.

Firstly, a conjugation was performed using a cyclooctyne-based copper-free click reaction between TKR_central: /5'-Hexynyl/GGAATGAACAGGGTAAGCTGGAGT-GAAGGCGTTATG/3azideN/ (IDT) and either TKR_DBCO_S: (DBCO)GAAGGCGT-TATGTCCGTACTCTTGCAATCGGGTGCTATGCTT or TKR_DBCO_L (DBCO)GAAGGCGTTATGTGA-TATCCGTGGTGTCGTGAGTTCCAATCGGGTGC-TATGCTT. Both DBCO-containing oligonucleotides were obtained from Biosearch (CA), DBCO is the 5'-dibenzocyclooctyne modification for which the phosphoramidite reagent is available from Glen Research (VA)). The products of these conjugations were named TKR_S_$N_3$ and TKR_L_$N_3$ respectively.

Secondly, a conjugation was performed between the products of the first conjugations, TKR_S_$N_3$ and TKR_L_$N_3$, using a Cu (I) catalyzed click reaction. The resulting conjugates, TKR_2_click_S and TKR_2_click_L (FIG. 41) were purified using electrophoresis on a 10% TBE/8M urea polyacrylamide gel and were analyzed by LCMS (Thermo) revealing the expected molecular weights for TKR_2_click_S 38,578.1 Da (38,560.4 Da calculated), and for TKR_2_click_L 49,913.3 Da (49,916.7 Da calculated) (FIG. 41).

The two conjugates were each diluted to 1 nM and were used for a repeat-dependent-recombination-mediated cDNA generation/PCR amplification with Deep Vent (exo-) Polymerase (NEB). For amplification the forward primer TGCGGTCTAACTGTCTA and the reverse primer AAGCATAGCACCCGATT (IDT DNA) were used with 5 uL of 10× Thermopol buffer; 2.5 uL of a 10 uM solution of each forward and reverse primer; 2.5 uL 10 mM dNTP mix (NEB); 40 pM final concentration of either conjugate or their 1:1 mixture, 2.5 uL Deep Vent (exo-) Polymerase and water to 50 uL. The reaction was thermally cycled 22 times as follows: 30 seconds at 94° C., 30 seconds at 52° C. and 60 seconds at 72° C. The amplification products were visualized on 4% agarose minigels (Invitrogen).

The Deep Vent (exo-) polymerase repeat-dependent-recombination-mediated cDNA generation/PCR amplification reaction produced large amounts of amplicon derived from each separately amplified conjugate (Lanes 3 and 4, FIG. 42). Amplification of the mixture of the conjugates under the same conditions did not result in the production of any intermediate-length amplification products (Lane 5, FIG. 42). To further confirm the lack of shuffling (loss) of tag associations (encoded information) in these amplification products, we cloned and sequenced the amplification products derived from the co-amplified mixture of TKR_2_click_S and TKR_2_click_L. These sequence data confirmed the complete lack of shuffling of the model tag pairs in the amplification products derived from the co-amplified conjugates (FIG. 43).

Other Embodiments

All publications, patent applications, and patents mentioned in this specification are herein incorporated by reference.

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, pharmacology, or related fields are intended to be within the scope of the invention.

What is claimed is:

1. A complex comprising:
   (i) a chemical entity comprising one or more scaffolds or one or more building blocks;
   (ii) a headpiece having a first functional group operatively associated with said chemical entity and a second functional group operatively associated with an a first oligonucleotide tag via a first linkage;
   (iii)-n number of additional oligonucleotide tags having n additional linkages, wherein n is 1, 2, 3, 4, 5, 6, 7, 8, or 9, and wherein each of said additional linkages is between two adjacent tags and each tag encodes the identity of at least one of said one or more scaffolds or building blocks; and
   wherein at least one of said n additional linkages is a cross-linking oligonucleotide that spans the junction between two adjacent tags, and that operatively associates with said two adjacent tags via one or more reversible co-reactive groups, wherein at least one of said one or more reversible co-reactive groups is a cyanovinylcarbazole.

2. The complex of claim 1, wherein at least two of said first linkage and n additional linkages comprise:
   a cross-linking oligonucleotide that spans the junction between said second functional group and said first tag or between two adjacent tags and that operatively associates with said second functional group and said first tag or with said two adjacent tags via one or more reversible co-reactive groups, wherein at least one of said one or more reversible co-reactive groups is a cyanovinylcarbazole.

3. The complex of claim 1 or 2, wherein one or more tags comprise a 5'-connector at the 5'-terminus of said one or more tags and a 3'-connector at the 3'-terminus of said one or more tags.

4. The complex of claim 1, wherein less than about 50% of said first linkage and n additional linkages comprise an enzymatic linkage.

5. The complex of claim 1, wherein said chemical entity is operatively associated to said headpiece via a bifunctional spacer.

6. The complex of claim 1, wherein said chemical entity is covalently attached to said headpiece.

7. The complex of claim 1, wherein said headpiece comprises an oligonucleotide selected from the group consisting of a double-stranded oligonucleotide, a single-stranded oligonucleotide, or a hairpin oligonucleotide.

8. The complex of claim 7, wherein said headpiece comprises a primer-binding region.

9. The complex of claim 1, further comprising one or more first library-identifying tag(s), use tag(s), and/or origin tag(s).

10. The complex of claim 1, wherein said complex comprises RNA, DNA, modified DNA, and/or modified RNA.

11. The complex of claim 1, further comprising a tailpiece.

12. A library comprising one or more complexes of claim 1.

\* \* \* \* \*